US008133685B2

(12) United States Patent
Milbrandt et al.

(10) Patent No.: US 8,133,685 B2
(45) Date of Patent: Mar. 13, 2012

(54) AMPK MODULATION AS A METHOD OF REGULATING STEM CELL AND CANCER STEM CELL PROLIFERATION, SELF-RENEWAL AND DIFFERENTIATION

(75) Inventors: Jeffrey Milbrandt, Clayton, MO (US); Biplab Dasgupta, St. Louis, MO (US)

(73) Assignee: Washington University, Saint Louis, MO (US)

( * ) Notice: Subject to any disclaimer, the term of this patent is extended or adjusted under 35 U.S.C. 154(b) by 330 days.

(21) Appl. No.: 12/384,446

(22) Filed: Apr. 3, 2009

(65) Prior Publication Data

US 2010/0221748 A1 Sep. 2, 2010

Related U.S. Application Data

(60) Provisional application No. 61/042,253, filed on Apr. 3, 2008.

(51) Int. Cl.
*G01N 33/53* (2006.01)
*G01N 33/68* (2006.01)
(52) U.S. Cl. ...................................................... 435/7.1
(58) Field of Classification Search ........................ None
See application file for complete search history.

(56) References Cited

OTHER PUBLICATIONS

Igata 2005 (Circulation Research 97:837-844 and additional supplemental materials).*
Kenney et al. 2000 Molecular and Cellular Biology 20:9055-9067.*
Araki et al, Increased Nuclear NAD Biosynthesis and SIRT1 Activation Prevent Axonal Degeneration. Science, 2004, 305:1010-1013.
Barnes et al, The 5'-AMP-activated protein kinase gamma3 isoform has a key role in carbohydrate and lipid metabolism in glycolytic skeletal muscle. J. Biol. Chem., 2004, 279:38441-38447.
Barriere et al, Mice thrive without Cdk4 and Cdk2 Mol. Oncology, 2007, 1:72-83.
Baumann et al, Inhibition of adenosine monophosphate-activated kinase induces apoptosis in multiple myeloma cells. Anticancer Drugs, 2007, 18:405-10.
Berthet et al, Combined loss of Cdk2 and Cdk4 results in embryonic lethality and Rb hypophosphorylation. Dev. Cell, 2006, 10:563-73.
Blair et al, Mutations in the gamma 2 subunit of AMP-activated protein kinase cause familial hypertrophic cardiomyopathy: evidence for the central role of energy compromise in disease pathogenesis. Hum. Mol. Genet, 2001, 10:1215-1220.
Burkhart and Sage, Cellular mechanisms of tumor suppression by the retinoblastoma gene. Nat. Rev. Cancer, 2008, 8:671-682.
Callaghan et al, Neural precursor cells differentiating in the absence of Rb exhibit delayed terminal mitosis and deregulated E2F 1 and 3 activity. Dev. Biol., 1999, 207:257-70.
Culmsee et al, AMP-activated protein kinase is highly expressed in neurons in the developing rat brain and promotes neuronal survival following glucose deprivation. J. Mol. Neurosci, 2001, 17:45-58.
Dyck, The ischemic heart: starving to stimulate the adiponectin-AMPK signaling axis. Circulation, 2007, 116:2779-2781.

Fajas et al, The retinoblastoma-histone deacetylase 3 complex inhibits PPARgamma and adipocyte differentiation. Dev. Cell, 2002, 3:903-910.
Galderisi et al, Cell cycle regulation and neural differentiation. Oncogene, 2003, 22:5208-5219.
Jones et al, AMP-activated protein kinase induces a p53-dependent metabolic checkpoint. Mol. Cell, 2005, 18:283-293.
Jørgensen et al, Effects of alpha-AMPK knockout on exercise-induced gene activation in mouse skeletal muscle. Mol. Cell, 2005, 18:283-293.
Kim et al, Inhibition of AMP-activated protein kinase sensitizes cancer cells to cisplatin-induced apoptosis via hyper-induction of p53, J. Biol. Chem., 2007, 283:3731-42.
Kuramoto et al, Phospho-dependent functional modulation of GABA(B) receptors by the metabolic sensor AMP-dependent protein kinase. Neuron, 2007, 53:233-247.
Laderoute et al, 5'-AMP-activated protein kinase (AMPK) is induced by low-oxygen and glucose deprivation conditions found in solid tumor microenvironments. Mol. Cell. Biol., 2006, 26:5336-5347.
Lee et al, Energy-dependent regulation of cell structure by AMP-activated protein kinase. Nature, 2007, 447:1017-1020.
Lee et al, Mice deficient for Rb are nonviable and show defects in neurogenesis and haematopoiesis. Nature, 1992, 359:288-294.
Marino et al, Induction of medulloblastomas in p53-null mutant mice by somatic inactivation of Rb in the external granular layer cells of the cerebellum. Genes Dev., 2000, 14:994-1004.
Massague, G1 cell-cycle control and cancer. Nature, 2004, 432, 298-306.
McLear et al, In vivo inactivation of pRb, p107 and p130 in murine neuroprogenitor cells leads to major CNS developmental defects and high seizure rates. Mol. Cell. Neurosci., 2006, 33:260-73.
Miller et al, Macrophage migration inhibitory factor stimulates AMP-activated protein kinase in the ischaemic heart. Nature, 2008, 451:578-582.
Mirouse et al, LKB1 and AMPK maintain epithelial cell polarity under energetic stress. J. Cell Biol., 2007, 177:387-392.

(Continued)

*Primary Examiner* — Daniel E Kolker
(74) *Attorney, Agent, or Firm* — Zackson Law LLC

(57) ABSTRACT

Methods are disclosed for decreasing stem cell proliferation, including cancer stem cell proliferation. These methods comprise administering to stem cells inhibitors of AMP activated protein kinase (AMPK). Methods for promoting stem cell growth by increasing stem cell proliferation, self-renewal and/or differentiation are also disclosed. These methods comprise administering AMPK activators to stem cells. Methods of achieving selective differentiation of stem cells are also disclosed. These methods comprise administering small molecules to stem cells that modulate AMPK activity. Applications of these methods are also disclosed, such as methods of increasing numbers of neuronal progenitor cells. These methods can be used therapeutically, such as for repair of spinal cord injuries, or for stimulating neurogenesis in the hippocampus, and other cell-based therapies. The methods can also be used for screening of compounds that can be activators or inhibitors of AMPK activity.

12 Claims, 59 Drawing Sheets
(48 of 59 Drawing Sheet(s) Filed in Color)

OTHER PUBLICATIONS

Naderi et al, Radiation dose-dependent maintenance of G2 arrest requires retinoblastoma protein. Cell Cycle, 2002, 1:193-200.

Niculescu et al, Effects of p21 (Cip1/Waf1) at both the G1/S and the G2/M cell cycle transitions: pRb is a critical determinant in blocking DNA replication and in preventing endoreduplication. Mol. Cell. Biol., 1998, 18:629-643.

Orford and Scadden, Deconstructing stem cell self-renewal: genetic insights into cell-cycle regulation. Nat. Rev. Genet, 2008, 9:115-128.

Papadimou et al, Interplay between the retinoblastoma protein and LEK1 specifies stem cells toward the cardiac lineage. EMBO J., 2005, 24:1750-61.

Rigberg et al, Hypophosphorylated retinoblastoma protein is associated with G2 arrest in esophageal squamous cell carcinoma. J. Surg. Res., 1999, 84:101-105.

Sankaran et al, Rb intrinsically promotes erythropoiesis by coupling cell cycle exit with mitochondrial biogenesis. Genes Dev., 2008, 22:463-475.

Weintraub et al, Mechanism of active transcriptional repression by the retinoblastoma protein. Nature, 1995, 375:812-815.

Wikenheiser-Brokamp, Rb family proteins differentially regulate distinct cell lineages during epithelial development. Development, 2004, 131:4299-4310.

Xue and Kahn, AMPK integrates nutrient and hormonal signals to regulate food intake and energy balance through effects in the hypothalamus and peripheral tissues. J. Physiol., 2006, 574:73-83.

Yen and Sturgill, Hypophosphorylation of the RB protein in S and G2 as well as G1 during growth arrest. Exp. Cell Res., 1998, 241:324-331.

Yun et al, Glucose deprivation increases mRNA stability of vascular endothelial growth factor through activation of AMP-activated protein kinase in DU145 prostate carcinoma. J. Biol. Chem., 2005, 280:9963-9972.

Zarkowska et al, Differential phosphorylation of the retinoblastoma protein by G1/S cyclin-dependent kinases. J. Biol. Chem., 1997, 272:12738-12746.

* cited by examiner

FIG. 1A
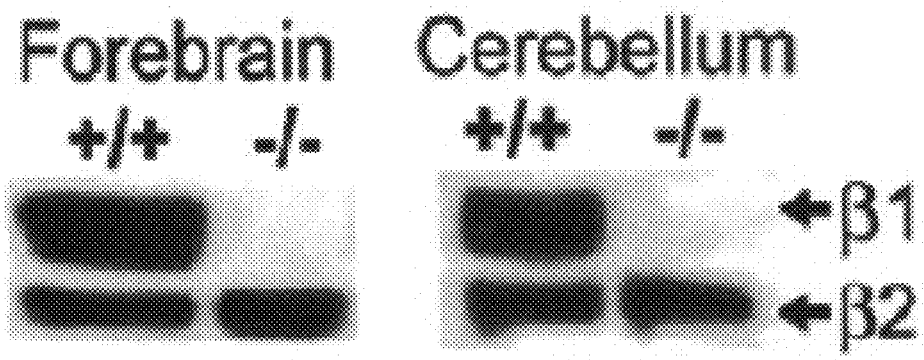
FIG. 1B
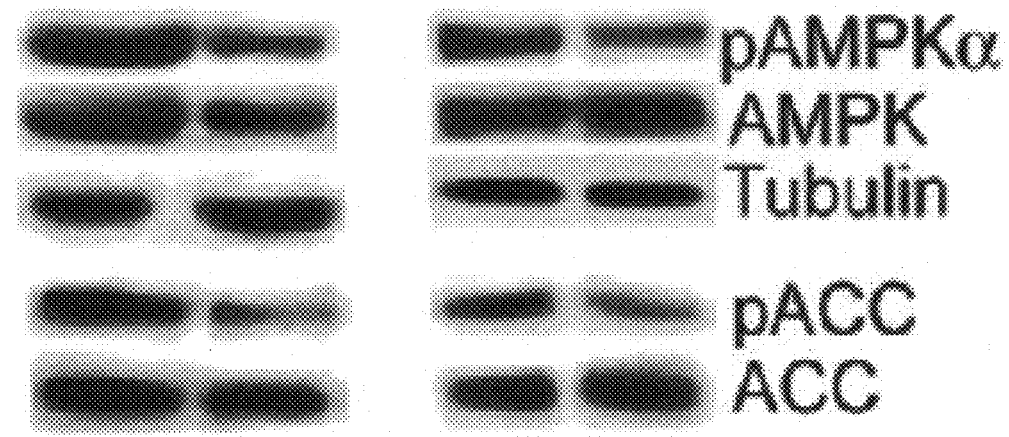
FIG. 1

FIG. 2A
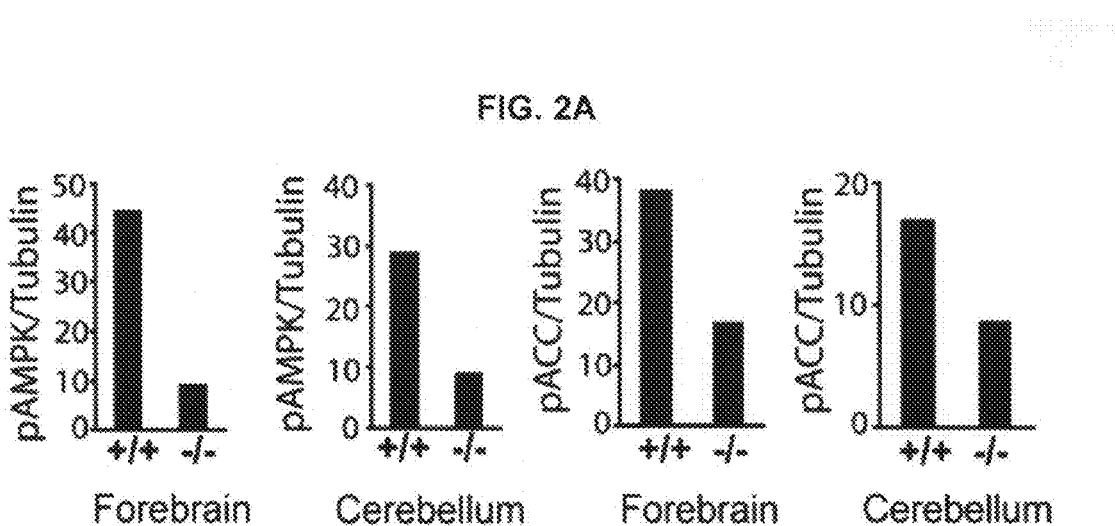
FIG. 2B
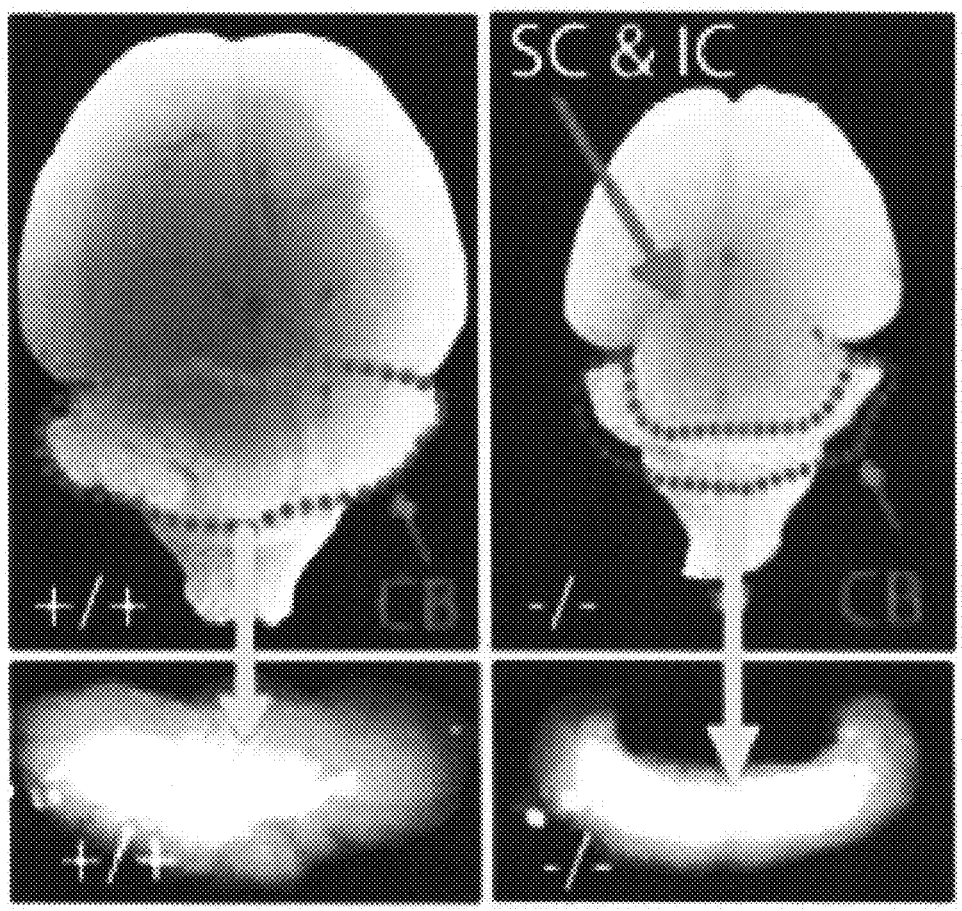
FIG. 2

FIG. 3A
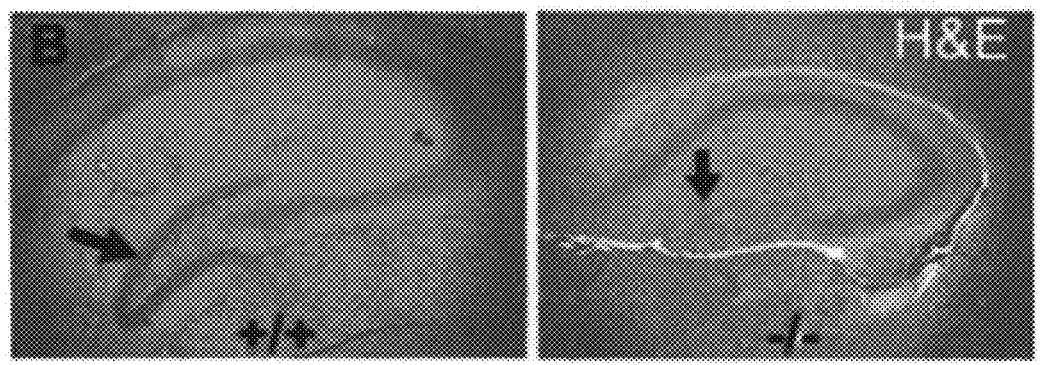
FIG. 3B
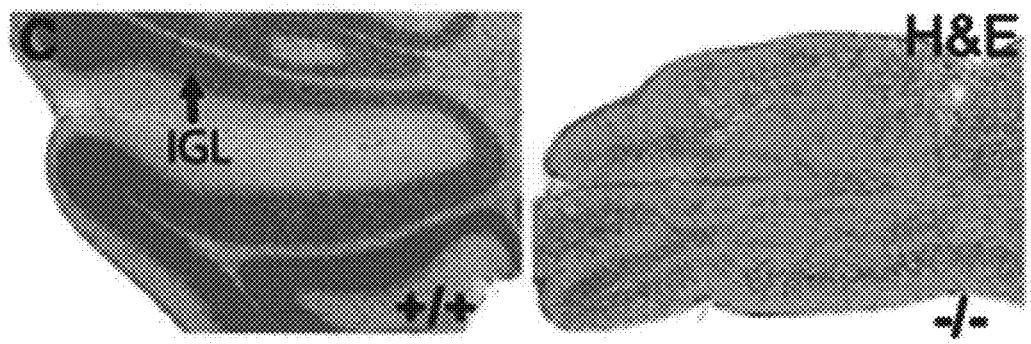
FIG. 3

FIG. 4A
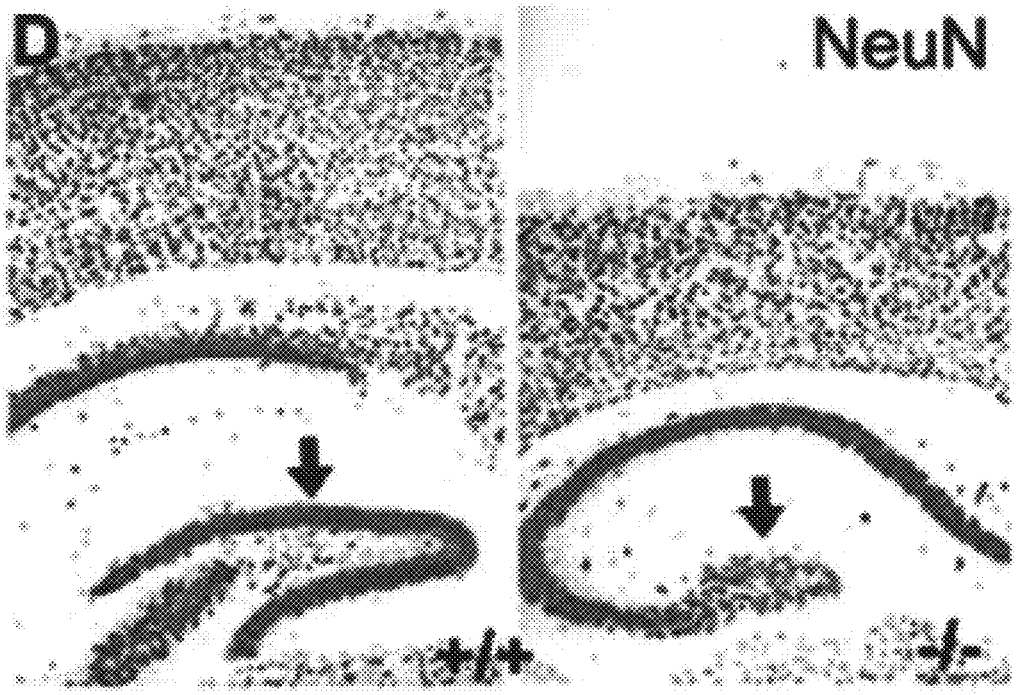
FIG. 4B
FIG. 4

FIG. 6A
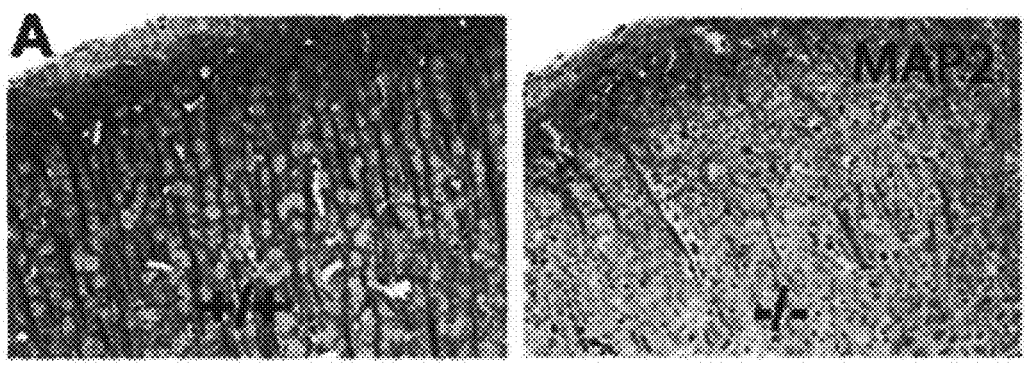
FIG. 6B
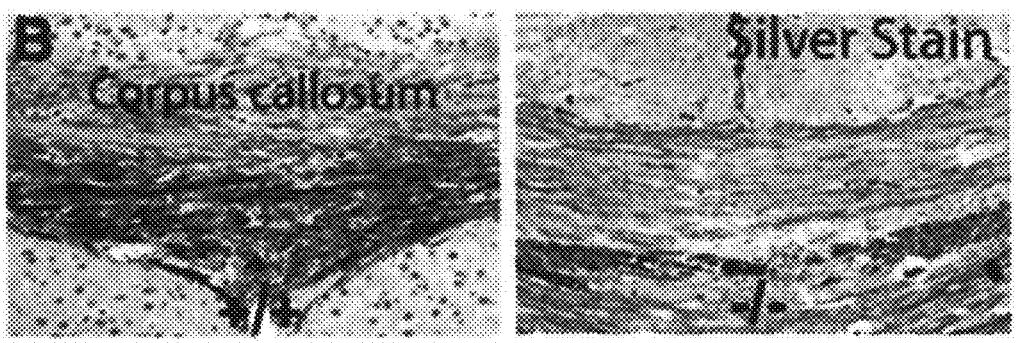
FIG. 6C
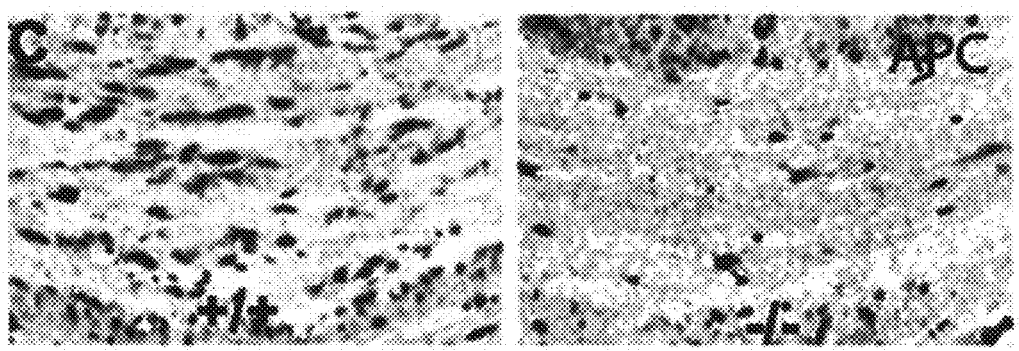
FIG. 6

FIG. 7A
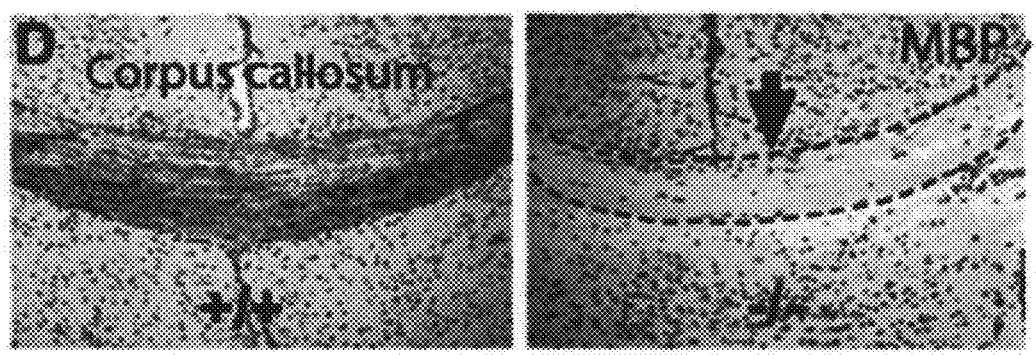
FIG. 7B
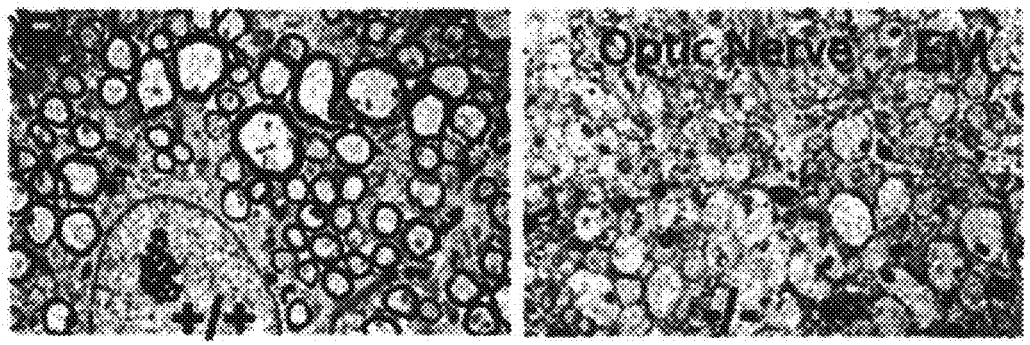
FIG. 7

FIG. 8A
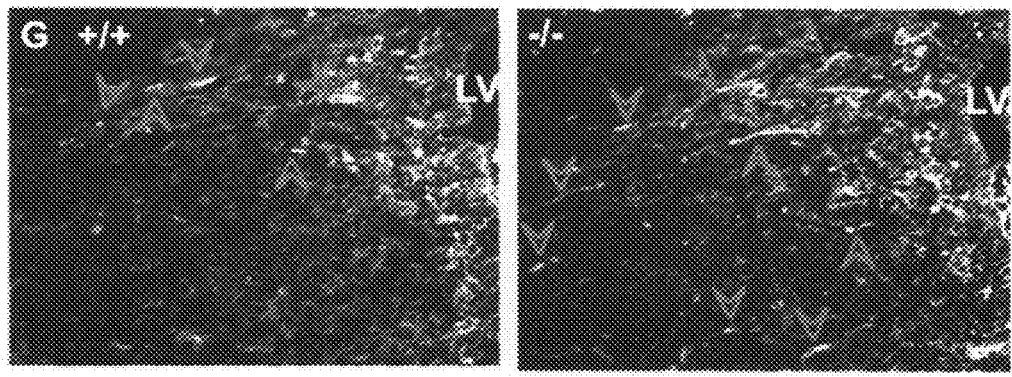
FIG. 8B
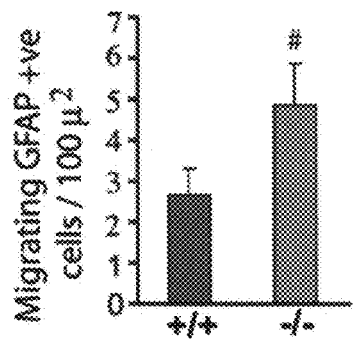
FIG. 8C
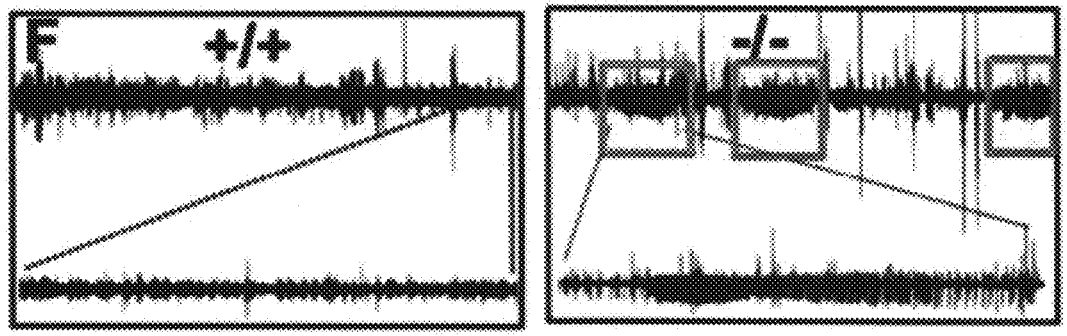
FIG. 8

FIG. 9A
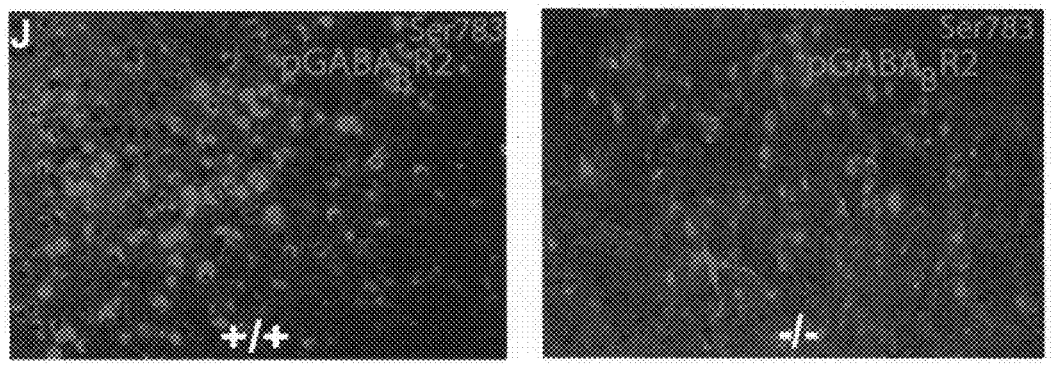
FIG. 9B
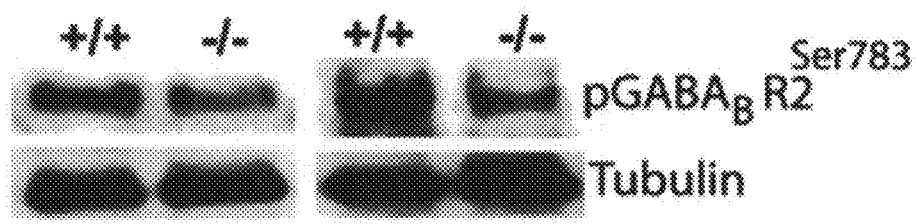
FIG. 9C
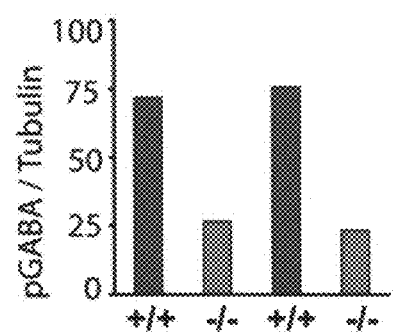
FIG. 9

FIG. 10A
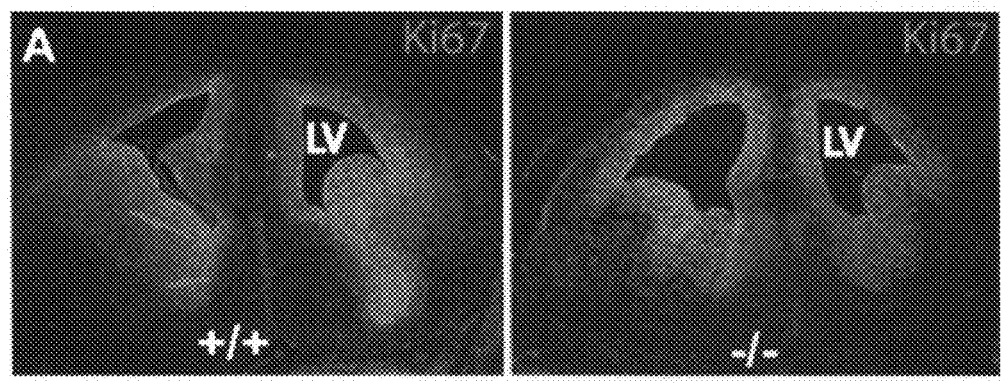
FIG. 10B
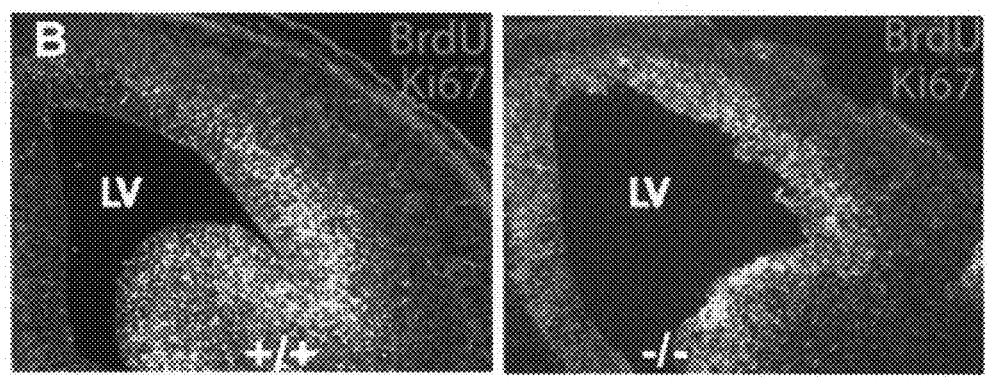
FIG. 10C
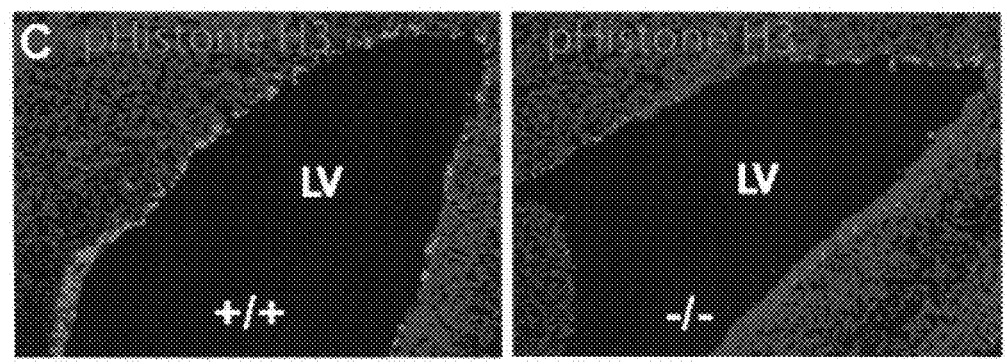
FIG. 10

FIG 11A
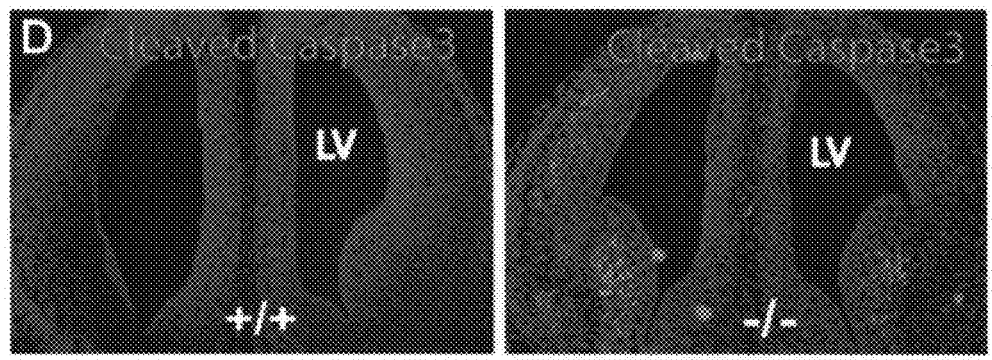
FIG. 11B                FIG. 11C
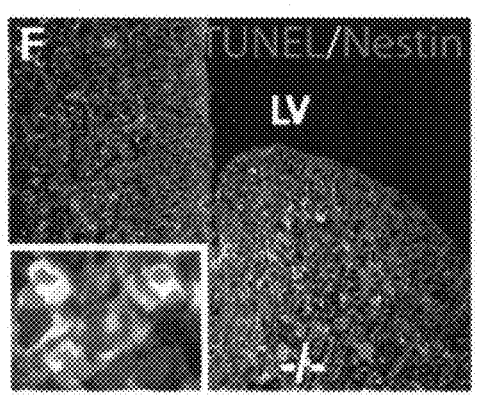 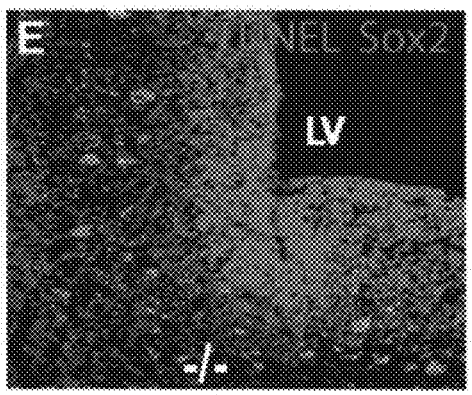
FIG. 11D
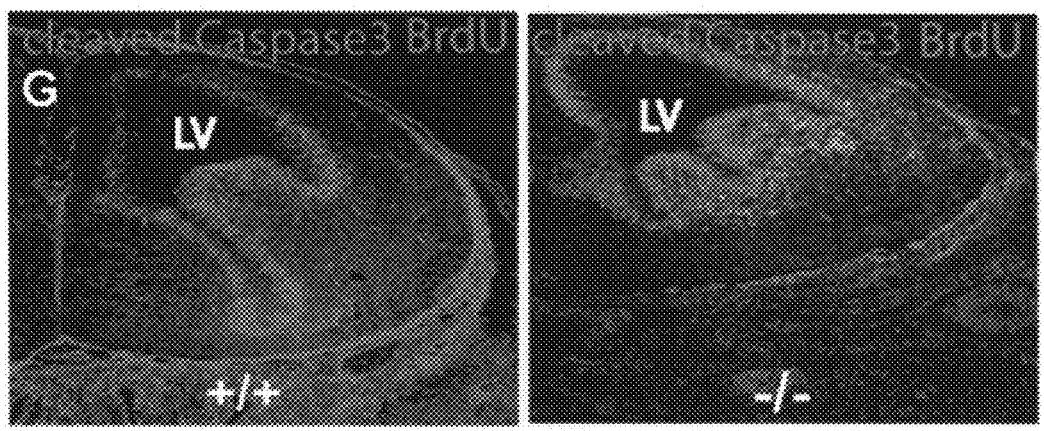
FIG. 11

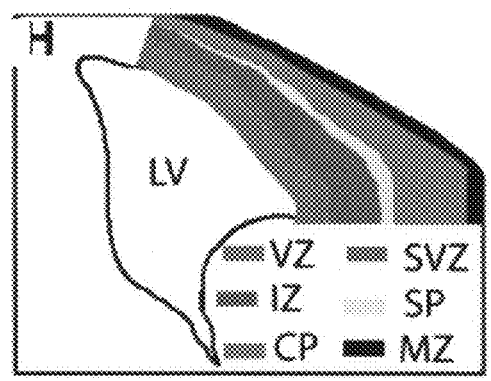
FIG. 12A
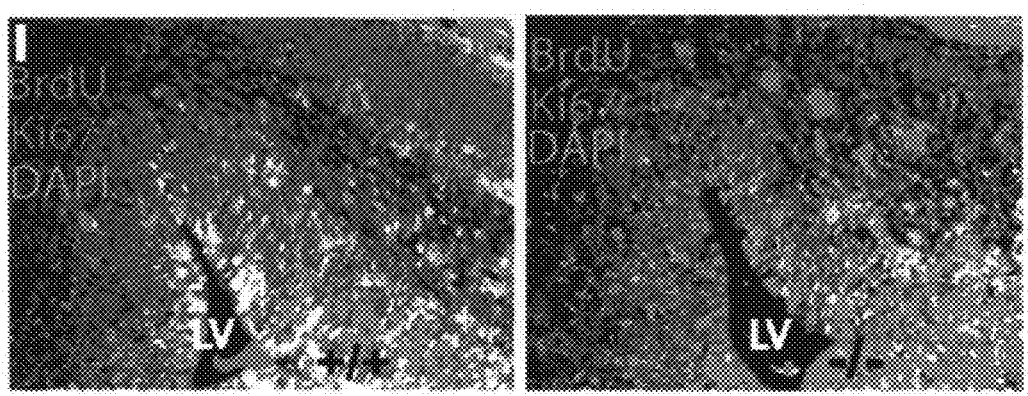
FIG. 12B
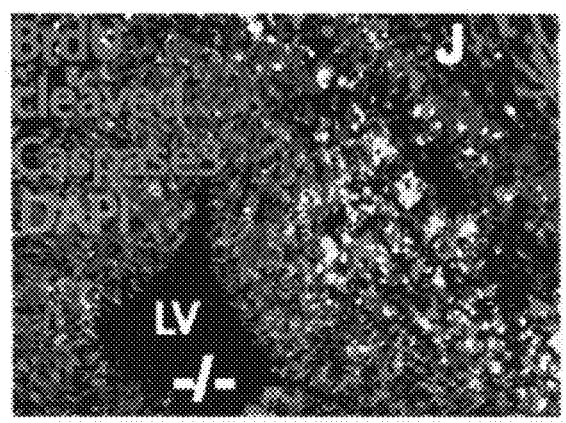
FIG. 12C
FIG. 12

FIG. 13A
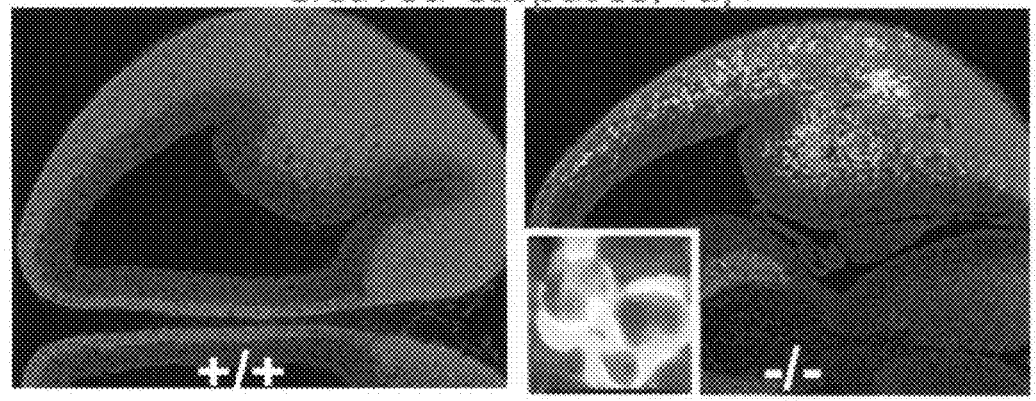
FIG. 13B
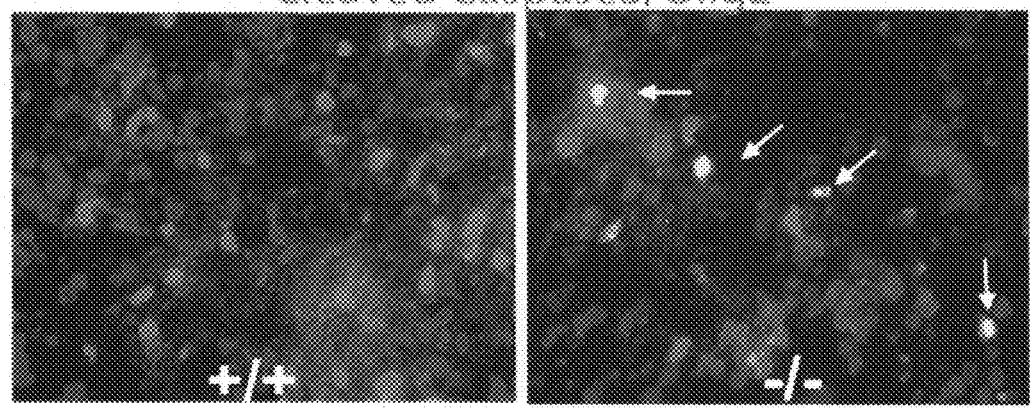
FIG. 13

FIG. 14A
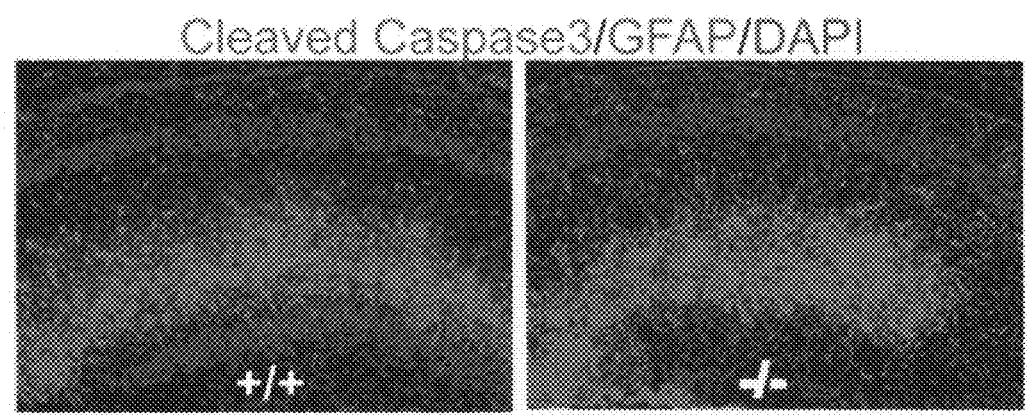
FIG. 14B
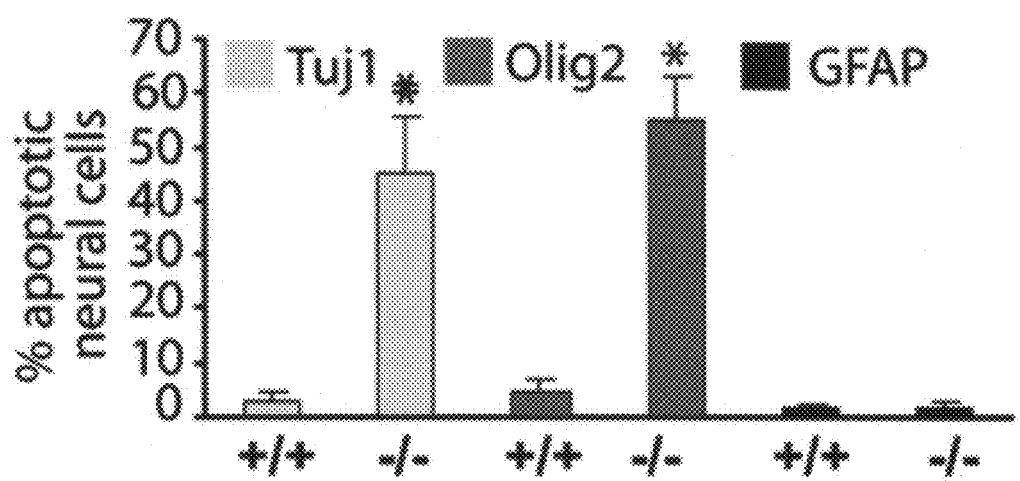
FIG. 14

FIG. 15A
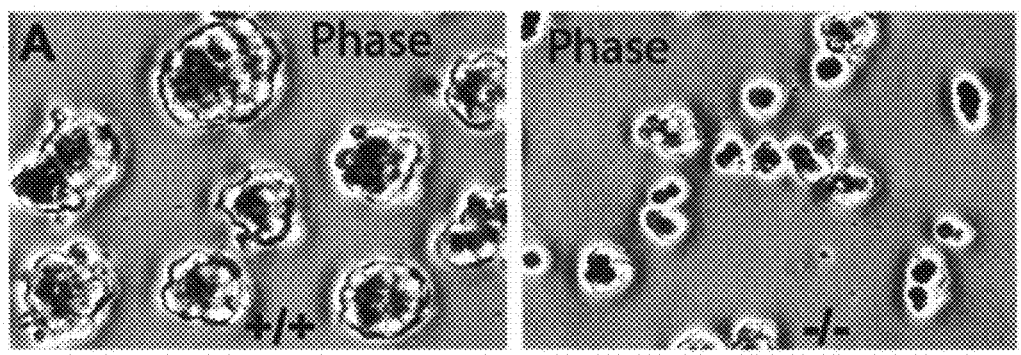
FIG. 15B
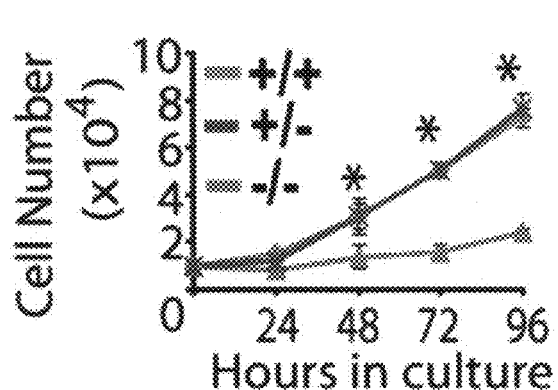
FIG. 15C
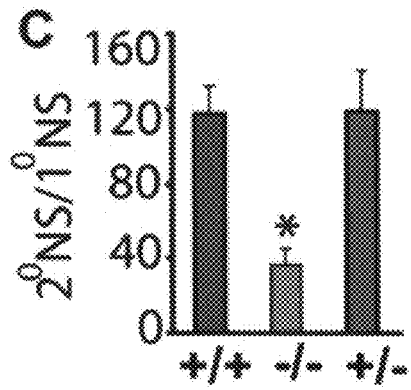
FIG. 15

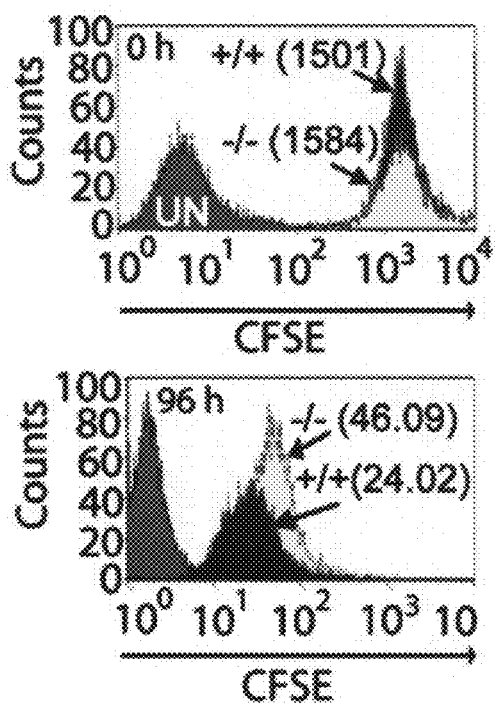
FIG. 16A
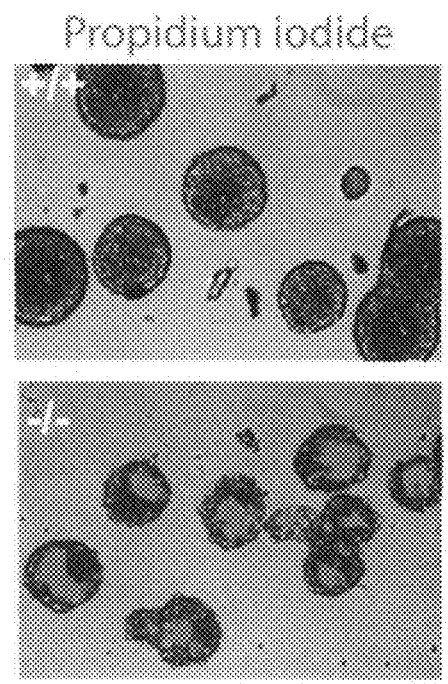
FIG. 16B
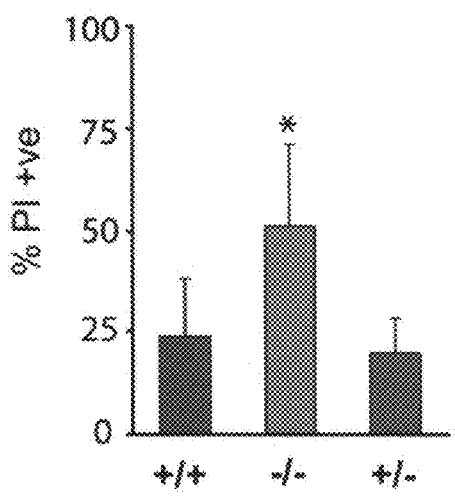
FIG. 16C
FIG. 16

FIG. 17A
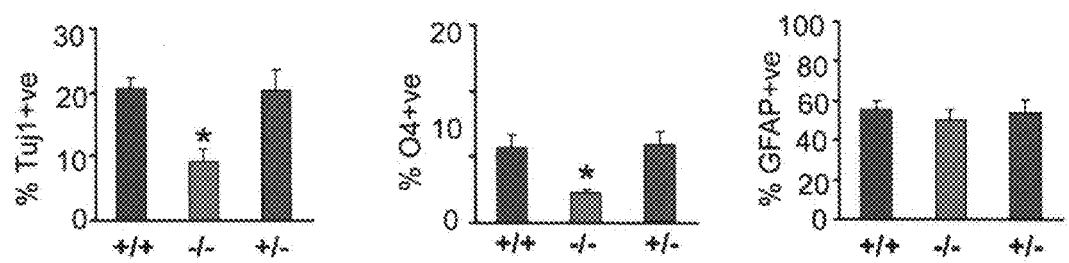
FIG. 17B
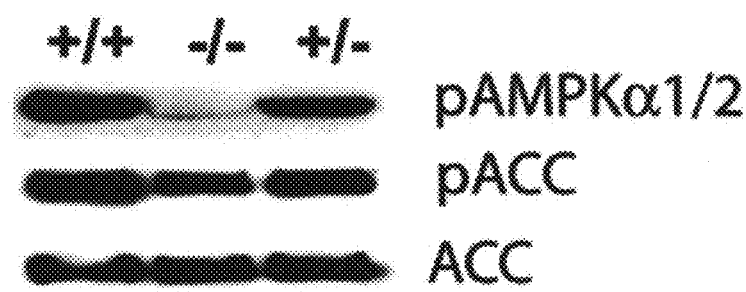
FIG. 17

FIG. 18A
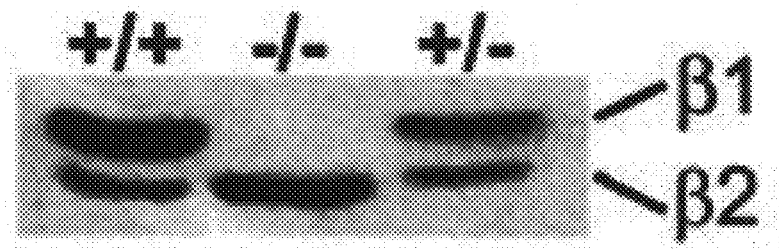
FIG. 18B
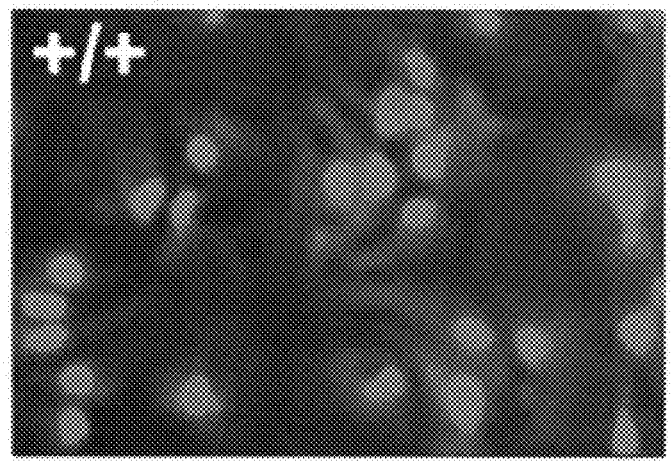
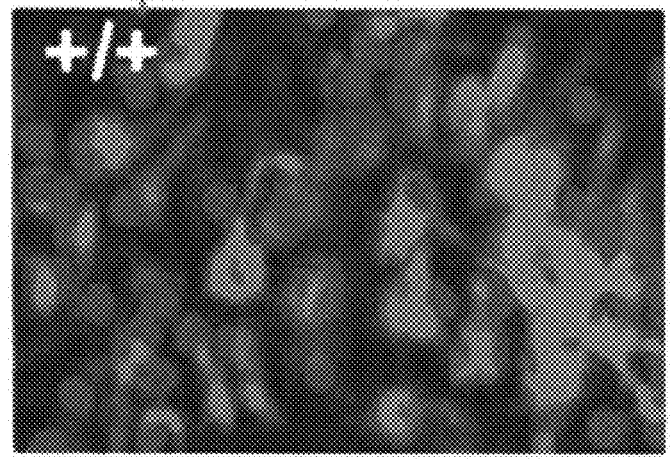
FIG. 18

FIG. 19A
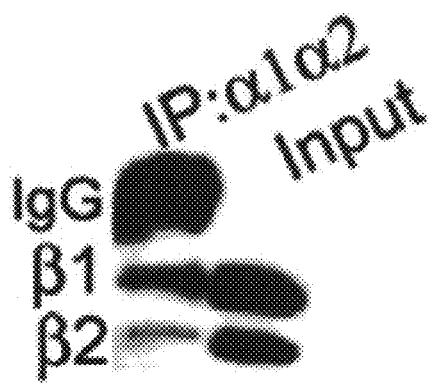
FIG. 19B
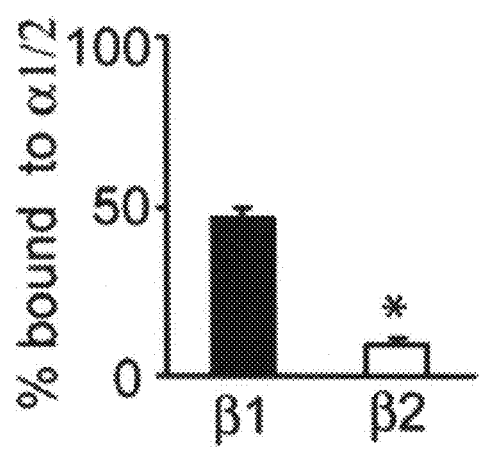
FIG. 19C
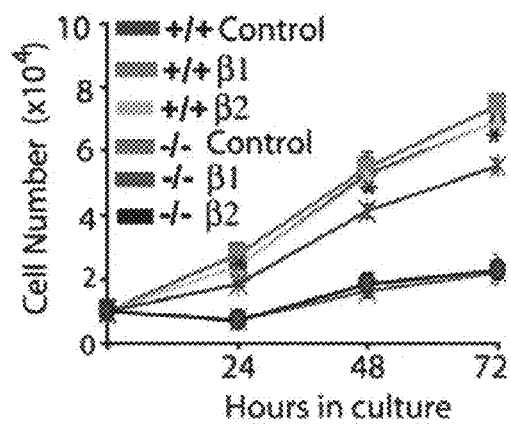
FIG. 19D
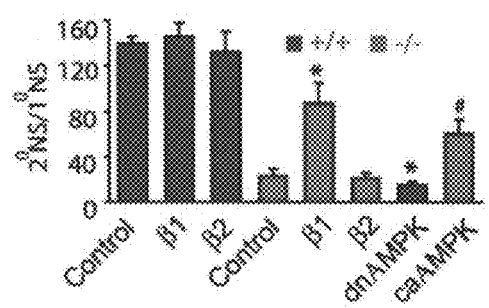
FIG. 19

FIG. 24A
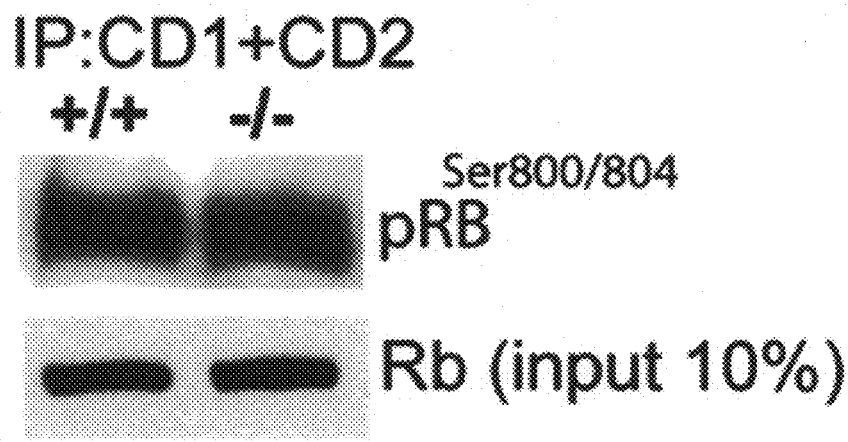
FIG. 24B
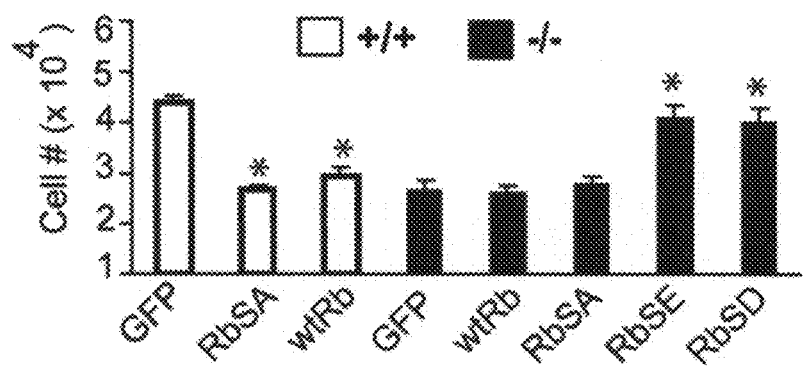
FIG. 24C
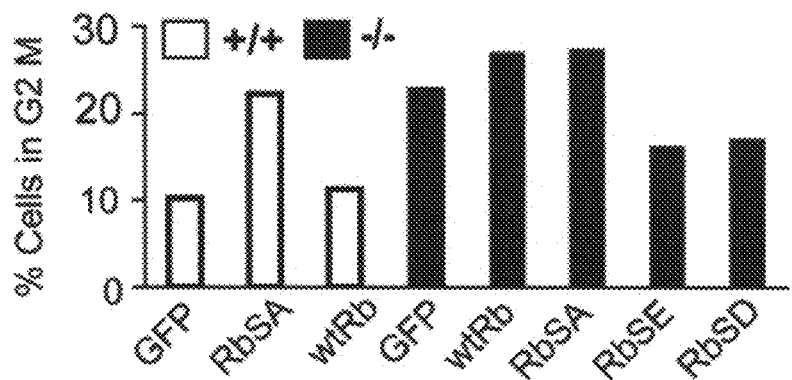
FIG. 24

FIG. 26A
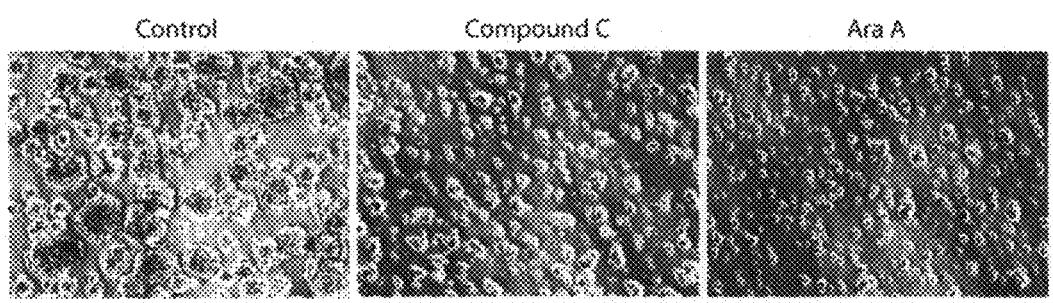
FIG. 26B
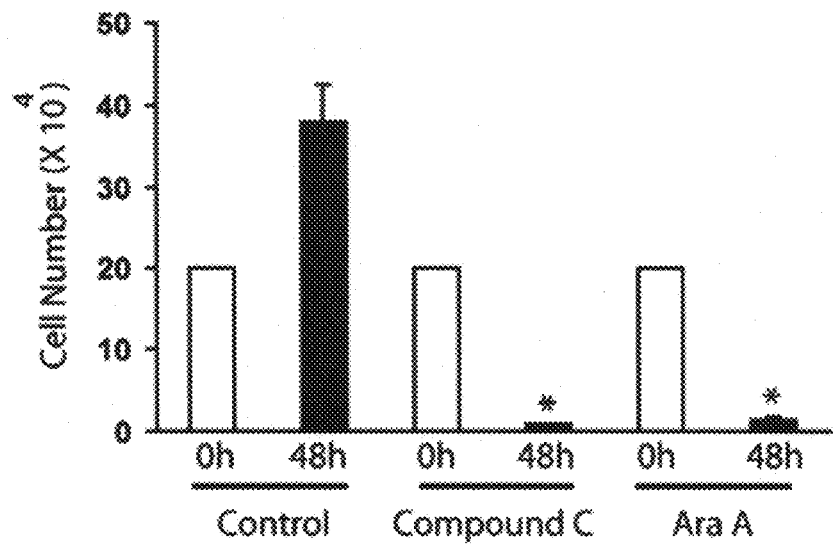
FIG. 26

FIG. 27A
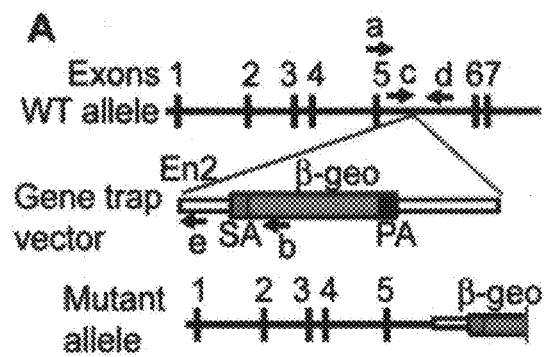
FIG. 27B
FIG. 27C
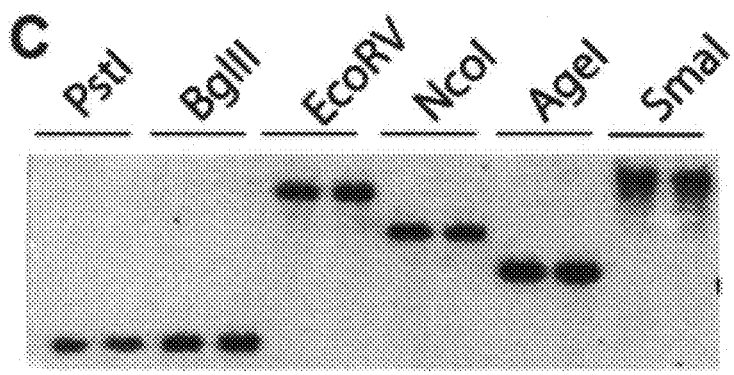
FIG. 27D
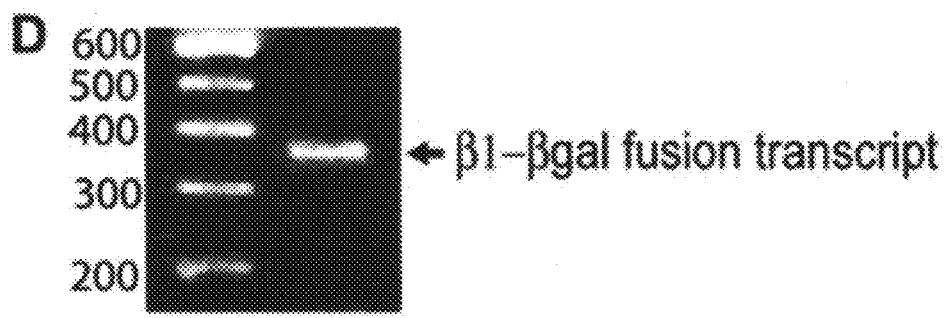
FIG. 27

FIG. 28A
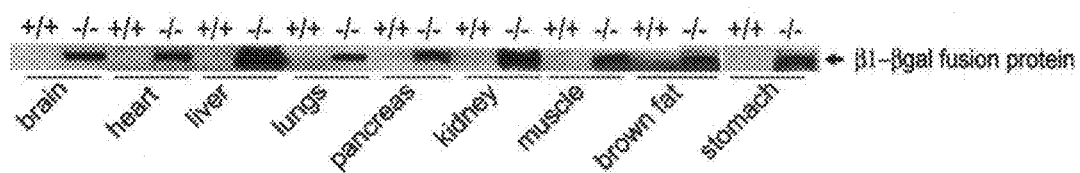
FIG. 28B
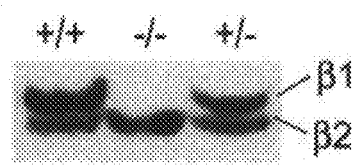
FIG. 28C
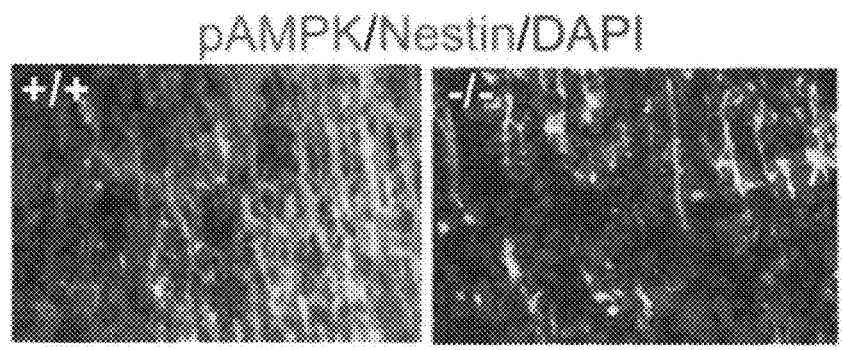
FIG. 28

FIG. 29A
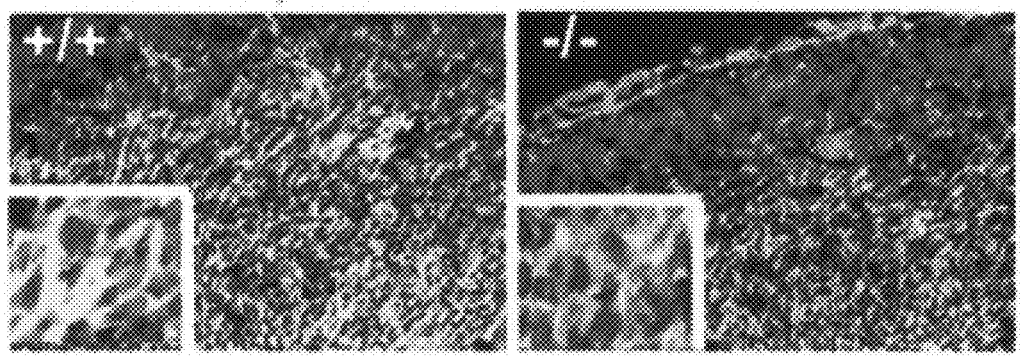
FIG. 29B
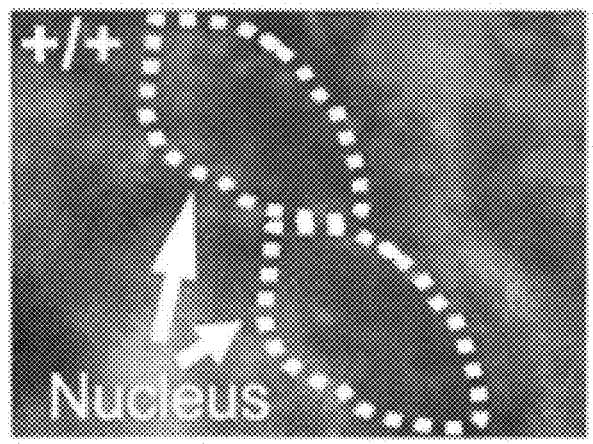
FIG. 29

FIG. 30A
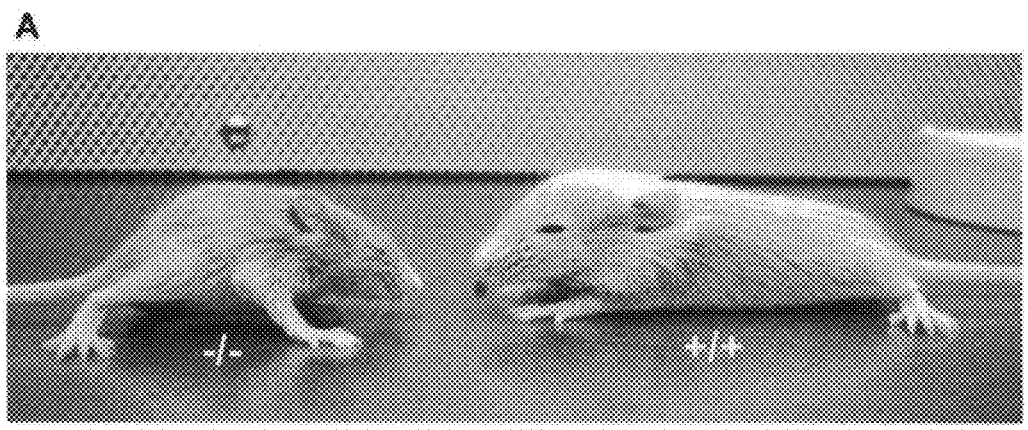
FIG. 30B
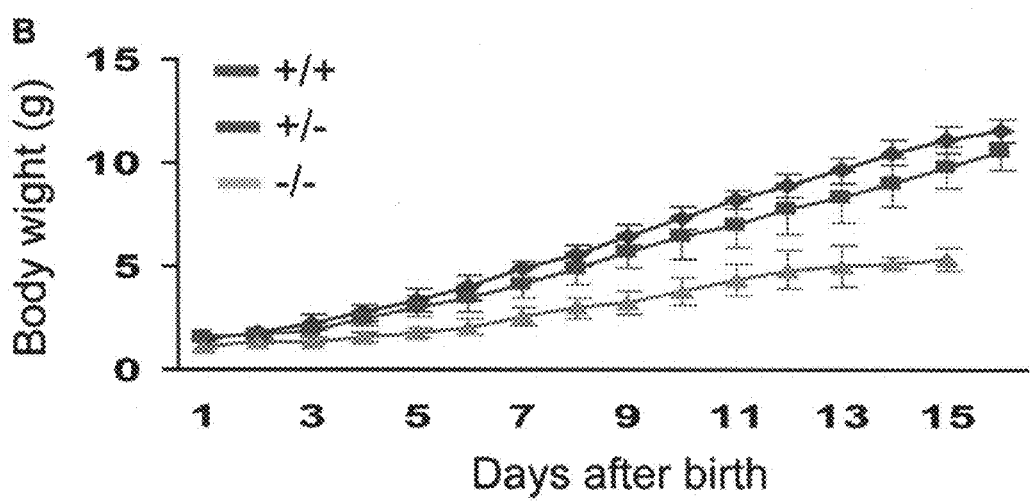
FIG. 30

FIG. 31A
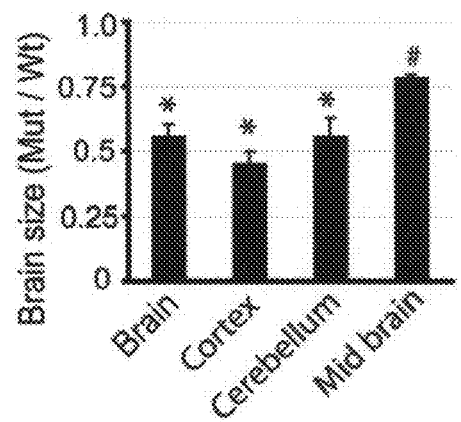
FIG. 31B
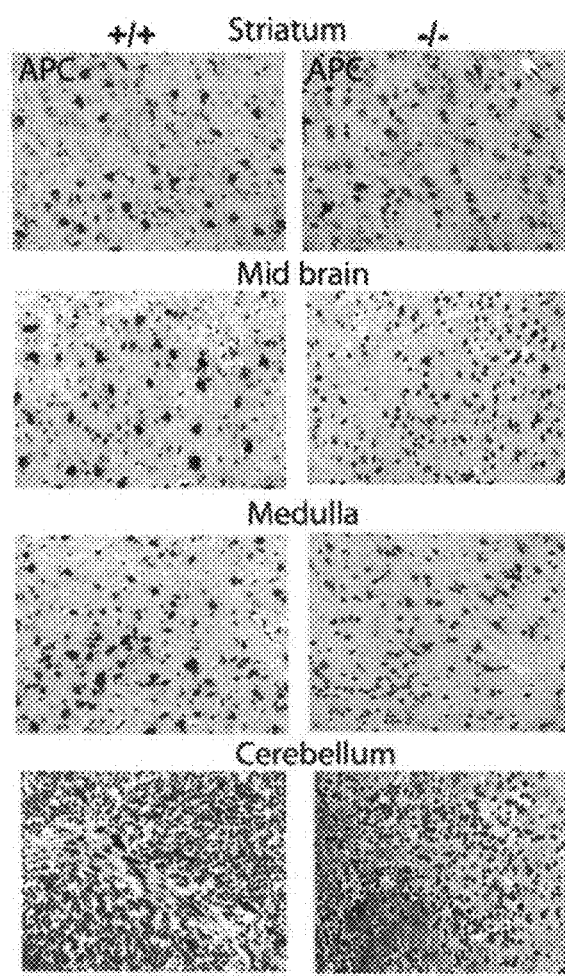
FIG. 31

FIG. 32A
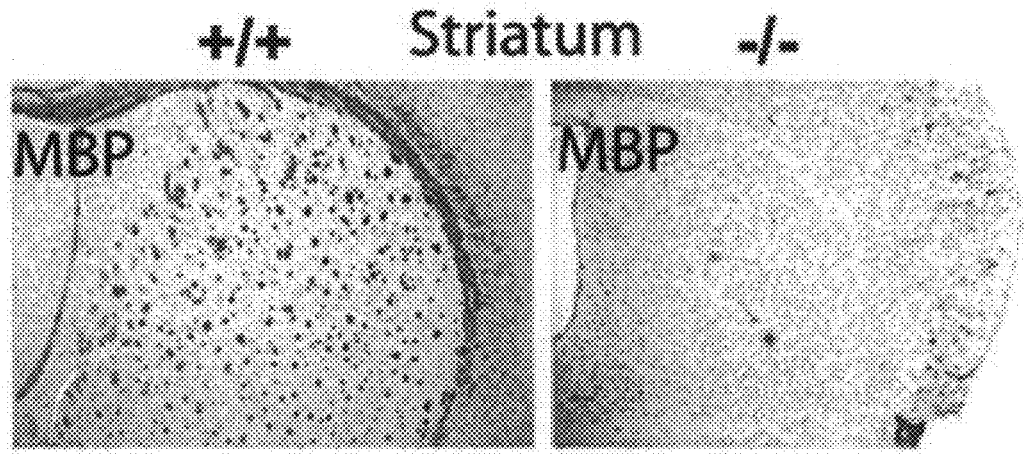
FIG. 32B
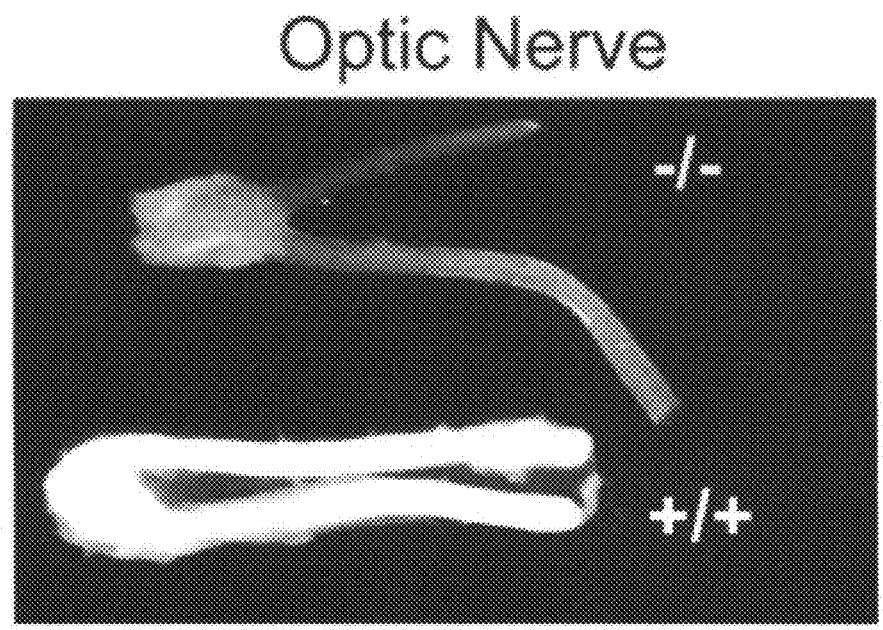
FIG. 32

FIG. 34A
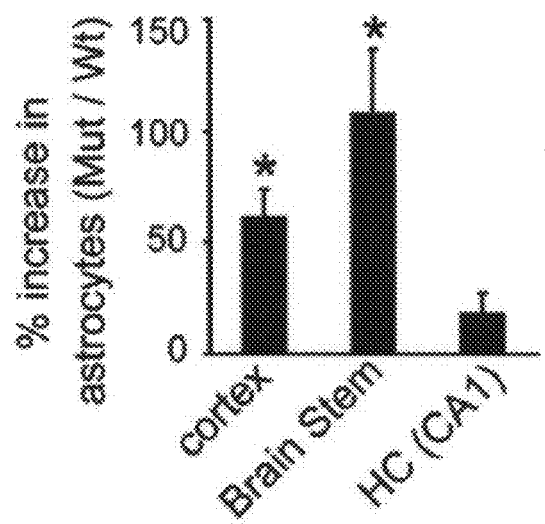
FIG. 34B
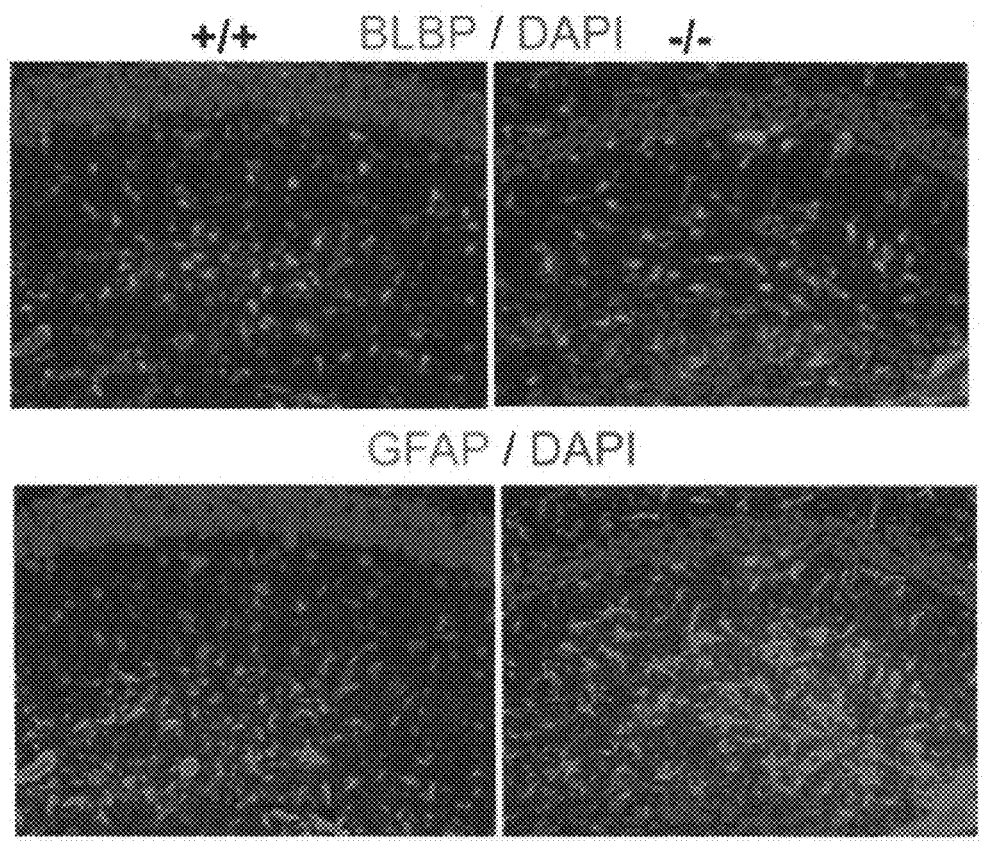
FIG. 34

FIG. 35A
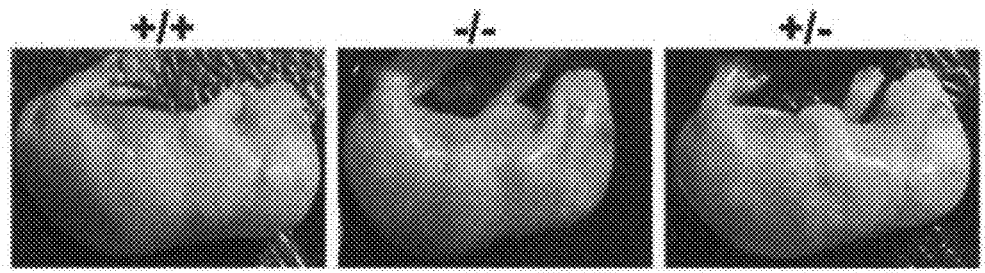
FIG. 35B
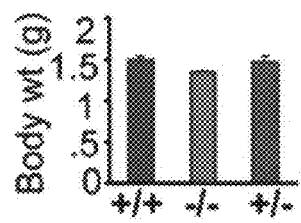
FIG. 35C
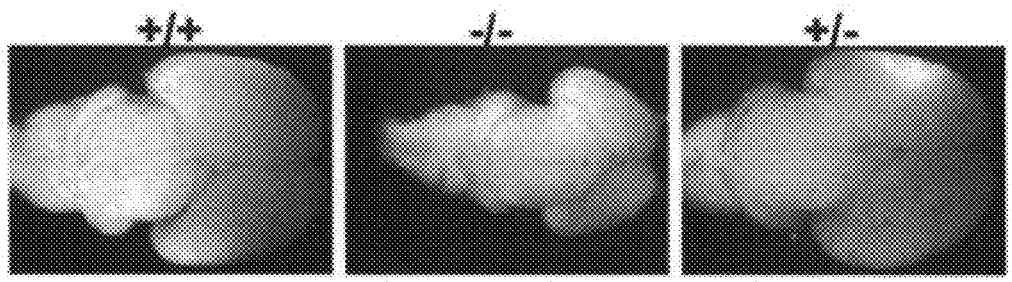
FIG. 35D
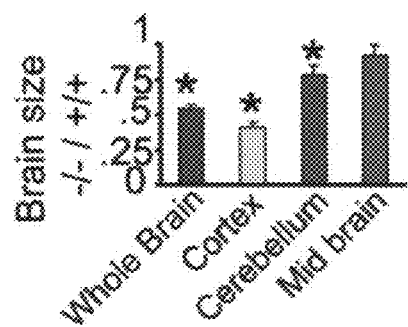
FIG. 35

FIG. 36A
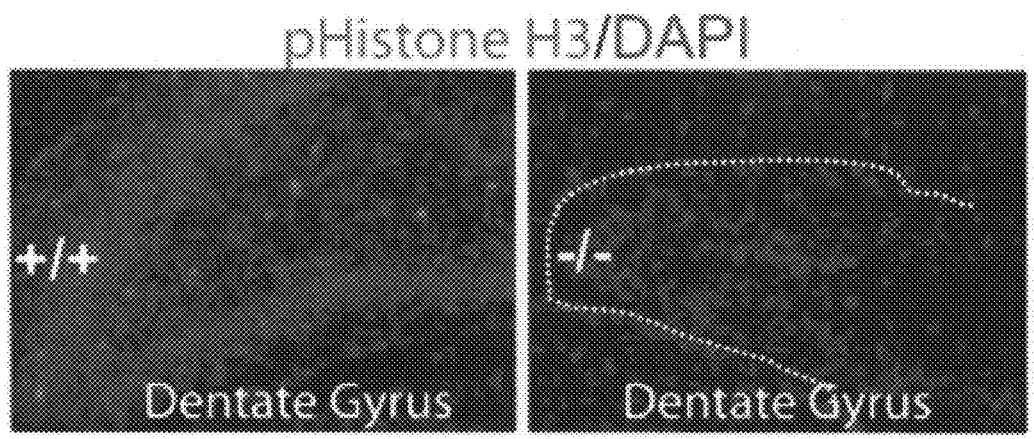
FIG. 36B
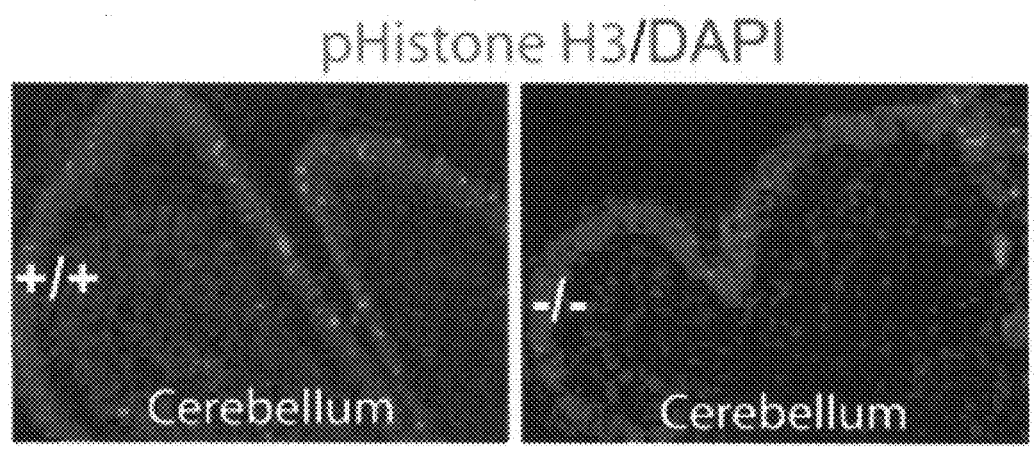
FIG. 36C
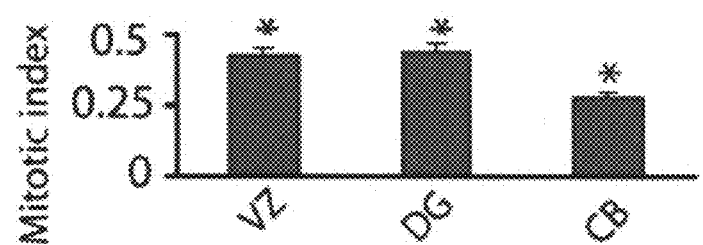
FIG. 36

FIG. 37A
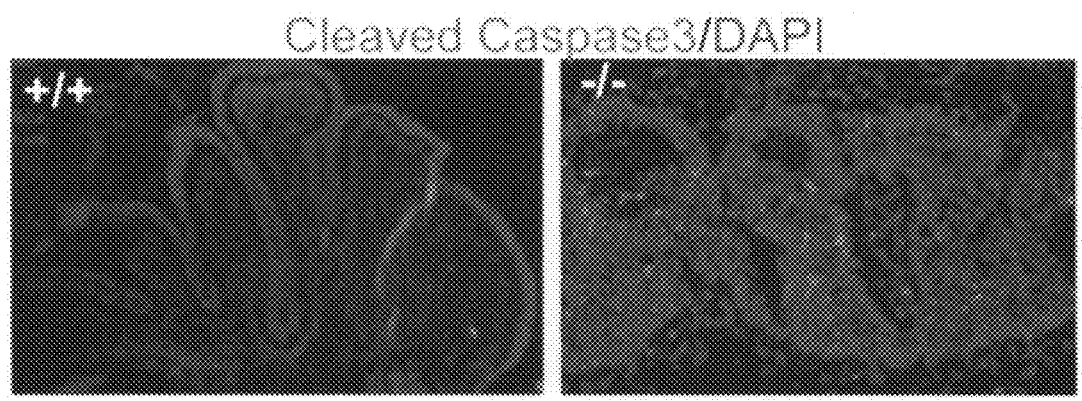
FIG. 37B
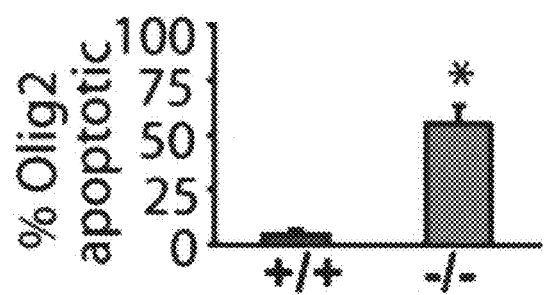
FIG. 37

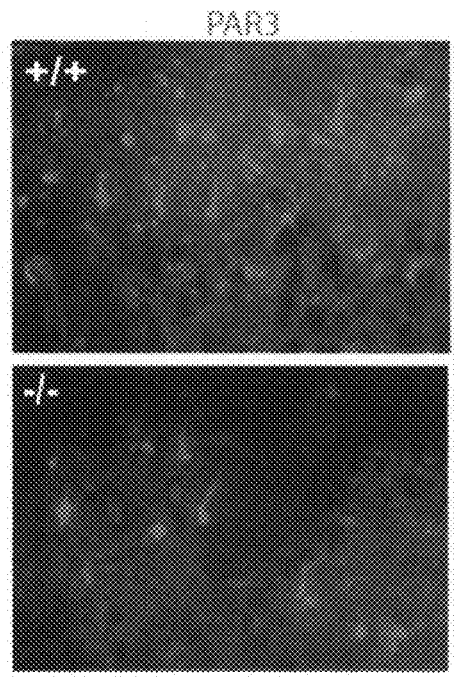
FIG. 38A
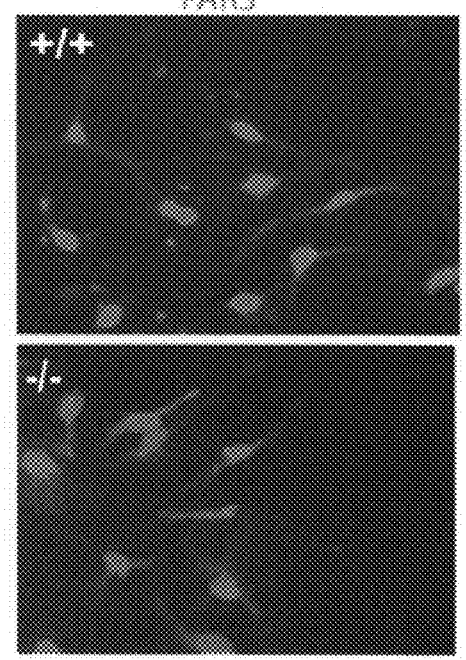
FIG. 38B
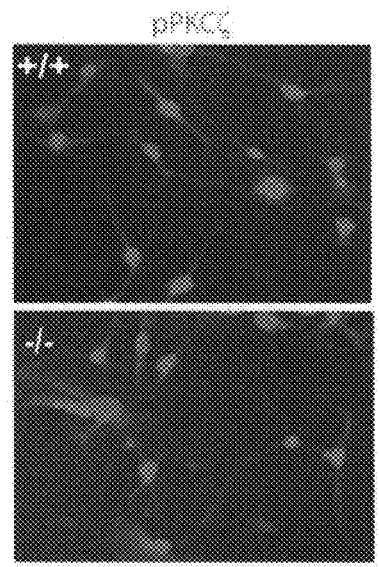
FIG. 38C
FIG. 38

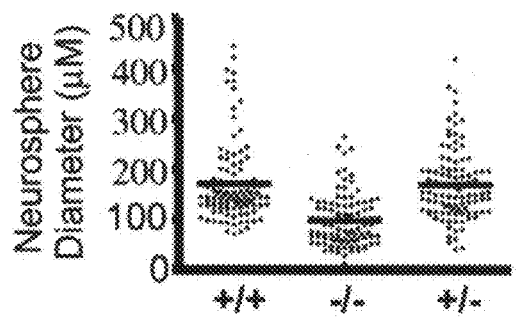
FIG. 39A
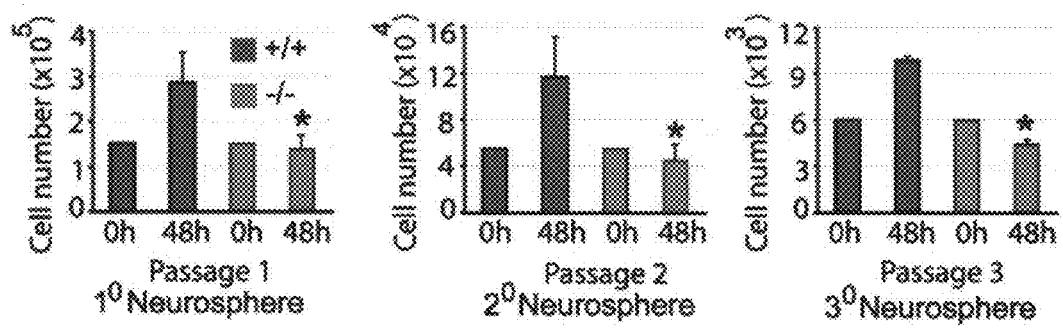
FIG. 39B
FIG. 39C
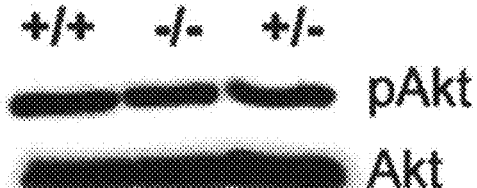
FIG. 39D
FIG. 39

FIG. 40A
Neurons (Tuj1/DAPI)
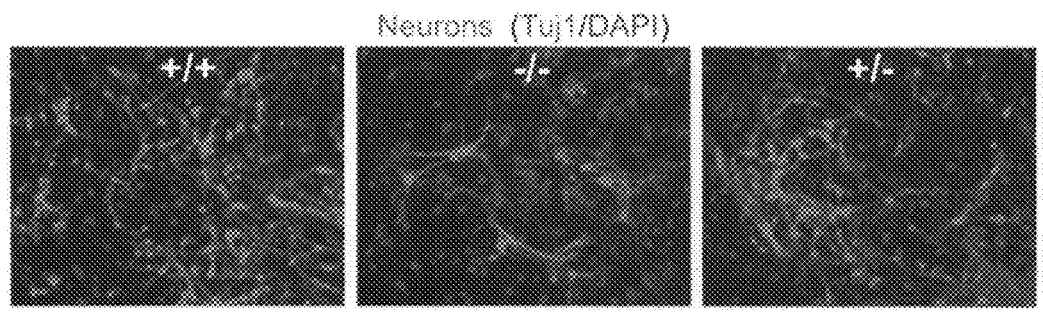
FIG. 40B
Oligodendrocytes (O4/DAPI)
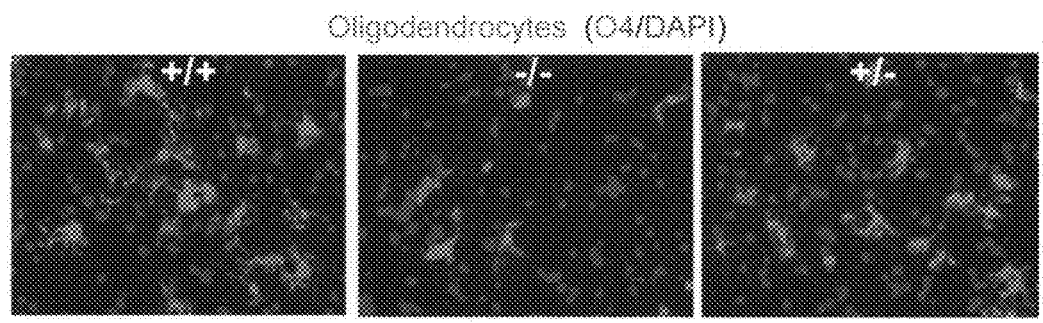
FIG. 40C
Astrocytes (GFAP/DAPI)
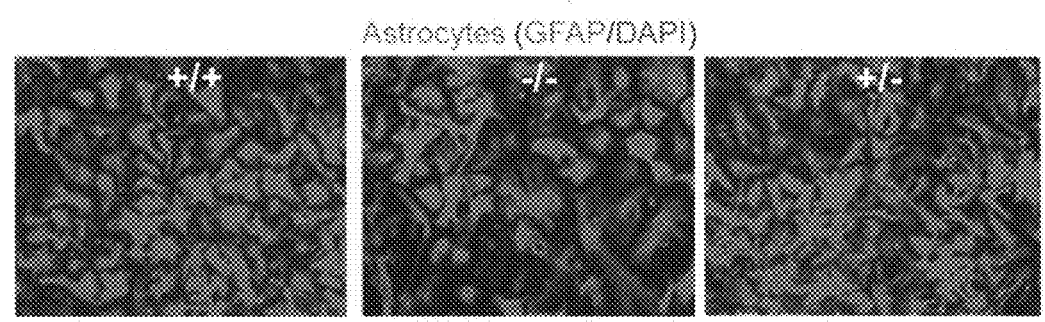
FIG. 40

FIG. 41A
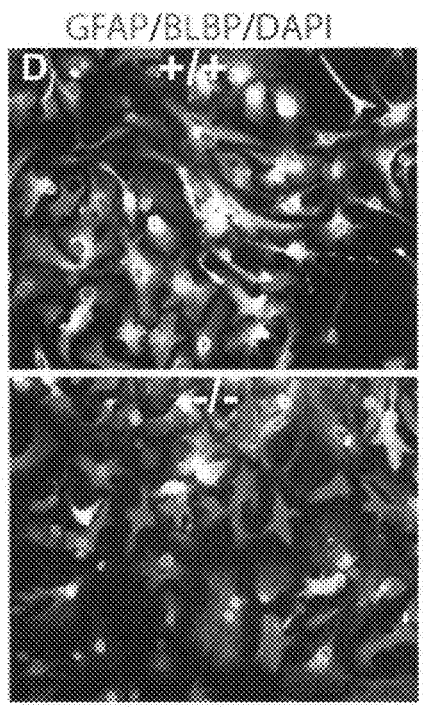
FIG. 41B
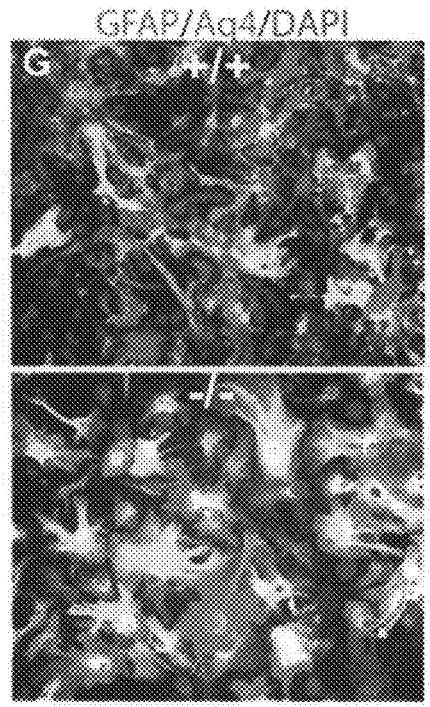
FIG. 41C
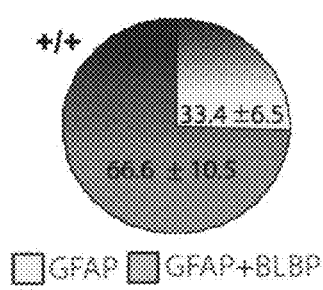
FIG. 41D
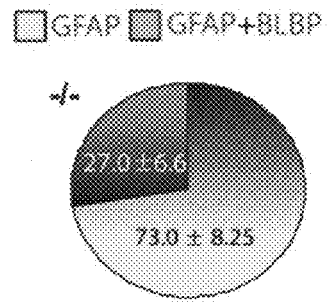
FIG. 41

FIG. 42A
Phase
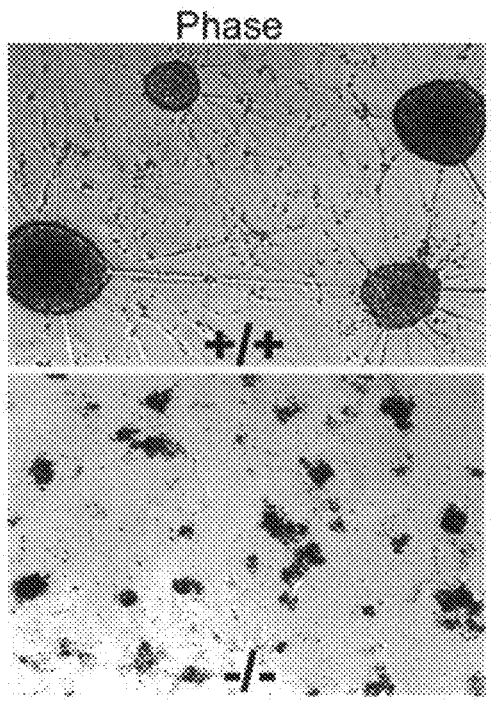
FIG. 42B
NeuN/cleaved Caspase3
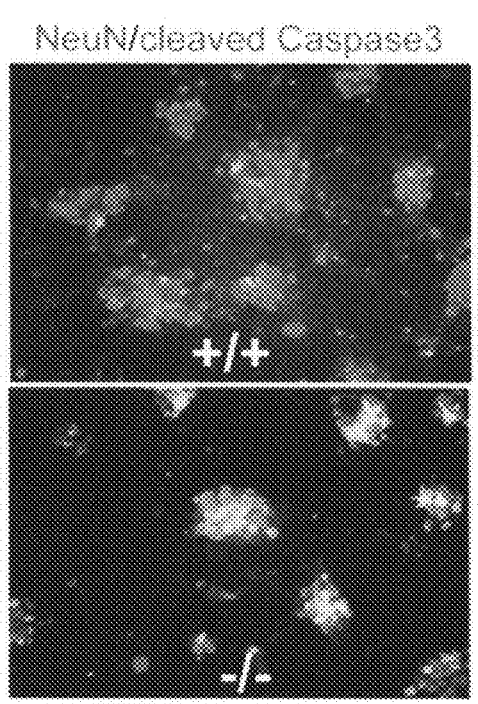
FIG. 42C
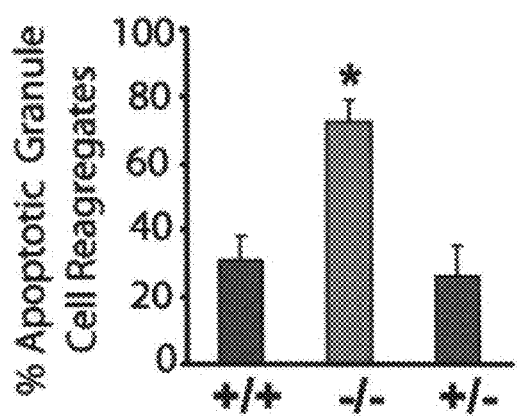
FIG. 42

FIG. 43A
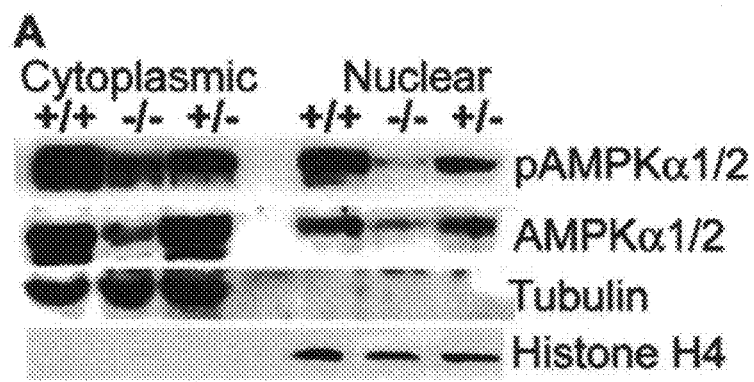
FIG. 43B
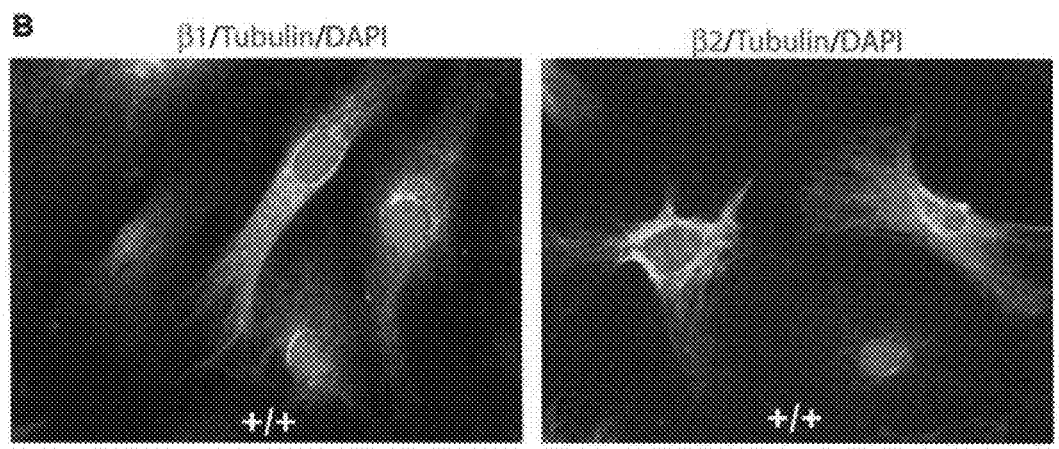
FIG. 43C
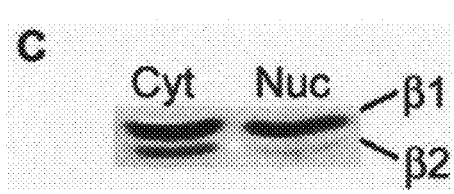
FIG. 43D
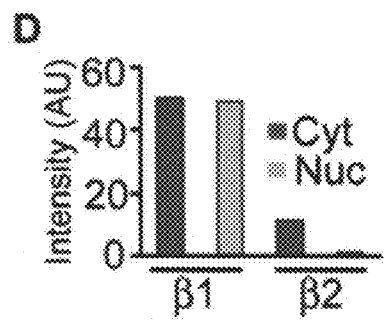
FIG. 43

FIG. 44A
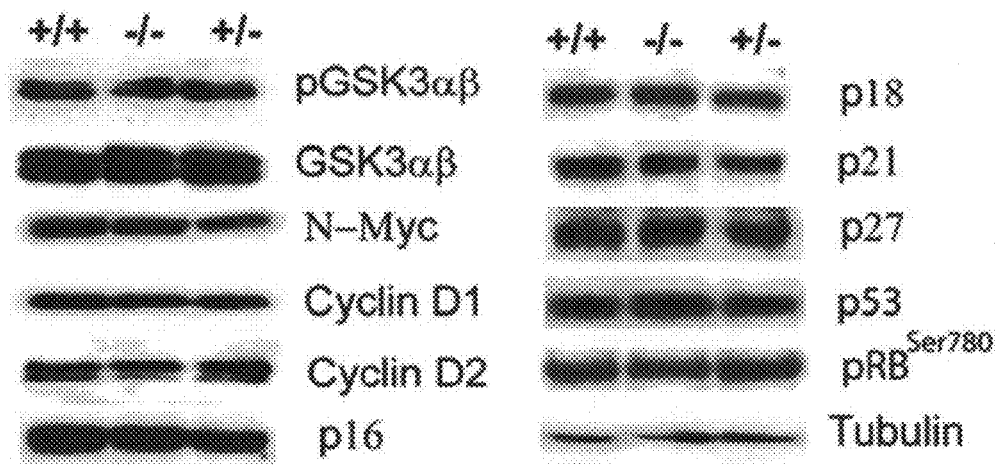
FIG. 44B
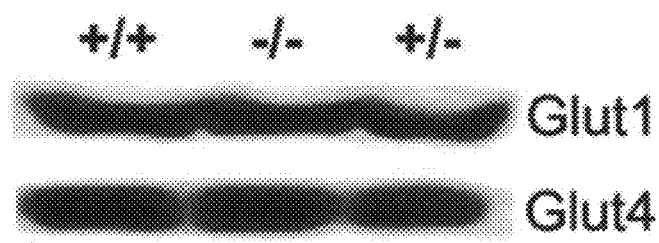
FIG. 44C
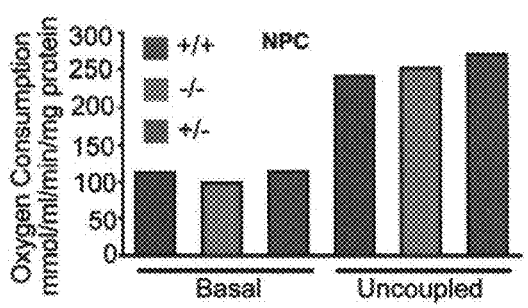
FIG. 44D
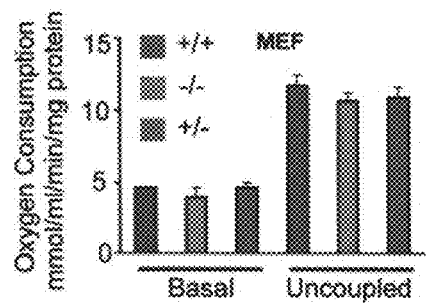
FIG. 44

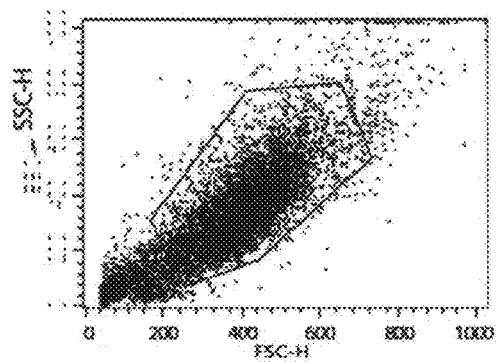
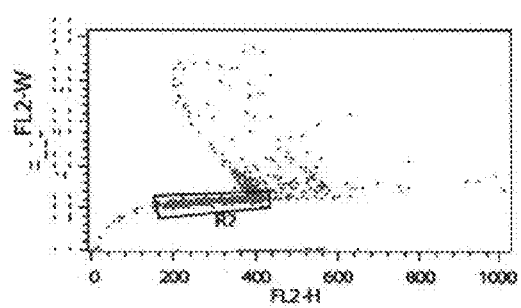
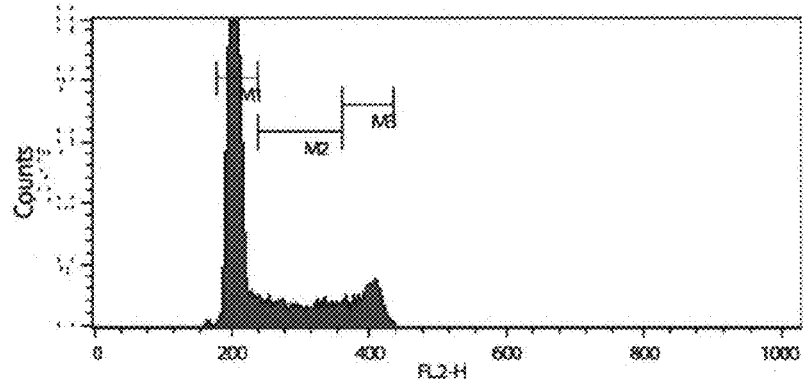
FIG. 45A
FIG. 45B
FIG. 45C
FIG. 45

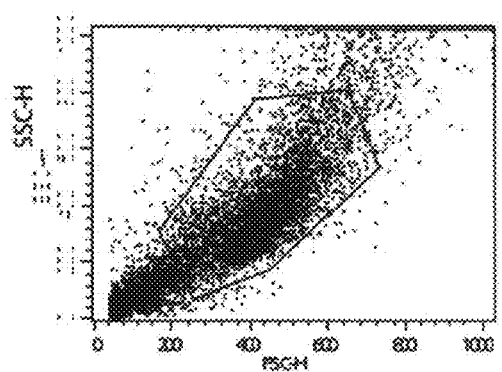
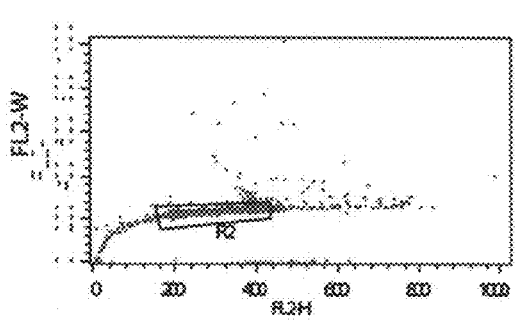
FIG. 46A
FIG. 46B
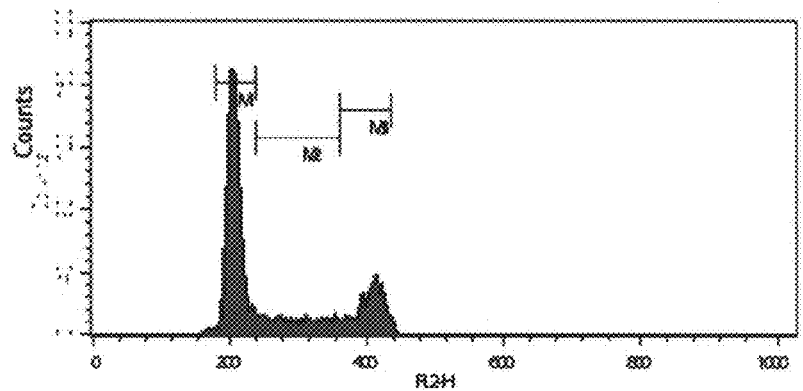
FIG. 46C
FIG. 46

FIG. 47A
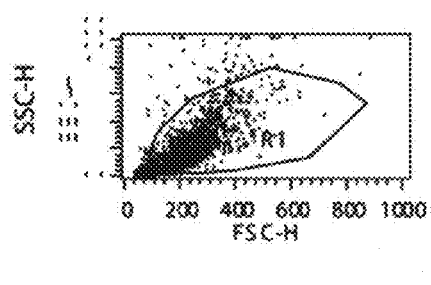
FIG. 47B
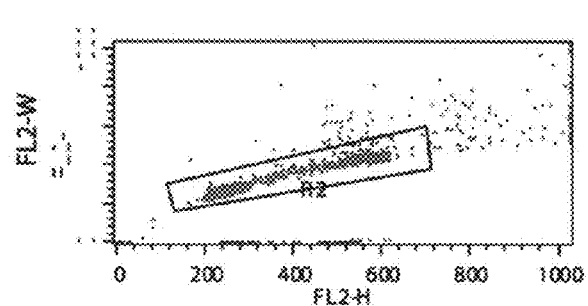
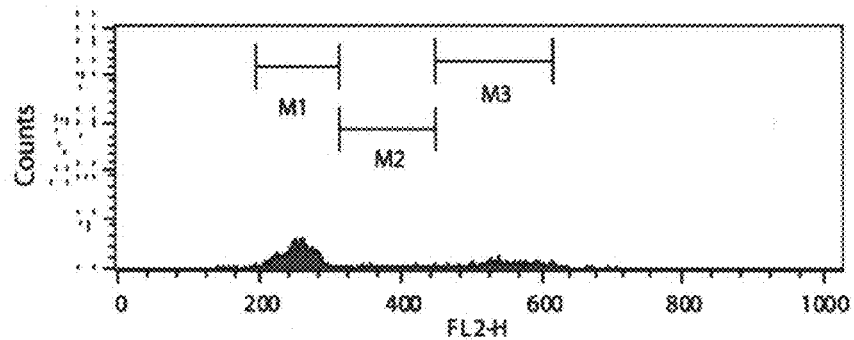
FIG. 47C
FIG. 47

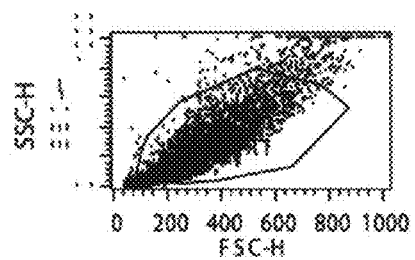
FIG. 48A
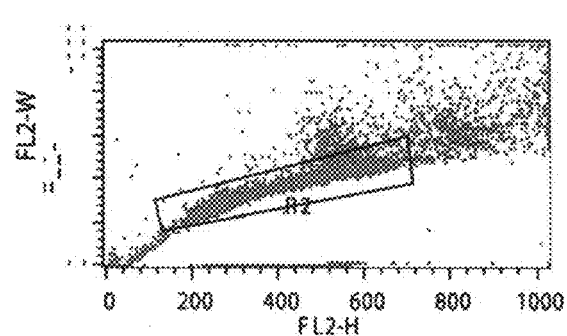
FIG. 48B
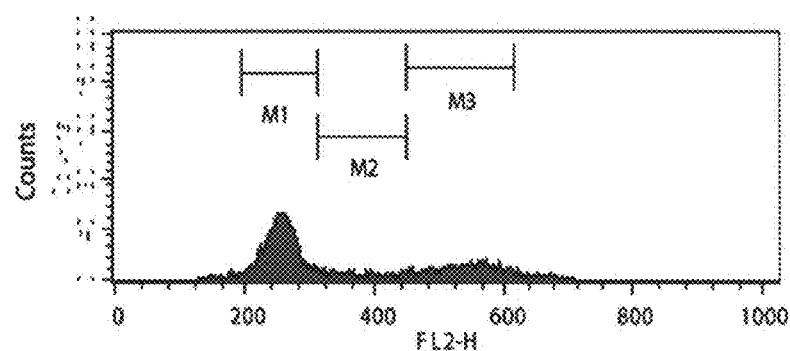
FIG. 48C
FIG. 48

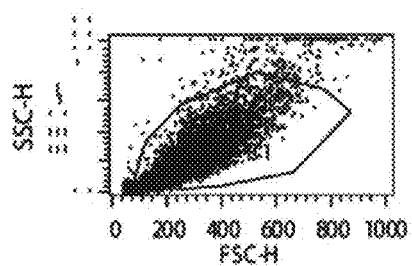
FIG. 49A
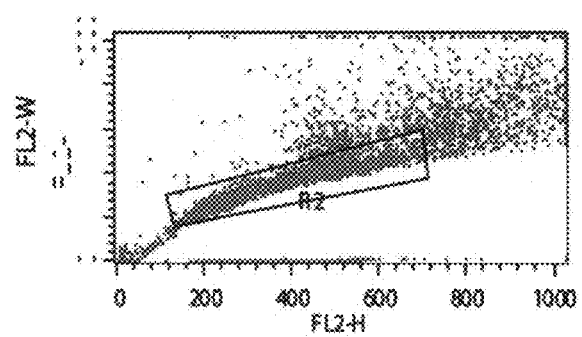
FIG. 49B
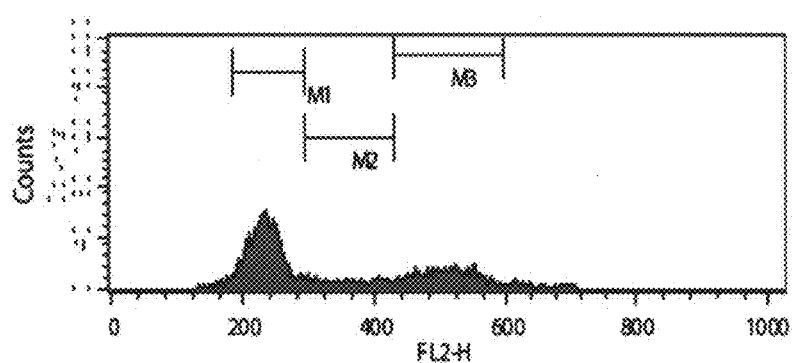
FIG. 49C
FIG. 49

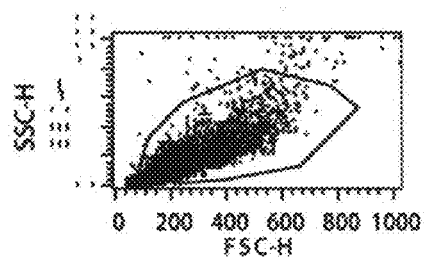
FIG. 51A
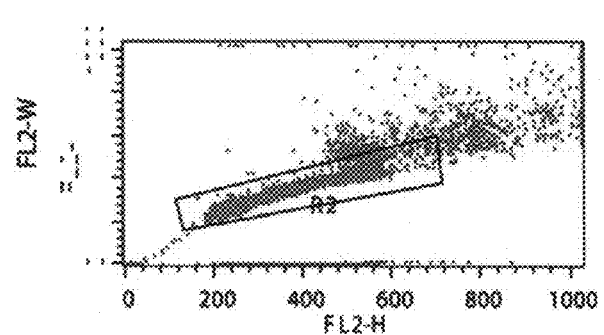
FIG. 51B
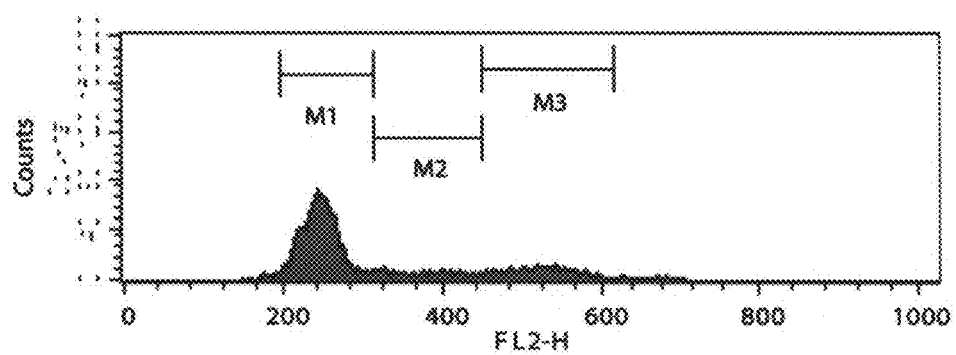
FIG. 51C
FIG. 51

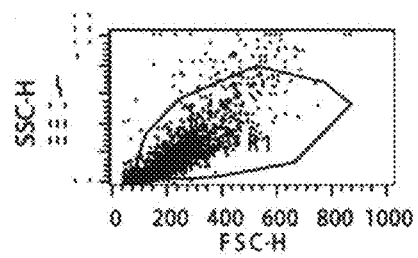
FIG. 52A
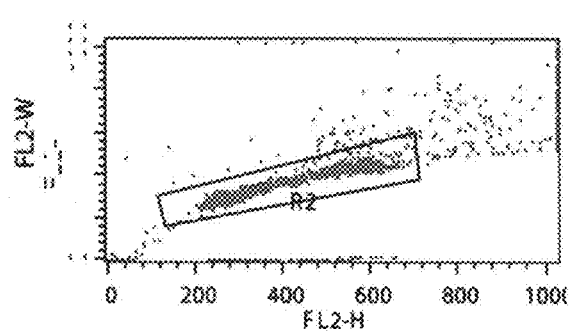
FIG. 52B
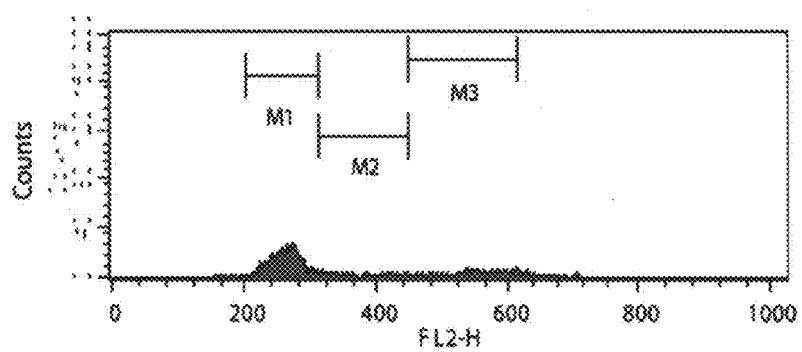
FIG. 52C
FIG. 52

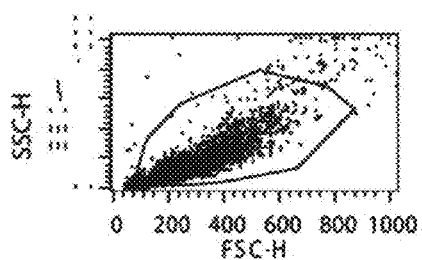
FIG. 53A
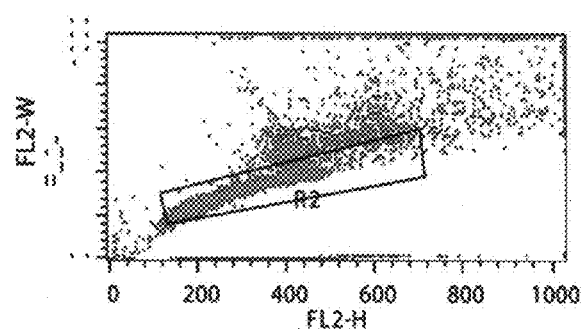
FIG. 53B
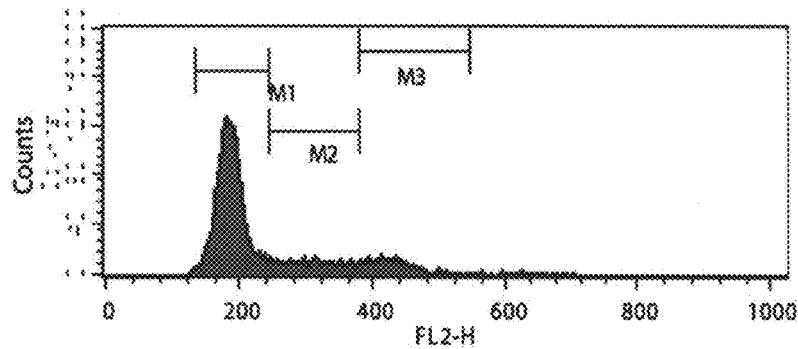
FIG. 53C
FIG. 53

FIG. 54A
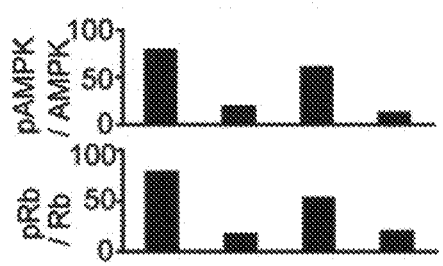
FIG. 54B
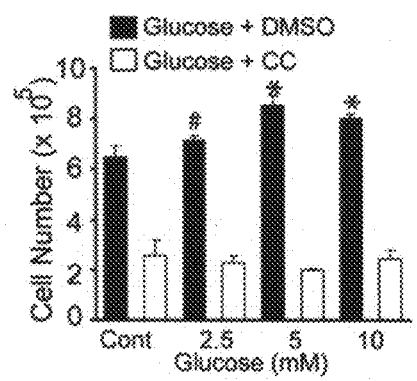
FIG. 54C
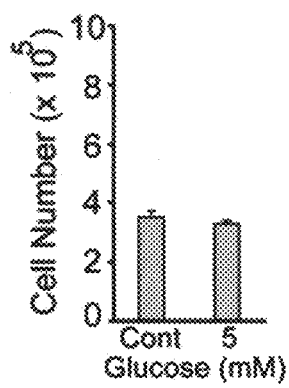
FIG. 54D
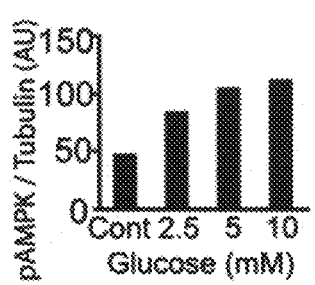
FIG. 54E
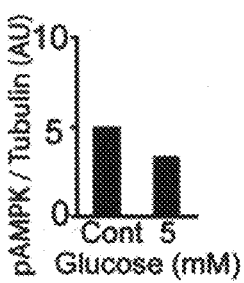
FIG. 54

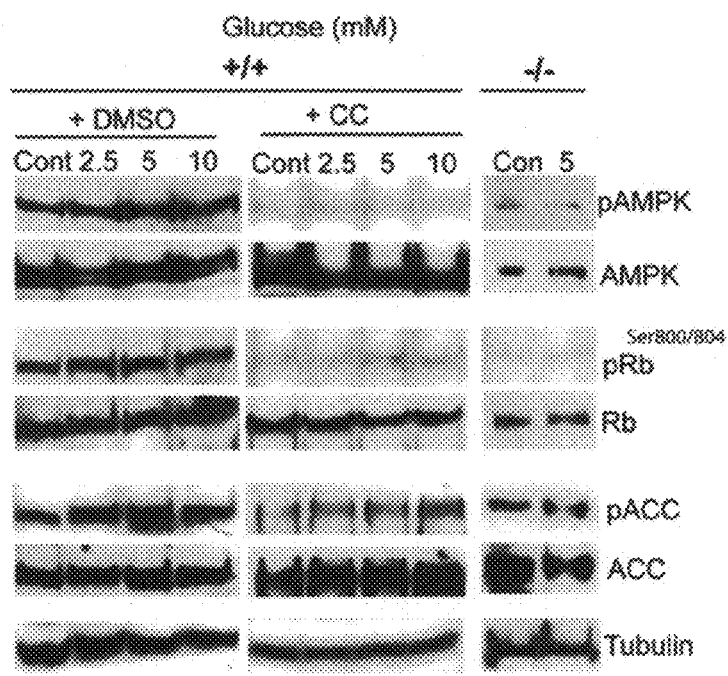
FIG. 55A
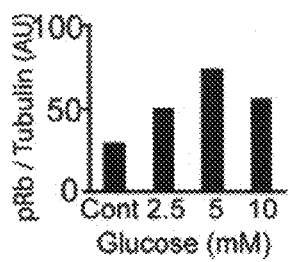
FIG. 55B
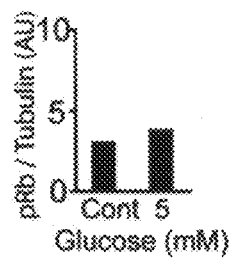
FIG. 55C
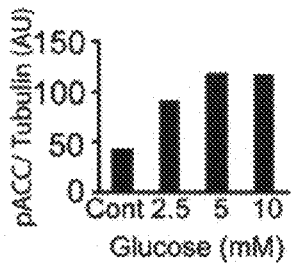
FIG. 55D
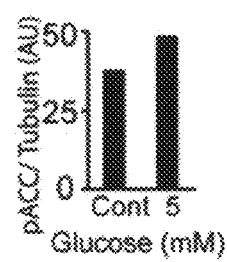
FIG. 55E
FIG. 55

FIG. 56A
FIG. 56B
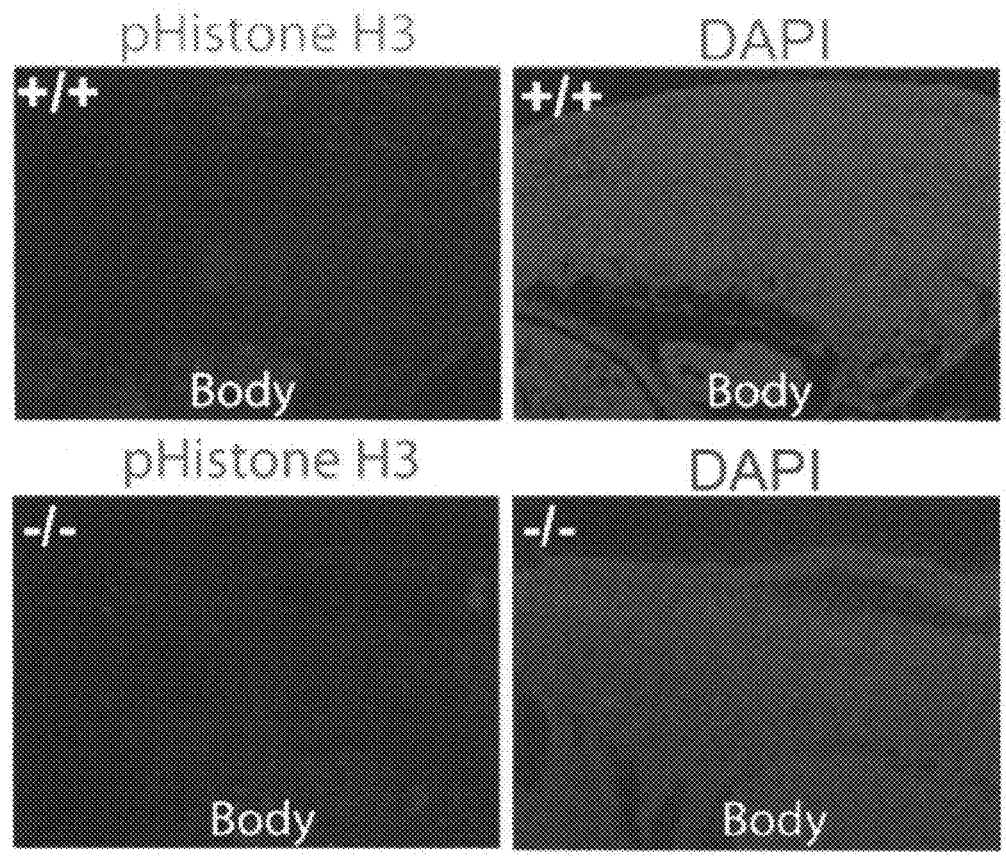
FIG. 56

FIG. 58A
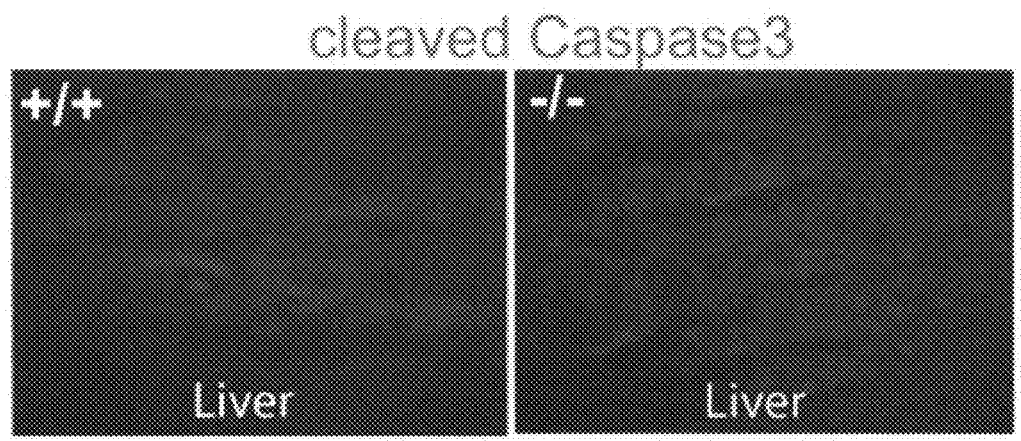
FIG. 58B
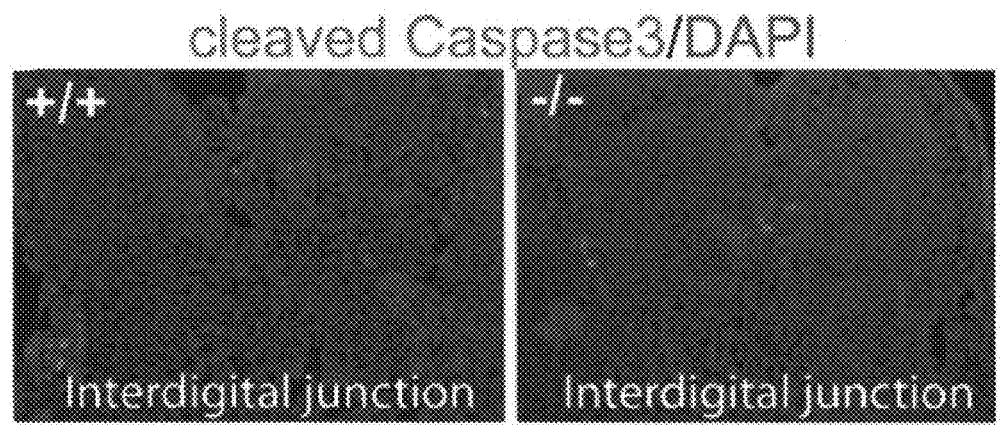
FIG. 58

FIG. 59A
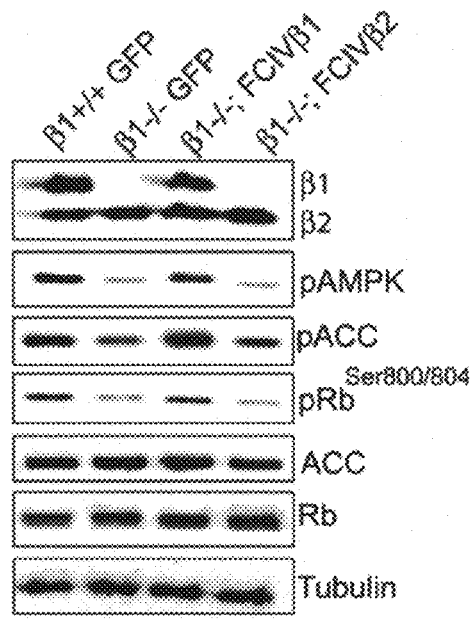
FIG. 59B
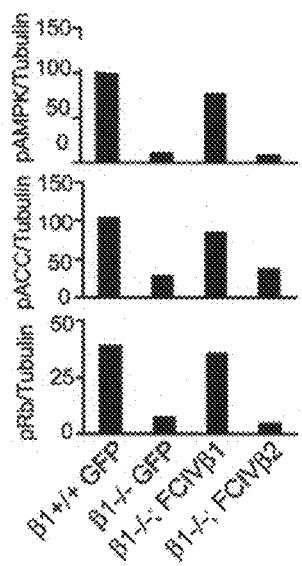
FIG. 59C
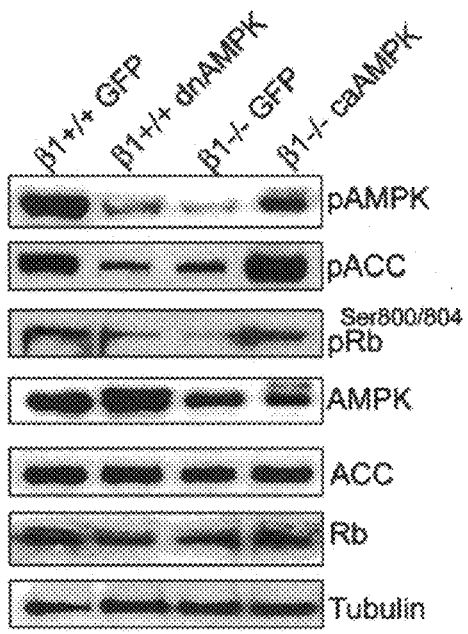
FIG. 59D
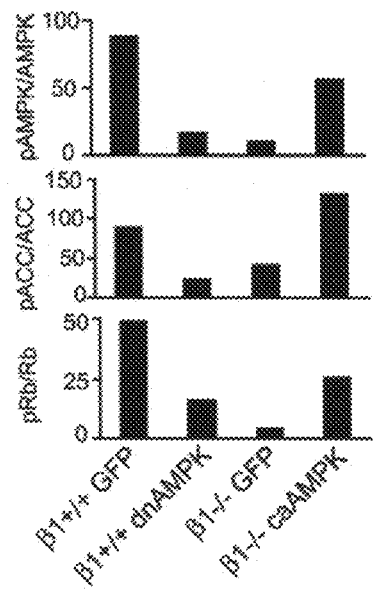
FIG. 59

SEQUENCE LISTING

<160> NUMBER OF SEQ ID NOS: 7

<210> SEQ ID NO 1
<211> LENGTH: 10
<212> TYPE: PRT
<213> ORGANISM: Mus musculus

<400> SEQUENCE: 1

Ile Ser Pro Leu Lys Ser Pro Tyr Lys Ile
1               5                   10

<210> SEQ ID NO 2
<211> LENGTH: 22
<212> TYPE: DNA
<213> ORGANISM: Artificial Sequence
<220> FEATURE:
<223> OTHER INFORMATION: primer

<400> SEQUENCE: 2
tgactgtggt cagcctgttc tc                                          22

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
cacaggacat aggatgtggc c                                           21

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
cagacaagta gatcccggcg ctc                                         23

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
ttgaacaagg acacgggcat ctc                                         23

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
gacagtatcg gcctcaggaa gatcg                                       25

```
<210> SEQ ID NO 7
<211> LENGTH: 10
<212> TYPE: PRT
<213> ORGANISM: Mus musculus

<400> SEQUENCE: 7

Met Arg Pro Ser Met Ser Gly Leu His Leu
1               5                   10
```

AMPK MODULATION AS A METHOD OF REGULATING STEM CELL AND CANCER STEM CELL PROLIFERATION, SELF-RENEWAL AND DIFFERENTIATION

CROSS-REFERENCE TO RELATED APPLICATIONS

This application claims the benefit of priority of U.S. Provisional Application Ser. No. 61/042,253, filed Apr. 3, 2008, which is incorporated herein by reference in its entirety.

GOVERNMENTAL INTEREST

The Invention was made with government support under U.S.P.H.S. Grants NAGO1 3730 and NS040745, awarded by the National Institutes of Health. The U.S. Government has certain rights in the invention.

INCORPORATION BY REFERENCE OF SEQUENCE LISTING SUBMITTED IN COMPUTER-READABLE FORM ON A COMPACT DISC

The Sequence Listing, which is a part of the present disclosure, includes a computer readable form submitted in duplicate on compact disc and a written sequence listing comprising nucleotide and/or amino acid sequences of the present invention. The sequence listing information recorded in computer readable form on compact disc is identical to the written sequence listing. The subject matter of the Sequence Listing is incorporated herein by reference in its entirety.

The CDs are PC-formatted. They were created using MS-Windows. Each CD contains one file, each named "60005161_0389_seq_listing_Apr2009_ST25.txt". Each of these files is 2 KB, and was created on Apr. 3, 2009.

INTRODUCTION

AMP activated protein kinase (AMPK) is an integrative metabolic sensor that maintains energy balance both at the cellular and systemic level. It links neuronal functions with energy supply and plays a key role in hypothalamic control of food intake and peripheral energy expenditure (Xue, B. & Kahn, B. B., J. Physiol. 574, 73-83, 2006). Systemic AMPK activity is linked to human diseases such as diabetes, obesity, stroke, hypertension, myocardial injury and atherosclerosis, and may be involved in the protection afforded by caloric restriction (Claret, M., et al., J. Clin. Invest. 117, 2325-2336, 2007; Miller, E. J., et al., Nature 451, 578-582, 2008; Dyck, J. R., Circulation 116, 2779-2781, 2007). One important neuronal target of AMPK is the $GABA_B$ receptor, whose activation helps mediate neuroprotection after ischemia (Kuramoto, N., et al., Neuron 52, 233-247, 2007).

In addition to its metabolic functions, studies in model organisms suggest that AMPK also regulates cell structure and polarity, cell division, as well as normal growth and development (Lee J. H., et al., Nature 447, 1017-1020, 2007; Baena-González E., et al., Nature 448, 938-942, 2007). In particular, AMPK helps maintain genomic integrity in neural precursors as well as the structure and function of mature neurons in Drosophila (Lee J. H., et al., Nature 447, 1017-1020, 2007). Loss of AMPK activity causes neurodegeneration in Drosophila (Tschäpe, J. A., et al., EMBO J. 21, 6367-6376, 2002). and AMPK activation in mice protects hippocampal neurons against metabolic, excitotoxic and oxidative insults (Culmsee, C., et al., J. Mol. Neurosci. 17, 45-58, 2001). These studies have suggested that AMPK may have additional roles beyond the established metabolic functions both in normal physiology and disease.

AMPK is a heterotrimeric, multisubstrate kinase composed of one catalytic ($\alpha1$ or $\alpha2$), one regulatory ($\beta1$ or $\beta2$), and one AMP/ATP binding ($\gamma1$, $\gamma2$, or $\gamma3$) subunit. The C terminus of the $\beta$ subunit interacts with both $\alpha$ and $\gamma$ subunits, and current biochemical and structural evidence indicate that the $\beta$ subunit is an obligatory component of the active AMPK complex. When intracellular energy levels drop (low ATP:AMP ratio), AMP displaces ATP from the $\gamma$ subunit, causing a conformational change that allows upstream kinases (e.g., LKB1 or CaMKK$\beta$) to phosphorylate and activate the $\alpha$ subunit. In addition to uniting the $\alpha$ and $\gamma$ subunits, in yeast the $\beta$ subunits also serve regulatory functions, as they direct the AMPK complex to defined substrates in specific subcellular compartments (Vincent et al., Genes Dev. 15, 1104-1114, 2001). AMPK is required for adaptation of nutrient-deprived cancer cells to hypoxia (Yun, H., et al., J. Biol. Chem. 280, 9963-9972, 2005; Laderoute, K. R., et al., Mol. Cell. Biol. 26, 5336-5347, 2006; Nagata, D., et al., J. Biol. Chem. 278, 31000-31006, 2003) and loss of AMPK activation sensitizes cancer cells to apoptosis (Kim, H. S., et al., J. Biol. Chem. 283, 3731-42, 2007; Baumann, P., et al., Anti-cancer Drugs, 18, 405-10, 2007).

The analysis of mice lacking AMPK $\alpha1$ or $-\alpha2$ catalytic subunits has demonstrated the widespread and overlapping functions of these proteins, and the importance of overall AMPK activity (Jorgensen et al., Mol. Cell. 18, 283-293, 2005). Human mutations of the $\gamma2$ subunit cause cardiomyopathy, characterized by hypertrophy and glycogen accumulation (Blair et al., Hum. Mol. Genet. 10, 1215-1220, 2001), whereas characterization of mice lacking $\gamma3$ subunit has demonstrated impaired postexercise glycogen resynthesis in skeletal muscle (Barnes et al., J. Biol. Chem. 279, 38441-38447, 2004). In contrast to studies of these subunits, little is known about the physiologic roles of individual $\beta$ subunits in mammals. Interestingly, loss of AMPK$\beta$ subunit in Drosophila causes progressive neurodegeneration, indicating a crucial role in adult neuron maintenance (Spasic et al., J. Neurosci. 28, 6419-6429, 2008).

Rb phosphorylation is a defining regulatory event in early G1, a period when external cues (growth factors and morphogens) mediate cell fate decisions; in particular, the decision to exit cell cycle and the commitment to undergo differentiation (Sherr, C. J., Cancer Res. 60, 3689-3695, 2000; Massague, J., Nature 432, 298-306, 2004; Orford, K. W., & Scadden, D. T., Nat. Rev. Genet. 9, 115-128, 2008). Data concerning Rb phosphorylation in NPCs is scanty; however, it is noteworthy that most mouse cells lacking two or even three CDKs proliferate (Malumbres, M., et al., Cell 118, 493-504, 2004; Berthet, C., et al., Dev. Cell 10, 563-73, 2006; Barriere, C., et al., Mol. Oncology. 1, 72-83, 2007) and contain residual phosphorylated Rb.

SUMMARY

In some aspects, the present inventors provide methods of treating a cancer. These methods comprise administering to a subject in need of treatment an inhibitor of AMPK activity. In some configurations, an inhibitor of AMPK activity can be administered in an amount effective to decrease proliferation of cancer stem cells. In some configurations, the cancer stem cells can be neural cancer stem cells. In some configurations, the methods can further comprise administering to the subject a cancer therapy such as a cancer chemotherapy, a cancer radiation therapy, or a combination thereof.

In further aspects, the present inventors provide methods of treating a cancer. In various configurations, these methods comprise administering to a subject in need of treatment an inhibitor of AMPK activity in an amount effective to enhance apoptosis in cancer stem cells. In further aspects, these methods can further comprise administering to the subject a cancer therapy such as a cancer chemotherapy, a cancer radiation therapy, or a combination thereof.

In further aspects, the present inventors provide methods of treating a cancer, comprising administering an inhibitor of AMPK activity in an amount effective to induce a cancer stem cell to differentiate into a specialized cell type. The inhibitor of AMPK activity can be administered to a subject in need of treatment. In some configurations, the stem cells can comprise neural cancer stem cells, and the specialized cell type can be an oligodendrocyte.

In n additional aspects, the present inventors provide methods of inducing selective differentiation of a stem cell. These methods comprise contacting a stem cell with an AMPK inhibitor. In various configurations, the stem cell can be a neural stem cell and/or a cancer stem cell such as a neural cancer stem cell.

In the various aspects, an AMPK inhibitor can be any AMPK inhibitor known to skilled artisans, such as, without limitation, Compound C (6-[4-(2-piperidin-1-ylethoxy)-phenyl]-3-pyridin-4-ylpyrazolo[1,5-α]pyrimidine) or Adenine 9-β-D-arabinofuranoside A (Ara A).

In further aspects, the present inventors provide methods of treating a neural deficiency, disease or disorder of neural function in a subject in need thereof. In various configurations, these method can comprise administering to the subject an activator of AMPK activity. The neural deficiency, disease or disorder of neural function can be, for example, a deficiency, disease or disorder resulting from spinal cord injury, brain trauma injury, a deficiency in cognitive ability, a neurodegenerative disease, a deficiency in memory, a demyelinating disease, a dysmyelinating disease, or a hereditary metabolic disorder affecting myelination. The neurodegenerative disease can be, without limitation, Alzheimer's disease, Parkinson's disease, ALS or multiple sclerosis. In some configurations, a neural deficiency can be an irradiation-induced deficiency, a chemotherapy-induced deficiency, an ischemia-induced deficiency, a brain trauma-induced deficiency, a premature birth-induced deficiency, a nutritional deprivation-induced deficiency, or a combination thereof.

In further aspects, the present inventors provide an AMPK activator that is administered in an amount effective to stimulate formation of oligodendrocytes and/or differentiation of oligodendrocytes.

In yet further aspects, the present inventors provide methods of expanding a neural stem cell population. In some configurations, the neural stem cell population can be comprised by a subject such as a human subject. In various configurations, these methods can include administering to the subject an activator of AMPK activity. In various configurations, administration of an AMPK activator can comprise administering a proliferation-enhancing amount of an activator of AMPK activity, administering a self-renewal-enhancing amount of an activator of AMPK activity, and/or administering an apoptosis-suppressing amount of an activator of AMPK activity.

In yet additional aspects, the present inventors provide methods of expanding a neural stem cell population in vitro. In various configurations, these methods comprise contacting a cell culture comprising at least one neural stem cell with an AMPK activator. In some configurations, contacting a cell culture with an AMPK activator can comprise contacting the culture with the AMPK activator in an amount effective for increasing proliferation of a neural stem cell. In some other configurations, contacting a cell culture with an AMPK activator can comprise contacting the culture with the AMPK activator in an amount effective for enhancing self-renewal of the at least one neural stem cell. Contacting a cell culture with an AMPK activator can alternatively comprise contacting the culture with an AMPK activator in an amount effective for decreasing neural stem cell apoptosis.

The present inventors additionally provide cell-based therapeutic methods for treating a neural deficiency, disease or disorder of neural function. In various aspects, these methods can comprise expanding a neural stem cell population in vitro. These methods can further comprise administering neural stem cells of the expanded population to a subject in need of treatment. In some configurations, the neural stem cells can be autologous to the subject.

The present inventors further provide methods of expanding a cancer stem cell population in vitro. In some configurations, these methods can comprise contacting a cancer stem cell with an AMPK activator. These methods can increase proliferation of the cancer stem cells. In other configurations, these methods can comprise contacting a cancer stem cell with an AMPK activator in an amount effective for enhancing self-renewal of the cancer stem cells. In still other configurations, these methods can comprise contacting a cancer stem cell with an AMPK activator in an amount effective for decreasing apoptosis cancer stem cells.

In a further embodiment, the present inventors provide methods of screening a chemotherapeutic compound. In some aspects, these methods can comprise expanding a cancer stem cell population in vitro. In further aspects, these methods can further comprise contacting an expanded cancer stem cell population with a candidate chemotherapeutic agent. In yet further aspect, these methods can further comprise determining the effectiveness of the candidate chemotherapeutic agent.

In a further aspect, the present inventors provide methods for inducing selective differentiation in a stem cell. The method can comprise contacting the stem cell with an AMPK activator. In some aspects, the AMPK activator can be metformin or 5-Aminoimidazole-4-carboxamide-1-beta-d-ribofuranoside (AICAR).

In an additional aspect, the present inventors provide methods for screening a compound for activity as an AMPK activator. In some configurations, these methods can comprise providing cells expressing both AMPK and a polypeptide comprising an Rb phosphorylation site. The methods can comprise contacting the cells with a candidate compound. The methods can comprise detecting an increase in phosphorylation of an Rb phosphorylation site. In one configuration, the cells can be neural precursor cells and the peptide comprising an Rb phosphorylation site can comprise the amino acid sequence ISPLKSPYKI (SEQ ID NO. 1). In some configurations, the detecting can comprise detecting the presence, absence or quantity of binding of an antibody directed against a phosphorylated Rb phosphorylation site. In other configurations, the detecting can comprise adding to the cell culture one or more radiolabelled ATP, wherein the detecting comprises detecting the presence, absence or quantity of radiolabel incorporated into the polypeptide.

In a further aspect, the present inventors provide methods for screening a compound for activity as an AMPK activator. In some aspects, these methods can comprise forming a mixture comprising AMPK and a polypeptide comprising an Rb phosphorylation site. The methods can comprise contacting the mixture with a candidate compound. The methods can comprise detecting an increase in phosphorylation of the Rb phosphorylation site. In one configuration, the mixture can comprise a bacterial lysate comprising the polypeptide comprising an Rb phosphorylation site. In some configurations, the peptide comprising an Rb phosphorylation site can comprise the amino acid sequence ISPLKSPYKI (SEQ ID NO. 1). In some configurations, the detecting can comprise detecting the presence, absence or quantity of binding of an antibody directed against a phosphorylated Rb phosphorylation site. In other configurations, the detecting can comprise adding to the cell culture one or more radiolabelled ATP, wherein the detecting comprises detecting the presence, absence or quantity of radiolabel incorporated into the polypeptide.

In an additional aspect, the present inventors provide methods for screening a compound for activity as an AMPK inhibitor. In one configuration, these methods can comprise providing cells expressing both AMPK and a polypeptide comprising an Rb phosphorylation site. These methods can comprise contacting the cells with a candidate compound. These methods can comprise detecting a decrease in phosphorylation of the Rb phosphorylation site. In some configurations, the cells can be neural precursor cells. In some configurations, the peptide comprising an Rb phosphorylation site can comprise the amino acid sequence ISPLKSPYKI (SEQ ID NO. 1). In some configurations, the detecting can comprise detecting the presence, absence or quantity of binding of an antibody directed against a phosphorylated Rb phosphorylation site. In other configurations, the detecting can comprise adding to the cell culture one or more radiolabelled ATP, wherein the detecting comprises detecting the presence, absence or quantity of radiolabel incorporated into the polypeptide.

In a further aspect, the present inventors provide methods for screening a compound for activity as an AMPK inhibitor. In some aspects, these methods can comprise forming a mixture comprising AMPK and a polypeptide comprising an Rb phosphorylation site. The methods can comprise contacting the mixture with a candidate compound. The methods can comprise detecting an decrease in phosphorylation of the Rb phosphorylation site. In one configuration, the mixture can comprise a bacterial lysate comprising the polypeptide comprising an Rb phosphorylation site. In some configurations, the peptide comprising an Rb phosphorylation site can comprise the amino acid sequence ISPLKSPYKI (SEQ ID NO. 1). In some configurations, the detecting can comprise detecting the presence, absence or quantity of binding of an antibody directed against a phosphorylated Rb phosphorylation site. In other configurations, the detecting can comprise adding to the cell culture one or more radiolabelled ATP, wherein the detecting comprises detecting the presence, absence or quantity of radiolabel incorporated into the polypeptide.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1. This figure illustrates that AMPK activity is reduced in AMPKβ1-deficient mice.

FIG. 2. This figure illustrates that AMPKβ1-deficient mice show reduced AMPK activity and manifest brain abnormalities.

FIG. 3. This figure illustrates that AMPKβ1-deficient mice manifest brain abnormalities.

FIG. 4. This figure illustrates that AMPKβ1-deficient mice manifest brain abnormalities.

FIG. 6. This figure illustrates that AMPKβ1-deficient mice demonstrate both neuronal and glial CN deficits.

FIG. 7. This figure illustrates that AMPKβ1-deficient mice demonstrate both neuronal and glial CN deficits.

FIG. 8. This figure illustrates that AMPKβ1-deficient mice demonstrate both neuronal and glial CN deficits and seizures.

FIG. 9. This figure illustrates that AMPKβ1-deficient mice demonstrate reduced GABA receptor phosphorylation.

FIG. 10. This figure illustrates immunohistochemistry of the E14.5 forebrain with antibodies against Ki67 (red in FIG. 10A, FIG. 10B), BrdU (green in FIG. 10B), phosphohistone H3 (red in FIG. 10C) and shows that loss of β1 results in neural stem/progenitor cell developmental defects.

FIG. 11. This figure illustrates unregulated apoptosis in E14.5 embryos.

FIG. 12. This figure illustrates that loss of β1 results in neural stem/progenitor cell developmental defects.

FIG. 13. This figure illustrates that loss of β1 results in neural stem/progenitor cell developmental defects.

FIG. 14. This figure illustrates lack of cell death in the astrocyte population at P7.

FIG. 15. This figure illustrates that AMPKβ1 loss results in cell-autonomous NPC defects.

FIG. 16. This figure illustrates that AMPKβ1 loss results in cell-autonomous NPC defects.

FIG. 17. This figure illustrates that AMPKβ1 loss results in cell-autonomous NPC defects and that Expression of β1, but not β2, rescues β1−/− NPC phenotypes.

FIG. 18. This figure illustrates subcellular localization of β1 and β2 subunits.

FIG. 19. This figure illustrates that expression of β1, but not β2, rescues β1−/− NPC phenotypes.

FIG. 24. This figure illustrates that AMPK phosphorylates Rb to regulate Rb-E2F interaction. (A) Nonradioactive kinase assay: CDK4/6 complex immunoprecipitated using cyclin D1/D2 antibodies from WT and β1−/− NPCs. (B) Proliferation assay of WT and β1−/− NPCs expressing GFP or the indicated Rb proteins. Data are representative of two independent experiments; *p<0.005. Error bars indicate SD. (C) Flow cytometric analysis of NPCs expressing GFP or Rb proteins displaying the percentage of cells in G2M phase. FACS data are available in FIGS. 45-53.

FIG. 26. Pharmacologic Inhibition of AMPK drastically reduces proliferation of Neural Stem and Progenitor cells (NPCs). Embryonic day 12.5 forebrain wildtype NPCs were cultured for 4 days and seeded as single cells in presence of DMSO (control), or the AMPK inhibitors Compound C (10 μM) and Adenine 9-β-D-arabinofuranoside (Ara A 1 mM). Following 48 hours of growth in medium supplemented with EGF (10 μM) and bFGF (10 μM), neurospheres were trypsinized and trypan blue negative (live) cells were counted on a hemocytometer. * p<0.001

FIG. 27. This figure illustrates characterization of β1 Mutant Allele and β1−/− Mice (A) Schematic of the β-geo gene trap present in Bay Genomics ES cell (RRR454). Arrows indicate positions of primers used for PCR genotyping and RT-PCR (SA=splice acceptor; PA=poly A sequence). (B) Representative PCR genotyping assay of tail DNA from β1+/+ (wildtype), β1−/− and β1+/− mice. (C) Southern blot analysis of tail DNA from two β1+/− animals hybridized with a probe derived from β-geo. Note the presence of a single band indicating only one insertion site in this ES cell line. (D) RT-PCR amplification of the β1-βgeo fusion transcript using primers a and b SEQ ID NOs.: 2-4).

FIG. 28. This figure illustrates characterization of β1 Mutant Allele and β1−/− Mice (A) Immunoblot analysis of tissues from wildtype and β1−/− mice using β-gal antibody to detect the β1-βgal fusion protein. (B) Lysates from MEFs prepared from β1−/− mice were analyzed by immunoblot using β1/β2 C-terminal-specific antibody. Note the absence of β1 in MEFs derived from mice homozygous for the β1 mutant allele. (C) Immunohistochemical analysis of E14.5 brain from β1−/− mice was performed using phospho-specific AMPKα1/2$^{Thr172}$ antibodies.

FIG. 29. This figure illustrates characterization of β1 Mutant Allele and β1−/− Mice (A) Immunohistochemical analysis of E14.5 brain from β1−/− mice was performed using phospho-specific ACC$^{Ser79}$ antibodies. (I) Presence of nuclear phospho (active) AMPK (punctate appearance) in wild-type brain. Nuclei were counterstained with DAPI.

FIG. 30. This figure illustrates that AMPKβ1−/− mice are small, unhealthy and die perinatally. (A) Photograph of wild-type (+/+) and AMPKβ1−/− mice at P14. (B) Growth curve of wt (+/+), β1−/− and β1+/− mice. Error bars indicate SD.

FIG. 31. This figure illustrates oligodendroglial deficits in the CNS of β1−/− Mice (A) Quantification of brain area, showing reduced brain size of P14 β1−/− mice (n=6). (B) Immunohistochemical analysis of the indicated brain regions from wildtype and β1−/− mice using APC antibodies to detect oligodendrocytes. Counting of APC-positive cells revealed a 75-80% loss of oligodendrocytes in all brain regions examined.

FIG. 32. This figure illustrates oligodendroglial deficits in the CNS of β1−/− Mice (A) Immunohistochemistry of the striatum in wildtype and β1−/− mice using myelin basic protein (MBP) antibody to highlight myelinated fibers. (B) Light microscopic analysis of P14 optic nerves from wild-type and β1−/− mice. * p<0.005; # p<0.05. Error bars indicate SD.

FIG. 34. This figure illustrates astroglial phenotype in the CNS of β1−/− Mice. Immunohistochemistry of the hippocampal region of P14 wildtype and β1−/− brain using GFAP and BLBP antibodies.

FIG. 35. This figure illustrates developmental analysis of β1−/− mice. (A and C) Photographs and body weights of wildtype, β1+/−, and β1−/− E18.5 embryos. (B and D) Photographs of brains and sizes of the indicated brain regions from wildtype, β1+/− and β1−/− E18.5 embryos.

FIG. 36. This figure illustrates developmental analysis of β1−/− mice. (A and B) Immunohistochemical analysis of P7 dentate gyrus (A) and P7 cerebellum (B) using phosphohistone H3 antibody (red) to detect mitotic cells. (C) Quantitative analysis of mitotic cells in the indicated brain regions.

FIG. 37. This figure illustrates developmental analysis of β1−/− mice. (A) Immunohistochemistry with cleaved Caspase3 antibody (red) to detect apoptotic cells in the P7 cerebellum. (B) Quantitative analysis of apoptotic Olig2+ cells in the E18.5 brain.

FIG. 38. This figure illustrates developmental analysis of β1−/− mice. Immunohistochemistry of P14 wildtype and β1−/− brains using PAR3 antibody (A), and immunocytochemistry of cultured embryonic neurons using PAR3 (B) and phospho-PKCξ (C) antibodies. DAPI staining (blue) was used to highlight the nuclei.

FIG. 39. This figure illustrates that cell-intrinsic deficits cause reduced proliferation of β1−/− NPCs. (A) NPCs were isolated from telencephalon of wild-type or β1−/− embryos, cultured, and the diameter (measure of cell growth) of the derived neurospheres was determined. (B) The number of cells generated from primary, secondary and tertiary neurospheres during NPC growth assays was determined. * p<0.001. Error bars indicate SD. (C-D) Lysates of NPCs were analyzed by immunoblot using phospho-specific and pan Erk1/2 (C) and Akt antibodies (D).

FIG. 40. This figure illustrates normal expression of many cell cycle regulators in β1−/−NPCs. (A-C) Immunocytochemical analysis of neurospheres derived from wild-type, β1+/− and β1−/− mice using Tuj1 (red), O4 (red) and GFAP (green) antibodies to detect neurospherederived neurons, oligodendrocytes and astrocytes, respectively.

FIG. 41. This figure illustrates that differentiation defects of β1−/− NPCs are caused by cell-intrinsic mechanisms. (A) Quantification of immunohistochemical results in (A-C) for each cell population. (B) Immunocytochemical analysis of neurosphere-derived astrocytes from wildtype and β1−/− embryos using BLBP (red) and GFAP (green) antibodies. (C) Immunocytochemical analysis of neurosphere-derived astrocytes from wild-type and β1−/−embryos using Aquaporin4 (red) and GFAP (green) antibodies. Nuclei were counterstained with DAPI (blue). (D and E) Quantification of immunohistochemical results in (B).

FIG. 42. This figure illustrates cell-intrinsic defects of β1−/− granule cell neurons. (A) Phase contrast microscopy of β1−/− granule cell neurons cultured from P2 cerebellum demonstrated a failure to form reaggregates and extend neurites. (B) Immunocytochemistry using NeuN (green) and cleaved Caspase3 (red) antibodies showed enhanced apoptosis of NeuN+ β1−/− granule cell neurons. (C) Quantification of apoptotic granule cell reaggregates of indicated genotypes. * p<0.001. Error bars indicate SD.

FIG. 43. This figure illustrates that the β1 subunit primarily regulates nuclear AMPK activity in NPCs. (A) Immunoblot of cytoplasmic and nuclear lysates of NPCs using pAMPKα1/2$^{Thr172}$ and pan AMPKα1/2 antibodies. The lysates were also probed with anti-tubulin and antihistone H4 antibodies to verify the purity of nuclear and cytoplasmic fractions. (B) Immunocytochemistry of wildtype MEFs using β1 and β2 N-terminal-specific antibodies (red), acetylated tubulin antibody (green) to delineate the cytoskeleton, and DAPI (blue) to highlight the nucleus. Note that β1 is present throughout the cell, whereas β2 is primarily cytoplasmic. (C) Immunoblot analysis of nuclear and cytoplasmic fractions of wildtype NPCs using the β1/β2 C-terminal-specific antibody.

(D) Densitometry was used to quantify the amount of β1 and β2 in the nuclear and cytoplasmic compartments. AU=arbitrary units.

FIG. 44. This figure illustrates normal expression of many cell cycle regulators in β1−/−NPCs. (A) Immunoblot analysis of wildtype, β1−/− and β1+/− NPCs using antibodies against phosphoGSK3αβ$^{Ser21/9}$, pan GSK3αβ, N-Myc, CyclinD1, CyclinD2, p16, and (B) against p18, p21, p27, p53, and tubulin. Cell-Intrinsic Deficits Cause Reduced Proliferation of β1−/− NPCs. (C) Immunoblot analysis of wildtype, β1−/− and β1+/− NPCs using antibodies against Glut1 and Glut4. (C and D) Oxygen consumption {basal and uncoupled (maximal) was measured using a Clark Oxygen electrode in wild-type, β1−/− and β1+/− NPCs and MEFs. Experiments with MEFs were performed three times from three independent litters and data shown is representative. For NPC experiments, the NPCs derived from four wildtype and four β1−/− embryos obtained from 3 independent litters were pooled.

FIG. 45. This figure illustrates FACSCAN analysis of wild-type NPC cell cycle. Note higher percentage of cells in G1 (M1) and lower percentage of cells in G2M (M3).

FIG. 46. This figure illustrates FACSCAN analysis of β1−/− NPC cell cycle. Note lower percentage of cells in G1 (M1) and higher percentage of cells in G2M (M3).

FIG. 47. This figure illustrates FACSCAN analysis of cell cycle of β1−/− NPCs Expressing GFP (control).

FIG. 48. This figure illustrates FACSCAN analysis of cell cycle of β1−/− NPCs Expressing Wild-Type Rb.

FIG. 49. This figure illustrates FACSCAN analysis of cell cycle of β1−/− NPCs expressing RbS804A Mutant.

Figure 50:
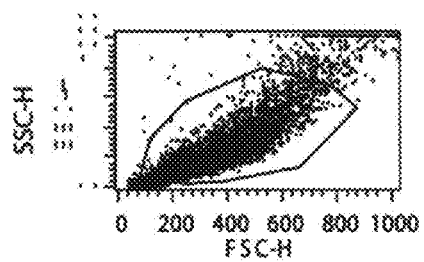
Figure 50:
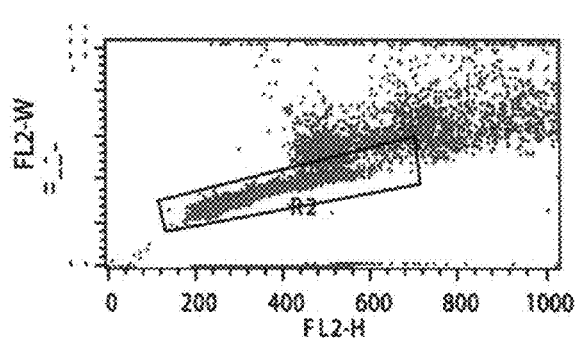
Figure 50:
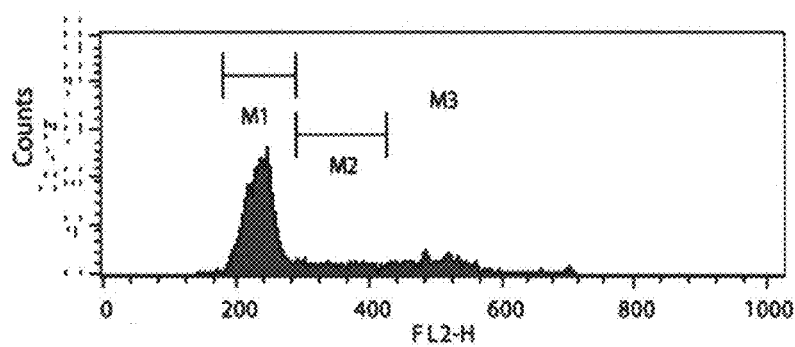

FIG. 50. This figure illustrates FACSCAN analysis of cell cycle of β1−/− NPCs Expressing RbS804E Mutant. Note that the number of cells in the G1 (M1) is increased and that in G2M (M3) is reduced.

FIG. 51. This figure illustrates FACSCAN analysis of cell cycle of β1−/− NPCs Expressing RbS804D Mutant. Note that the number of cells in the G1 (M1) is increased and that in G2M (M3) is reduced.

FIG. 52. This figure illustrates FACSCAN analysis of cell cycle of Wild-Type NPCs Expressing RbS804A Mutant. Note a decrease in the number of cells in G1 (M1) and accumulation of cells in G2M (M3).

FIG. 53. This figure illustrates FACSCAN analysis of cell cycle of Wild-Type NPCs Expressing GFP Only (control).

FIG. 54. This figure illustrates that energy restriction and growth factor signaling utilize the AMPK-Rb axis to enhance NPC proliferation. (A) Densitometric analysis of WT NPCs using indicated antibodies after 2-hr growth factor stimulation in the presence or absence of AMPK inhibitor compound C (CC; 5 mM). (B and C) Proliferation assay of WT NPCs (B) and β1−/−NPCs (C) cultured for 48 hr under glucose-limiting conditions (Cont=25 Mm glucose, which is the amount in neurobasal medium). Data are representative of three independent experiments (#p=0.07; *p % 0.005). Error bars indicate SD. (D and E) Densitometric analysis using phospho-specific AMPKα$^{Thr172}$, Rb$^{Ser800/804}$, ACC$^{Ser79}$, and pan AMPKα, Rb, and ACC antibodies. AU, arbitrary units.

FIG. 55. This figure illustrates that energy restriction and growth factor signaling utilize the AMPK-Rb axis to enhance NPC proliferation. (A) Immunoblot analysis using phospho-specific AMPKα$^{Thr172}$, Rb$^{Ser800/804}$, ACC$^{Ser79}$, and pan AMPKα, Rb, and ACC antibodies. AU, arbitrary units. (B-E) Densitometric analysis using phospho-specific AMPKα$^{Thr172}$, Rb$^{Ser800/804}$, ACC$^{Ser79}$, and pan AMPKα, Rb, and ACC antibodies. AU, arbitrary units.

FIG. 56. This figure illustrates that energy restriction and growth factor signaling utilize the AMPK-Rb axis to enhance NPC proliferation. (A) Immunoprecipitation assay using Rb antibody and Western blot with E2F1 antibody from NPCs grown in the indicated glucose concentration in the absence or presence of CC (5 mM). (B) Immunohistochemistry of saggital sections of E14.5 wildtype and β1−/− body using pHistoneH3 antibody (red).

Figure 57:
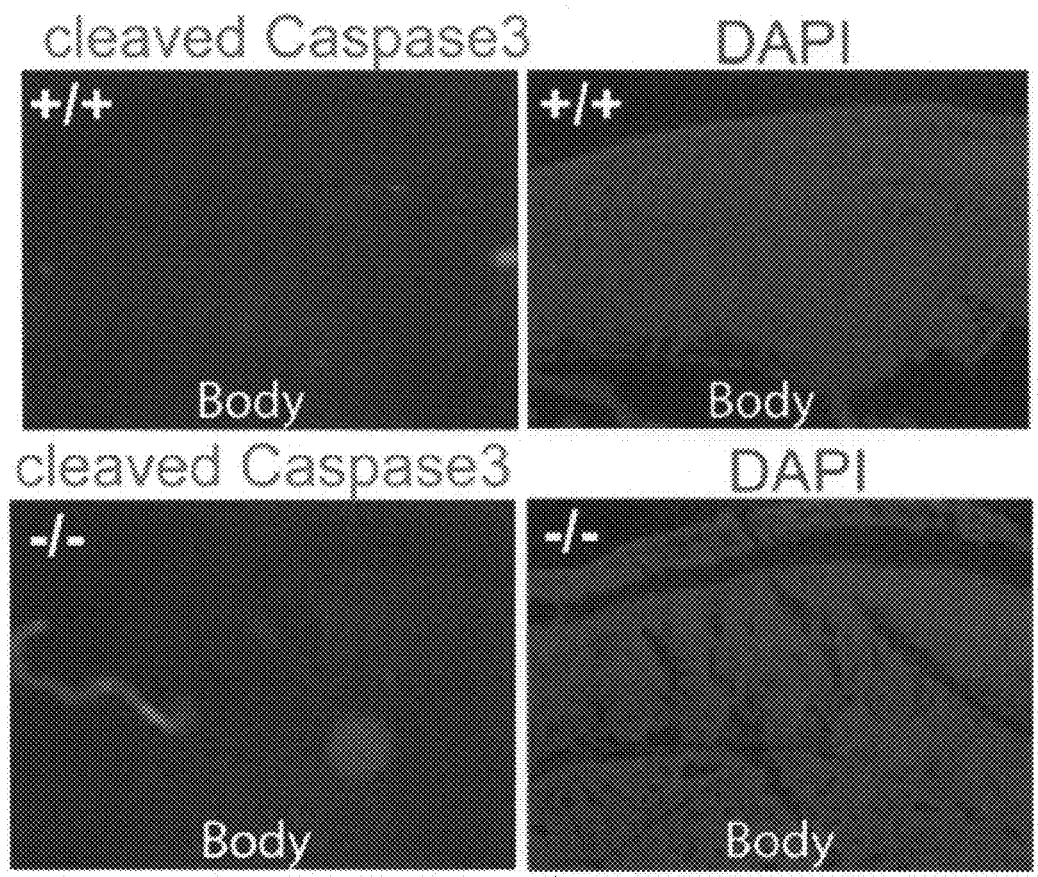

FIG. 57. This figure illustrates lack of proliferation or apoptosis defects in E14.5 β1−/− body. Immunohistochemistry using cleaved Caspase3 antibody (red) on saggital sections of the E14.5 body of wild-type and β1−/− embryos. Nuclei were counterstained with DAPI.

FIG. 58. This figure illustrates lack of proliferation or apoptosis defects in E14.5 β1−/− body. Immunohistochemistry using cleaved Caspase3 antibody (red) on saggital sections of the E14.5 liver (A) and interdigital junctions (B) of wild-type and β1−/− embryos. Nuclei were counter stained with DAPI.

FIG. 59. This figure illustrates that forced expression of β1 and constitutively active AMPK reverts phosphorylated Rb and ACC levels in β1−/− NPCs. (A) Immunoblot analysis of wild type and β1−/− NPC expressing lentiviral-delivered control (GFP), β1 or β2 subunits, using phospho-specific and pan antibodies towards AMPK, ACC and Rb. (B) Densitometric analysis of band intensities in (A). (C) Immunoblot analysis of wild-type and β1−/− NPC expressing lentiviral-delivered control (GFP), dominant negative (dn) or constitutively active (ca) AMPKα2 subunits, using phospho-specific and pan antibodies towards AMPK, ACC and Rb. (D) Densitometric analysis of band intensities in (C).

DETAILED DESCRIPTION

To investigate the role of the β subunits in regulating the physiologic functions of AMPK, we generated β1−/− mice. Our results demonstrate that the AMPKβ1 subunit is crucial for proper brain development through its regulation of AMPK phosphorylation of Rb, a step that potentially integrates nutrient and growth factor signaling pathways to influence neural differentiation.

Methods and compositions described herein utilize laboratory techniques well known to skilled artisans. Such techniques can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Harlow, E., Using Antibodies: A Laboratory Manual, Cold Spring Harbor Laboratory Press, Cold Spring Harbor, N.Y., 1999. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003.

EXAMPLES

The following examples utilize materials and methods including the following:
Generation of AMPKβ1 Mutant Mice ES cells (clone RRR454) containing an AMPKβ1 gene trap allele, was obtained from Bay Genomics. Briefly, AMPKβ1 gene trap ES cells were microinjected into blastocysts derived from superovulated pregnant mice, and these blastocysts were injected into pseudopregnant C57BL/6 females. Chimeric males (129/Ola mixed background) were mated with C57BL/6 females, and germ line transmission was confirmed by PCR genotyping of tail DNA. All procedures were carried out in the Washington University animal care facility.

The insertion site of the gene trap within the β1 locus was identified using a PCR ladder approach. Twelve forward primers were designed 250 by apart within intron 5 where the β-geo trap was inserted. The reverse primer was designed from the En2 sequence located in the gene trap N-terminus (primer e in FIG. 27A, SEQ ID NO. 4). PCR fragments were obtained and sequenced to identify the site of insertion. Primer 'c' (SEQ ID NO. 2), which was closest to the insertion site, and primer 'e' were used for subsequent PCR genotyping reactions (SEQ ID NO.: 4; FIG. 27A). The wild type β1 fragment was detected using primer 'c' (SEQ ID NO. 2) and a reverse primer (primer d in FIG. 27A, SEQ ID NO. 3) corresponding to β1 intronic sequences located ~200 nt downstream of the gene trap 5' junction. Southern blot analysis was performed by standard methods using a probe derived from the β-geo cassette.

Analysis of AMPKβ1 Mutant Mouse Tissues and Cells.

Light microscopy, phase contrast, immunofluorescence, and electron microscopy analyses were performed on cells and tissue sections. Hematoxylin and eosin staining, immunohistochemistry with various antibodies, were performed to visualize neural cells, proliferating and apoptotic stem and progenitor cells. Embryonic neural stem and progenitor cells (NPCs) were cultured from E12.5 animals for self renewal, proliferation, differentiation and apoptosis analysis. Immunoprecipitation assays and immunoblotting were performed with the indicated antibodies to detect active AMPK, ACC, and cell cycle regulatory molecules. Non-radioactive kinase assays were performed using bacterially produced Rb fusion protein containing residues 701-928.

TUNEL Staining

Tunel staining was performed on frozen sections, per the manufacturer's instructions (Roche, Indianapolis, Ind.), and visualized with Cy3-streptavidin and fluorescence microscopy.

In Vitro Culture of Neural Progenitors

Neurospheres were dissected from E12.5 CNS telencephalic lobes and cultured in neurobasal medium supplemented with B27 and N2, as described previously (Dasgupta, B. and Gutmann, D. H., J. Neurosci. 25, 5584-5594, 2005). To assess NPC growth, 104 cells from animals of each genotype were seeded in triplicate. At each time point, resulting neurospheres were trypsinized and counted on a hemocytometer. For self-renewal assays, single neurospheres were picked up by pipette and neurosphere diameter was measured individually under microscope. Ten similar-sized neurospheres of each genotype were triturated individually before plating, and the number of resulting secondary neurospheres generated per primary neurosphere was counted after 6 days. Neurosphere diameters were measured using Metamorph software. For NPC proliferation assay, NPCs were labeled with CFSE, as previously described (Dasgupta, B. and Gutmann, D. H., J. Neurosci. 25, 5584-5594, 2005). Briefly, NPCs were pulse labeled with 5 mM CFSE at 37° C. for 15 min, washed, and one-half of the cells were analyzed by FACS, while the other half was analyzed after 4 days of growth.

Nonradioactive In Vitro Kinase Assay

Nonradioactive in vitro kinase assay was performed as previously described (Lee et al., Nature 447, 1017-1020, 2007), with minor modifications. Briefly, WT NPCs were lysed with MAPK buffer, and AMPK was immunoprecipitated from WT NPCs with AMPKα1/2 antibody, washed with a buffer containing 10 mM Tris-Hcl (pH 7.5) and 0.5 M LiCl, and suspended in kinase buffer containing 0.5 mM ATP. CyclinD1/D2 (associated with CDK4/6) was immunoprecipitated with cyclinD1 and cyclinD2 antibodies. Reactions were carried out at 30° C. for 1 hr by adding RB-C fusion protein (residues 701-928; Cell Signaling Technology, Beverly, Mass.) to the reaction mix. Reaction was terminated by adding 6× Laemmli buffer and boiling for 5 min. Samples were resolved in 10% SDS-PAGE, and Western blot analysis was performed with phospho-RbSer$^{800/804}$ (Ser$^{807/811}$ in human) antibody (Cell Signaling Technology).

Quantitative Analysis of Cell Numbers and Statistical Methods

Student's t-test was used to calculate statistical significance with p<0.05 representing a statistically significant difference. For in vivo quantitative analysis of cell numbers, five square regions with identical areas were demarcated on each high-power field (20×) image. The regions were demarcated using Metamorph software, and cells were counted in each region. The sections were plane-matched and photographed digitally on a Nikon microscope. Sections from three mice of each genotype were used for manual cell counting. Brain size was measured using NIH Image J software. Pixels occupying the area of a dorsal view of the brain were quantitated and represented as brain size. Densitometric analysis of immunoblots was performed using GelPro analyzer software. Error bars in all figures indicate SD.

Tissue Preparation for Morphological and Immunohistochemical Analysis

P14 and P7 mice were perfused transcardially with 4% paraformaldehyde. Brains and optic nerves were dissected, and imaged with a digital camera (Photometrics, Buckinghamshire, UK) attached to a dissection microscope (Nikon, Japan). For histological analysis, brains were fixed in Bouin's fixative and processed for paraffin embedding and sectioning. Brain sections were stained with H&E and imaged with digital camera attached to a Nikon microscope. Brain sections were stained by Bielschowsky's silver impregnation to detect axons.

Immunohistochemistry was performed on deparaffinized six micron sections using antigen retrieval by standard methods. In some cases deparaffinized sections were treated for antigen retrieval using citrate buffer and incubated in 5% serum blocking solution prior to the overnight incubation of primary antibodies at 4° C. for 18 hr. For studies of embryos (E14.5, E18.5), the brains were fixed in 4% paraformaldehyde and cryoprotected in 30% sucrose in 0.1M phosphate buffer at 4° C. Tissues were embedded in OCT compound (Tissue-Tek, Torrance, Calif.) and frozen in cryomolds in liquid nitrogen. Cryosections (10 μm) were collected on Superfrost glass slides, permeabilized with 0.1% Triton X-100 in PBS, blocked with 10% horse serum in PBS, and incubated with primary antibodies at 4° C. for 18 hr.

Immunohistochemistry

The primary antibodies used on post natal brain sections were NeuN, Calbindin (Millipore, Billerica, Mass.), GFAP, S100β (Sigma, St Louis Mo.), MAP2 (BDPharmingen, Franklin Lakes, N.J.), APC (Calbiochem, San Diego, Calif.), and MBP (Sternberger Monoclonals Inc. Baltimore Md.). Donkey anti-sheep HRP secondary antibody was used for microscopic visualization (Jackson ImmunoResearch, West Grove, Pa.). For BrdU incorporation studies, E14.5 pregnant mice were injected intraperitoneally with BudU (100 μg/g body weight) and cryosections were processed as described (Wojtowicz and Kee, 2006). The following primary antibodies were used with this protocol: Ki67 (Vector laboratories, Burlington, Ontario, Canada), PhosphohistoneH3, Nestin, Sox2, BLBP, PAR3 (Millipore, Billerica, Mass.) Tuj1 (Covance, Richmond, Calif.), Olig2, BrdU (Abcam, Cambridge, Mass.), GFAP, Cleaved Caspase3, AMPKα1/2, phospho-AMPKα1/2Thr172, ACC, and phospho-ACCSer79 (all from Cell Signaling Technology, Beverly, Mass.), GABA (Sigma, Saint Louis, Mo.), phospho-GABA (Phosphosolutions, Aurora, Colo.). Microscopic visualization was obtained using appropriate Alexa 488, Alexa 568 (Invitrogen, San Diego, Calif.) and Cy3-tagged (Jackson ImmunoResearch, West Grove, Pa.) secondary antibodies. VECTASHIELD mounting medium (Vector laboratories, Burlington, Ontario, Canada) containing DAPI was used to counter stain nuclei and preserve fluorescence.

Immunocytochemistry

NPCs, MEFs and granule cell neurons cultured in vitro were fixed with 4% paraformaldehyde, blocked with 10% horse serum in PBS containing 0.1% Triton-X100 and incubated with primary antibodies at 4° C. for 18 hr. The primary antibodies used were AMPKβ1 (#4182, Cell Signaling Technology, Beverly, Mass.), AMPKβ2 (#4148, Cell Signaling Technology, Beverly, Mass.), PKCξ (Cell Signaling Technology, Beverly, Mass.), Glut1 (Rabbit polyclonal, a gift from Dr. Mike Mueckler, Washington University, Saint Louis), Glut4 ((Rabbit polyclonal, a gift from Paul Hruz, Washington University, Saint Louis), Acetylated tubulin (Sigma, Saint Louis, Mo.), Tuj1 (Covance, Richmond, Calif.), GFAP (Abcam, Cambridge, Mass.), O4, O1 (Millipore, Billerica, Mass.), Aquaporin 4 (Abcam, Cambridge, Mass.). Microscopic visualization was obtained using appropriate Alexa 488, Alexa 568 (Invitrogen, San Diego, Calif.) and Cy3-tagged (Jackson ImmunoResearch, West Grove, Pa.) secondary antibodies. Nuclei were counter stained with DAPI.

In Vitro Culture of Neural Progenitors

CNS telencephalic vesicles were digested with trypsin digest buffer containing 0.2% BSA (Sigma, St. Louis, Mo.), 0.5 mg/ml DNase I (Sigma), and 10% trypsin-EDTA stock (BioWhittaker, Walkersville, Md.) in HBSS at 37° C. for 10 min in a volume of 0.7 ml per vesicle. Equal volumes of 10% FCS medium containing 10% FCS (Life Technologies, Gaithersburg, Md.), 2 mM L-glutamine (BioWhittaker), 0.1% glucose (Sigma), and 0.1 mM 2-mercaptoethanol (Sigma) in DMEM/F-12 (Sigma) were added, and vesicles were triturated with 1 ml pipette tips. Pelleted cells were washed with dissociation medium containing 0.1% sodium bicarbonate, 15 mM HEPES (Sigma), 0.5% glucose, and 0.2% BSA in HBSS. Cells were finally resuspended in NSC medium containing Neurobasal medium (Invitrogen, San Diego, Calif.), 0.5 mM 2-mercaptoethanol, 2 mM L-glutamine, 5 IU of penicillin, and 5 µg/ml streptomycin (BioWhittaker) supplemented with 1% N2 supplement (Invitrogen, San Diego, Calif.), 2% B27 supplement (Invitrogen, San Diego, Calif.), 20 ng/ml epidermal growth factor (EGF) (Sigma, Saint Louis, Mo.), and 20 ng/ml basic fibroblast growth factor (FGF) (R & D Systems, Minneapolis, Minn.) and cultured in ultra low attachment dishes (Corning, Corning, N.Y.).

Immunoprecipitation, Subcellular Fractionation and Western Blot Analysis

Cultured NPCs or MEFs were lysed with MAPK lysis buffer (20 mM Tris-HCL, pH 7.5, 150 mM, NaCl, 1 mM EGTA, 1 mM EDTA, 1% TritonX-100, 2.5 mM sodium pyrophosphate, 1 mM β-glycerophosphate, 1 mM sodium vanadate, 1 mM PMSF, 1 mM DTT and protease inhibitor cocktail). AMPK was immunoprecipitated with AMPKα1/2 antibody (Cell Signaling Technology), Rb was immunoprecipitated with Rb antibody (Santa Cruz Biotechnology, Santa Cruz, Calif.) and cyclinD1/D2 (associated with CDK4/6) was immunoprecipitated with CyclinD1 and CyclinD2 antibodies (Cell Signaling Technology). The primary antibodies were incubated with 100 µg of protein lysate at 40 C for 16 hr, the immune complexes were collected by incubation with 10 µl of Protein G beads for 1 hr at 40 C and centrifugation. The immunoprecipitated proteins were analyzed by standard immunoblot analysis. Immunoblot analysis was carried out with the following primary antibodies: AMPKβ1/β2 C-terminal, AMPKα1/2, phospho-AMPKα1/2$^{Thr172}$, ACC, phospho-ACC$^{Ser79}$, pRbSer$^{800/804}$ (Ser$^{807/811}$ in human) pRb$^{Ser780}$, E2F1, phospho-Erk1/2$^{Thr202/Tyr204}$, Erk1/2, phospho-Akt$^{Ser473}$, Akt, phospho-GSK3αβ$^{Ser21/9}$, Gsk3β, Histone H4, N-Myc, CyclinD1, CyclinD2, phospho-p53$^{Ser15}$, p53 (all from Cell Signaling Technology, Beverly, Mass.), Rb, p18, p21, p27 (all from Santa Cruz Biotechnology, Santa Cruz, Calif.), p16 (BD-Pharmingen, Franklin Lakes, N.J.), α-Tubulin (Sigma, Saint Louis, Mo.), β-Gal (Roche, Indianapolis, Ind.) Glut1 (Rabbit polyclonal, a gift from Dr. Mike Mueckler, Washington University, Saint Louis), Glut4 (Rabbit polyclonal, a gift from Paul Hruz, Washington University, Saint Louis), and p 19Arf (Rabbit polyclonal, a gift from Dr. Jason Weber, Washington University, Saint Louis). Detection was performed using anti-rabbit or anti-mouse HRP-linked secondary antibodies (Cell Signaling Technology, Beverly, Mass.) followed by Chemiluminescence (Millipore, Billerica, Mass.). When applicable, subcellular fractionation was performed using a commercially available kit (BioVision Inc. Mountain View, Calif.) following manufacturers instructions.

SAMS Peptide Assay

SAMS peptide assay to monitor AMPK activity was performed as described with some modifications (Derave et al., 2000; Winder et al., 1996). Briefly, tissues were homogenized with a motorized tissue homogenizer for 20-30 s in 500 µl of ice-cold buffer (225 mM mannitol, 75 mM sucrose, 10 mM Tris-HCL, pH 7.4, 1 mM EDTA, 5 mM sodium pyrophosphate, 50 mM NaF, 1 mM dithiothreitol, 1.5 mM PMSF, and protease inhibitor cocktail). The homogenate was centrifuged for 1 min at 15,000×g, and the supernatant was stored in aliquots at −80° C. for later determination of protein concentration and AMPK activity. AMPK holoenzyme was immunoprecipitated using AMPKα1/2 antibody and Protein G agarose from 200 µg of protein lysate, the beads were washed twice with kinase buffer (20 mM Tris-HCL, pH 7.5, 7.5 mM, MgCl2, 0.5 mM EGTA, 25 mM β-glycerophosphate, 0.5 mM Sodium vanadate, 1 mM PMSF, and protease inhibitor cocktail), and used in the kinase reaction (25 µl immunoprecipitate beads). The kinase reaction containing immunoprecipitated AMPK, 100 µM SAMS peptide substrate, 200 µM AMP and 1 µl (2 µCi) of 32PATP was incubated at 300 C for 20 min with gentle agitation. The reaction was centrifuged to pellet the beads and 20 µl of supernatant was spotted on Whatman P81 paper. The filter papers were washed thrice with 1% phosphoric acid, once with acetone, air-dried, and radioactivity was counted using a scintillation counter.

Electron Microscopy

P14 optic nerves were post-fixed in Karnovsky's fixative for 24 hr. One micron thick plastic-embedded sections were prepared and stained with toluidine blue. For EM, ultrathin sections were prepared, stained with uranyl acetate and lead citrate and examined with a JOEL 1200 electron microscope (JEOL, Peabody, Mass.).

Seizure Study

EEG recordings were obtained by placing two screw electrodes over each cerebral hemisphere to differentially record EEG compared to a midline reference screw electrode, using standard AC EEG amplifiers (Astro-Med, West Warwick, R.I.). The EEG was filtered (high frequency 100 Hz), digitized (200 Hz), and stored using PC-based commercial hardware and software (Digidata and Axoscope, Molecular Devices, Sunnyvale, Calif.). Mouse behavior was recorded simultaneously with a PC-based video camera system (Sanyo camera coupled to an MPEG1 encoder from Darim Vision, Ltd). Mice were monitored for behavioral and electrographic seizures for 30 min, then they were sacrificed. All aspects of this work were performed in the P30 Animals Model Core of the Hope Center for Neurological Disorders at Washington University.

In Vitro Culture of Granule Neurons and MEFs

Cerebellar granule cells were prepared from P2 animals as described (Segal et al., 1995) Briefly, cerebella were chopped by razor blade and digested in Trypsin/EDTA at 37° C. for 20 min. Trypsinization was stopped by adding equal volume of DMEM containing 10% FCS, and supernatant cell suspension was collected after allowing the debris to settle for 10 min. The supernatant was centrifuged and pellet was carefully overlaid on a Percol gradient (2 ml of 65% Percoll in HBSS, 2 ml of 35% Percoll in HBSS, and then 2 ml of cell suspension). The gradient was spun in a 15 ml tube at 4500 rpm (2000×g) for 20 min. The gradient was then divided into thirds. The middle third, which contained the granule cells, was plated in DMEM with 10% FCS on a tissue culture dish treated with poly-D lysine (50 µg/ml) for 30 min to remove the adherent glial cells. The medium containing the non-adherent cells was centrifuged. Finally, the pelleted granule cells were resuspended in DMEM containing 10% FCS, 0.1 mg/ml BSA, and 20 mM KCl to improve granule cell viability and plated on to polyornithine coated plates. Neurite outgrowth was analyzed by adding NT3 (10 ng/ml) or BDNF (10 ng/ml). For aggregate formation, purified granule cells were allowed to form aggregates overnight plated in high density onto 48 well dishes. MEFs were prepared from E13.5 embryos following a standard NIH 3T3 cell culture protocol. After removal of the head and visceral portions, the fibroblastic tissues were minced with razor blades and digested in 0.25% trypsin-EDTA solution for 1 h at 40 C. Dispersed cells from each animal were plated in 100-mm plates in DMEM supplemented with 10% FCS, 2 mM L-glutamine, 0.1 mM non-essential amino acids and antibiotics and grown until confluence. Cells were trypsinized and re-plated (106 cells/ 100-mm dish) every 3 days.

NPC Proliferation, Apoptosis, and Differentiation

For NPC proliferation assay, NPCs were labeled with CFSE {5-(and -6)-Carboxyfluorescein diacetate, succinimidyl ester}. CFSE (Invitrogen) is a cell-permeable fluorescent dye that is metabolized by nonspecific esterases to result in a compound that gets trapped in the cytosol. Dividing daughter cells receive one-half the amount of dye and, with continued division, lose one-half of the fluorescence with each subsequent cell division. We pulse-labeled both β1+/+ and β1−/− NPCs with 5 µM CFSE at 37° C. for 15 min in the dark. Cells were washed, and one-half of the cells were analyzed by flow cytometry. The remaining cells were allowed to grow for 4 days, and the fluorescence intensity was measured as above. Cell cycle study was performed using propidium iodide staining followed by flow cytometric analysis. For apoptosis assays, 1 µl of propidium iodide (BD-Pharmingen, Franklin Lakes, N.J.) was added to neurosphere cultures, incubated for 5 min and imaged by a CCD camera attached to an inverted fluorescent microscope (Nikon). Neurospheres were trypsinized and percentage of propidium iodide positive cells was counted under a fluorescent microscope. For neurosphere differentiation assays, neurospheres were seeded individually onto poly-D-lysine (50 µg/ml)-coated and fibronectin (10 µg/ml; Invitrogen, San Diego, Calif.)-coated wells and allowed to differentiate in growth factor-free N2, B27 supplemented medium for 6 days. After fixation, permeabilization and blocking, cells were stained with rabbit anti-GFAP (Abcam), mouse anti-Tuj1 (Covance, Berkeley, Calif.), and mouse anti-O4 IgM (Chemicon, Temecula, Calif.) primary antibodies, followed by incubation with appropriate Alexa Fluortagged secondary antibodies (Invitrogen, San Diego, Calif.) to detect astrocytes, neurons, and oligodendrocytes, respectively.

Cellular Respiration

Oxidative respiration studies were performed using a Clark oxygen electrode (Oxygraph; Hansatech Instruments, Norfolk, UK) as described previously (Chen et al., 2005). Briefly, $2 \times 10^6$ NPCs or MEFs from each genotype were resuspended in 300 µl of TD respiration buffer (137 mM NaCl, 5 mM KCl, 0.7 mM Na2HPO4, and 25 mM Tris-HCl, pH 7.5) and placed into the oxygraph chamber. After equilibration for 1 min, the chamber was stoppered, endogenous oxygen consumption was measured for 3 min. Maximal (uncoupled) respiration was monitored by adding 2,4-dinitrophenol (Sigma, Saint Louis, Mo.) to a final concentration of 400 nM.

Quantitative RT-PCR Analysis

RNA was isolated from NPCs using Trizol (Invitrogen, San Diego, Calif.). Quantitative RT-PCR analysis was performed using Sybr-Green methodology on a model 7500 Fast instrument (Applied Biosystems, Foster City, Calif.) as before (Araki et al., 2004).

Primer Sequences

```
β1 genotyping wildtype/mutant
forward primer c:
TGACTGTGGTCAGCCTGTTCTC          (SEQ ID NO. 2)

β1 genotyping wildtype reverse
primer d:
CACAGGACATAGGATGTGGCC           (SEQ ID NO. 3)

β1 genotyping mutant reverse
primer e:
CAGACAAGTAGATCCCGGCGCTC         (SEQ ID NO. 4)

β1 RT-PCR forward primer a:
TTGAACAAGGACACGGGCATCTC

β1 RT-PCR reverse primer b:
GACAGTATCGGCCTCAGGAAGATCG
```

Plasmids and Viruses

The dnAMPK and caAMPK plasmids were gifts from Russell Jones (University of Pennsylvania, Philadelphia Pa.). The human AMPKβ1 and β2 full length cDNAs were purchased from OpenBiosystems. All constructs were subcloned into the lentiviral shuttle vector FCIV and verified by nucleotide sequence analysis. The human β1 and β2 cDNAs were N-terminally tagged with the 6×His epitope. Viruses were prepared as described previously (Araki et al., 2004). Rb mutants were made from wild type mouse Rb cDNA purchased from Open Biosystems and using Quickchange II-XL site-directed mutagenesis kit (Stratagene, La Jolla, Calif.).

Example 1

Generation of AMPKβ1 Mutant Mice

To investigate the biologic roles of the AMPK β1 subunit, we generated mutant mice using ES cells in which the β1 gene was interrupted by the insertion of a βgeo cassette (henceforth called β1−/− mice). The insertion created a βgeo-β1 fusion protein containing exons 1-5 of β1. This produces a mutant β1 protein lacking the terminal 46 amino acids (FIG. 27A-D; FIG. 28A, B). This deleted domain is highly conserved in the closely related AMPK β2 protein and is required for the generation of the active AMPK heterotrimer through interactions with both the α and γ subunits (Iseli, T. J., et al., J. Biol. Chem. 280, 13395-13400, 2005). We confirmed the existence of a single βgeo integrant at the predicted site in the β1 locus by Southern blot analysis, PCR genotyping, RT-PCR analysis and nucleotide sequencing (FIG. 27A-D; FIG. 28A, B). We detected the β1-βgal fusion protein by immunoblotting with a β-gal antibody in lysates from multiple tissues, including brain (FIG. 28A).

As shown in FIG. 1A and FIG. 1B, AMPK activity is reduced in AMPKβ1-deficient mice. In these experiments, lysates from indicated brain regions of wildtype (+/+) and β1−/− mice were analyzed by immunoblot using β1/β2 C-terminal antibodies (A) or antibodies specific for total or phosphorylated AMPK (AMPK$^{Thr172}$) and ACC (ACC$^{Ser79}$) (B) (n=4 independent experiments). The absence of wild type β1 in lysates from β1-deficient E14.5 telencephalon (forebrain), P7 cerebellum (FIG. 1A) and MEFs (FIG. 27F) was confirmed using a β1/β2 C-terminal specific antibody. The loss of β1 caused a significant reduction of activated AMPK (phospho-AMPKα$^{Thr172}$) and phosphorylated ACC (phospho-ACC$^{Ser79}$), a downstream target of AMPK in the brain and other organs (FIG. 28C; FIG. 29A, FIG. 29B). A similar reduction in AMPK activity was observed by monitoring phosphorylation of the AMPK artificial substrate (SAMS peptide).

Example 2

AMPK β1−/− Mice Display Structural and Functional Brain Abnormalities

The β1−/− mutant mice were born in a proper Mendelian ratio, but failed to gain weight normally and were clearly emaciated by postnatal day 14 (P 14) (FIG. 30A, B). They displayed severe tremors, ataxic gait and seizure-like activity and died by P21.

Figure 5:
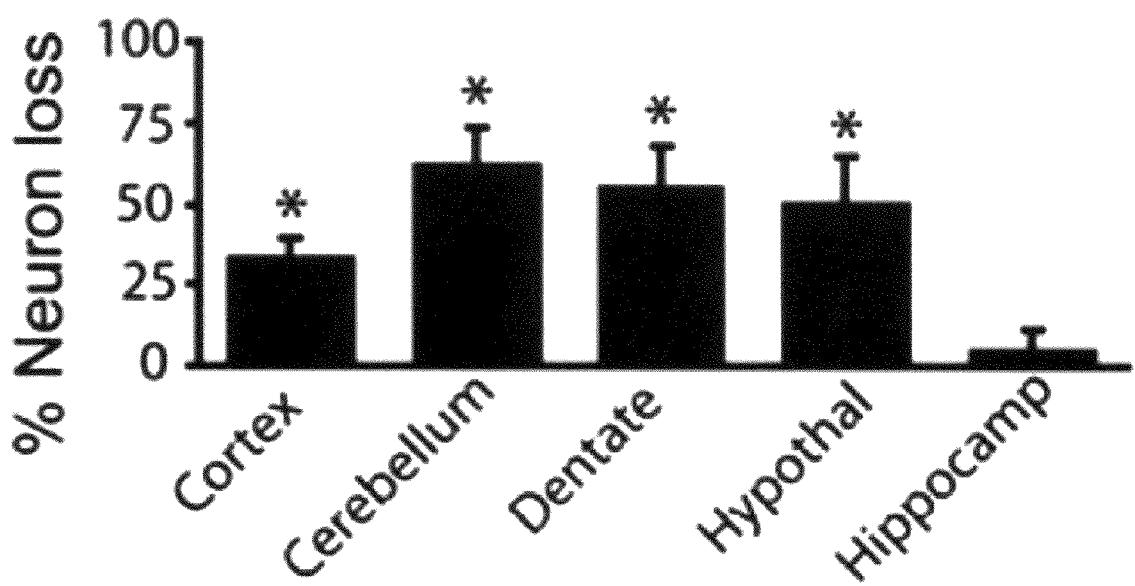
FIG. 5. This figure illustrates that AMPKβ1-deficient mice manifest brain abnormalities.

As illustrated in FIG. 2A and FIG. 2B, we demonstrate that AMPKβ1-deficient mice show reduced AMPK activity and manifest brain abnormalities. FIG. 2A provides a densitometric analysis of immunoblot data from FIG. 1. FIG. 2B presents a macroscopic view of WT and β1−/− brain at P14 (lower panel outlined by dotted line in upper panel) in β1−/− mice. CB, cerebellum; IC, inferior colliculi; SC, superior colliculi. Most notably, an examination of P14 β1−/− animals revealed a 50% reduction in overall brain size with severe cerebellar atrophy and marked reduction of the cerebral cortex resulting in improper cortical fusion and exposure of the superior (SC) and inferior colliculi (IC) (FIG. 2B; FIG. 5; FIG. 31A).

As illustrated in FIG. 3, AMPKβ1-deficient mice show manifest brain abnormalities. FIG. 3A presents coronal brain sections showing atrophy of dentate gyrus (arrow). and FIG. 3B presents coronal brain sections showing atrophy of cerebellum. IGL, inner granule layer. A histological examination revealed a nearly complete loss of the dentate gyrus (FIG. 3A). The cerebellum was characterized by a loss of the inner granule cell layer (IGL), extensive spongiform vacuolation, and disordered laminar organization (FIG. 31A). We did not observe abnormalities in the brain structures or in the behavior of the β1+/− animals.

To further characterize the extent of neuronal loss, we used the NeuN antibody to perform immunohistochemistry on brain sections. As illustrated in FIG. 4 and FIG. 5, AMPKβ1-deficient mice show manifest brain abnormalities. FIG. 4A shows NeuN immunohistochemistry of cortex and dentate gyrus (arrow). FIG. 4B shows NeuN immunohistochemistry of cerebellum. Quantification of neuronal losses assessed by counting NeuN+ cells is illustrated in FIG. 5 (*p<0.001, n=5). Error bars indicate SD. Significant losses (between 35-65%) of cortical neurons and granule neurons of the underlying dentate gyrus (FIG. 4A) and IGL of the cerebellum were clearly evident in the β1−/− brain (FIG. 4B; FIG. 5).

Example 3

Neuronal and Glial Deficits in β1−/− Mice

In these experiments, neuronal and glial distribution in β1−/− mice was examined (FIG. 6, FIG. 7 and FIG. 8). The data shows that these mice have both neuronal and glial CN deficits. As shown in FIG. 6, immunohistochemistry with an antibody against MAP2 and Bielschowsky's silver staining demonstrated widespread losses of dendritic processes and white matter axonal projections in these mutant mice, indicating that absence of β1 causes loss of neurons and neuronal processes. FIG. 6A: immunohistochemistry showing dendrites. FIG. 6B: silver staining showing axonal tracts, and adenomatous polyposis coli (APC) immunohistochemistry showing oligodendrocytes in the P14 brain. As shown in FIG. 7A, Myelin basic protein (MBP) immunohistochemistry shows myelination in the P14 brain. FIG. 7B provides an electron microscopic analysis of P14 β1−/− optic nerves. FIG. 7C presents a quantification of CFAP* cells in WT and β1−/− brains. *p=0.01, **p=0.002. Error bars indicate SD. FIG. 8A illustrates immunohistochemistry of the forebrain of E18.5 WT and β1−/− embryos using GFAP antibody. LV, lateral ventricle; arrowheads indicate migrating GFAP astroglia. FIG. 8B presents quantification of GFAP+ migrating astroglia in E18.5 WT and β1−/− brains. #p=0.006. Error bars indicate SD. FIG. 8C presents an EEG showing three seizure episodes recorded for 30 min in P14 β1−/− mice. The trace of one episode is enlarged at the bottom for clarity To investigate the effects of β1 loss on CNS glia, we examined oligodendrocytes by immunohistochemistry using the Adenomatous Polyposis Coli (APC) antibody and found a 75-80% loss of oligodendrocytes at P14 (FIG. 6C; 31B). This loss caused severe hypomyelination throughout the brain that was particularly evident in the corpus callosum and striatum (FIG. 7A, FIG. 32A). Consistent with this oligodendrocyte deficit, the β1−/− optic nerve was translucent and ~30% thinner than control nerves (FIG. 32B). Electron microscopic analysis demonstrated severe hypomyelination of mutant P14 optic nerve axons (FIG. 7B).

Figure 33:
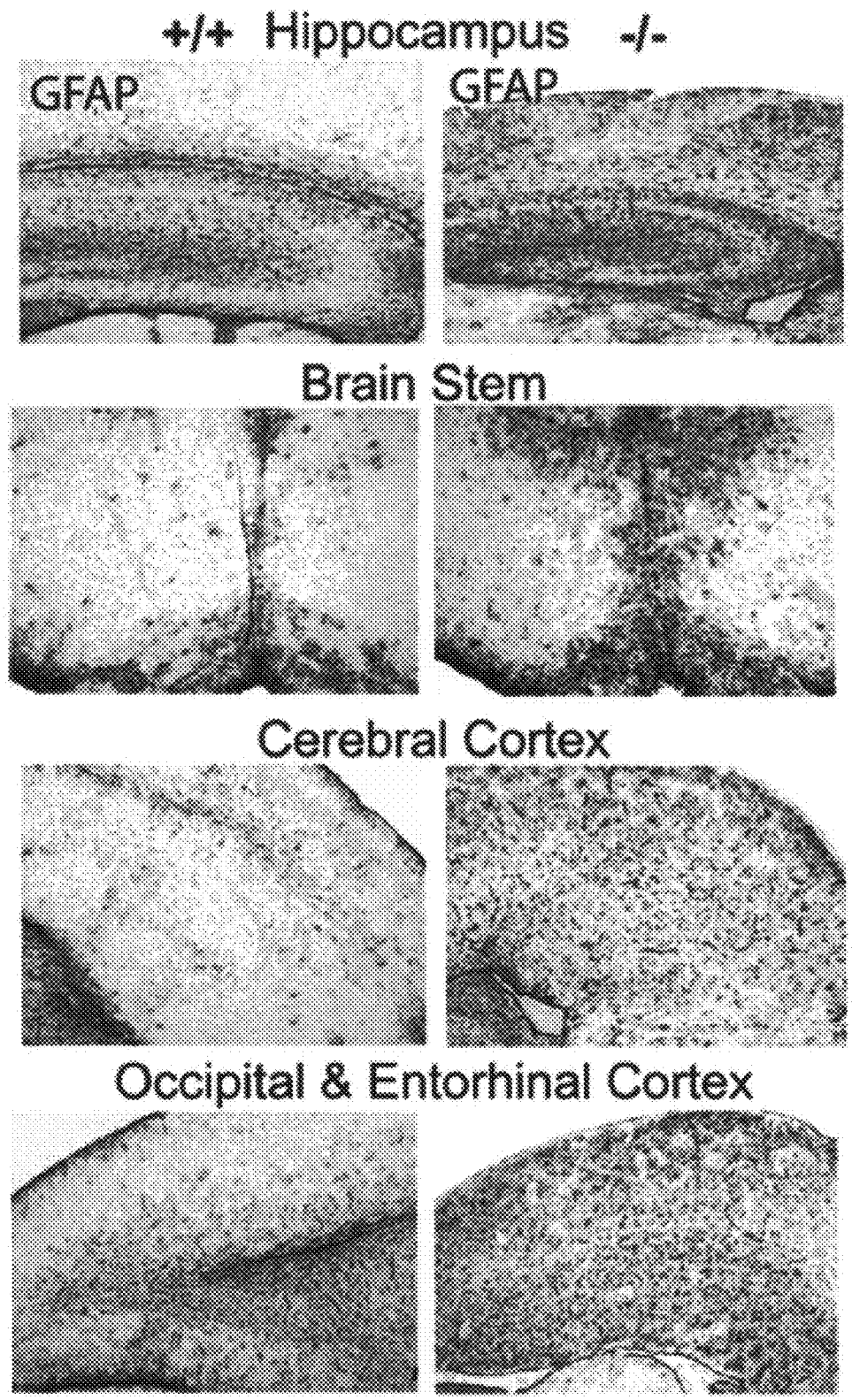
FIG. 33. This figure illustrates astroglial phenotype in the CNS of β1−/− Mice. Immunohistochemistry of the hippocampus, brain stem cerebral cortex and occipital and entorhinal cortex of wildtype and β1−/− mice using GFAP antibody to detect astrocytes.

In contrast, immunohistochemistry using glial fibrillary acidic protein (GFAP) antibody revealed overtly normal astrocyte differentiation in the β1−/− mice. However, there was extensive astrogliosis in the hippocampus, cortex and other areas of the β1−/− brain (FIG. 33, 34A). Thus, the loss of the AMPK β31 subunit resulted in neuronal and oligodendrocyte losses while leaving the astrocyte population overtly intact. Astrocyte maturation occurs later in development, and was difficult to study due to the early lethality of the β1−/− animals. We performed immunohistochemistry on P14 brains using antibodies to GFAP, an intermediary filament enriched in differentiated astrocytes (Cahoy et al., J. Neurosci. 28, 264-278, 2008) and brain lipid binding protein (BLBP), which is expressed in neural progenitors, radial glia, and immature/differentiating astrocytes (Domowicz et al., Dev. Biol. 315, 114-124, 2008; Hegedus et al., Cell Stem Cell 1, 443-457, 2007). The results showed that, in addition to extensive astrogliosis in β1−/− mice, there was an increased number of astrocytes throughout the brain (FIG. 33; FIG. 34B). Moreover, astrocytes in P14 dentate gyrus of WT animals expressed low levels of GFAP along with BLBP, whereas astrocytes in β1−/− mice expressed similar levels of BLBP, but higher levels of GFAP (FIG. 34B). At E18.5, consistent with previous findings (Barnabe-Heider, F., et al., Neuron 48, 253-265, 2005, very few GFAP+ cells were observed in WT mice; however, β1−/− brain contained many GFAP+ migrating astrocytes (FIG. 8A, FIG. 8B), indicating premature astrocytic differentiation of glial precursors in these mice. Together, these results indicate that, while loss of the AMPKβ1 resulted in fewer neurons and oligodendrocytes, this was accompanied by an increased number of fully differentiated astrocytes.

Example 4

AMPK-Directed $GABA_B$ Receptor Phosphorylation is Reduced in Seizure-Prone β1−/− Mice The extensive brain hypomyelination in β1−/− mice, along with their notable tremor and abnormal behavior, prompted us to monitor them for seizure activity. Electroencephalogram recordings revealed spontaneous electrographic seizures in mutant animals that usually recurred within less than 10 min (FIG. 8C). The seizures in these mice could result from the paucity of oligodendrocytes and resulting decreased in myelinated CNS fibers, the severe brain malformations, abnormal energy homeostasis in the brain, or perhaps through decreased inhibitory neuron activity. GABA is the major inhibitory neurotransmitter in mammalian brain, and it exerts its slow, prolonged effects via the GABAB receptor, which is made up of two subunits, R1 and R2. Interestingly, phosphorylation of the R2 subunit by AMPK at Ser783, acts to stabilize $GABA_B$ activation of inwardly rectifying K+ channels and decrease synaptic activity (Kuramoto et al., Neuron 53, 233-247, 2007). Disturbances of GABA+ neurons, either through selective loss of these neurons or via hypophosphorylation of the $GABA_B$ R2 receptor, could facilitate seizure propensity. Immunohistochemistry of P14 brain showed that the loss of GABAergic neurons was similar (~0.40%) to the loss of total neurons in β1−/− P14 brain. However, as shown in FIG. 9, immunohistochemical as well as Western blot analysis using a GABAB-R2 pSer783-specific antibody revealed that the R2 receptor was hypophosphorylated in β1−/− brain. FIG. 9A presents an immunohistochemistry analysis of WT and β1−/− P14 brain sections. FIG. 9B is a Western blot analysis of WT and β1−/− brain lysates. Both analyses used a phospho-$GABA_B R2^{Ser783}$ (p$GABA_B R2^{Ser783}$) antibody. FIG. 9C presents a quantification of signal intensities in FIG. 9B. Together, these results indicate that loss of AMPK activity can interfere with proper GABAergic signaling, potentially contributing to abnormal electrical activity in the β1−/− postnatal brain.

Example 5

AMPKβ1−/− Neural Stem and Progenitor Cells have Defects in Proliferation, Self-Renewal and Differentiation and have Unregulated Apoptosis In Vivo The deficits in multiple cellular lineages in the brain suggested that developmental processes were affected by β1 deficiency. To investigate this possibility, we examined mice at a number of embryonic and perinatal ages. At E18.5, we found that β1−/− embryos were similar in body size to wildtype embryos; however, the β1−/− brain was ~50% smaller than wildtype (FIG. 35A-D).

We considered the possibility that the smaller brain size could be due to a decreased number of cells, as we observed severe decreases in both neurons and oligodendrocytes at P14. Immunohistochemistry with phosphohistone H3 (PH3) to detect mitotic cells in the E14.5 forebrain ventricular zone (FIG. 10C), the P7 dentate gyrus (FIG. 36A, C) and the P7 cerebellum (FIG. 36B, C) revealed significantly reduced numbers of mitotic cells in the germinal zones of β1−/− brain, indicating a defect in self renewal/proliferation.

To determine whether the decreased size and cell number were due to abnormalities in proliferation and/or apoptosis, we first counted the number of cycling cells using Ki67 immunohistochemistry, which detects all actively cycling cells (FIG. 10A and FIG. 10B), BrdU labeling and immunohistochemistry, which marks cells in S-phase (FIG. 10B), and phospho-histone H3 (PH3) immunohistochemistry, which detects cells in M-phase (FIG. 10C). We found 22.22±4.66% less Ki67-positive cells around the lateral ventricles in β1−/− brain (FIG. 10A). To investigate this cell cycle defect, we pulse-labeled β1−/− E14.5 embryos with bromodeoxyuridine (BrdU) for 1 hr and performed immunohistochemistry with antibodies against BrdU, which marks cells in S-phase, phospho-histone H3 (PH3), which detects cells in M-phase, and Ki67, which detects all actively cycling cells. We observed a similar labeling index (proportion of cells in S-phase [(BrdU+)/total cycling cells (Ki67+)]) in WT and β1−/− forebrain (WT: 32.83±6.66 versus β1−/− : 33.46±4.25) (FIG. 10B). However, the number of cells in mitosis (PH3+ cells) in mutant E14.5 forebrain (FIG. 10C), as well as in P7 dentate gyrus and cerebellum (FIG. 36 A-C), were significantly reduced, indicating that the cell cycle defect occurs after DNA synthesis.

Example 6

Unregulated Apoptosis of Neural Stem and Progenitor Cells In Vivo in β1−/−Embryos Increased apoptosis could also be responsible for the decreased numbers of neurons and glia, and often occurs in response to abnormalities in cell cycle progression. We investigated this possibility by an immunohistochemical and TUNEL analyses (FIG. 11). FIG. 11A presents immunohistochemistry of the E14.5 forebrain with antibodies against cleaved caspase 3 (red). Immunohistochemistry using BrdU (green) and cleaved caspase (red) 1 hr after BrdU injection showed large numbers of apoptotic cells by cleaved caspase 3 in β1−/− E14.5 forebrain (FIG. 11A) and P7 cerebellum (FIG. 37A). FIG. 11B and FIG. 11C present TUNEL staining (red) in conjunction with immunohistochemistry using nestin antibodies (FIG. 11B, green) or Sox2 antibodies (FIG. 11C, green). Inset in FIG. 11B shows a magnified view of TUNEL/ Nestin double+apoptotic neural precursors. Although a few apoptotic cells were present in the proliferative Sox2-positive ventricular zone, the majority were found in the nestin-positive subventricular zone, particularly in the intermediate zone and subplate of the mutant forebrain (FIG. 11C and FIG. 11B). FIG. 11D shows double immunolabeling with BrdU and cleaved caspase 3 antibodies. Our results confirm that the majority of apoptotic β1−/− NPCs reside outside the BrdU-positive zone (FIG. 11D).

As cells that aberrantly exit cell cycle often undergo apoptosis, we examined cell cycle exit of β1–/– NPCs. E14.5 embryos were labeled with BrdU for 24 hr, and double immunolabeling with BrdU and Ki67 antibodies was performed. The fraction of BrdU-positive cells that were Ki67 negative represents the cells that exited cell cycle during the labeling period. FIG. 12A presents a cartoon illustrating the different layers of the embryonic forebrain. FIG. 12B shows immunohistochemistry using BrdU (green) and Ki67 (red) antibodies 24 hr after BrdU injection. FIG. 12C shows BrdU (green) and cleaved caspase 3 (red) antibodies 24 hr after BrdU injection. Although, it appeared that a higher number of BrdU-positive cells were present outside the subventricular zone in the β1–/– brains (FIG. 12B), the majority of these cell were Ki67 negative, but cleaved caspase 3 positive (FIG. 12C), indicating that a defect after S phase is responsible for the massive apoptosis of β1–/– NPCs.

We studied apoptosis further using an antibody to Tuj1 as a marker for proliferative zones during mouse embryonic neural development (Lee et al., Cell Motil. Cytoskel. 17, 118-132, 1990; Menezes, J. R. L., et al., J. Neurosci. 14, 5399-5416, 1994) and an antibody to Olig2 as a marker for oligodendrocytes (Yokoo, H., et al., Am. J. Pathol. 164, 1717-1725, 2004). We also investigated apoptosis in P7 brains using antibodies for GFAP (green) and cleaved caspase 3 (red). DAPI staining (blue) was used to highlight nuclei. FIG. 13A presents immunohistochemistry of E14.5 WT and β1–/– brain using Tuj1 (green) and cleaved caspase 3 (red). Inset shows colocalization of Tuj1 and cleaved caspase 3 in migrating neurons. FIG. 13B presents immunohistochemical analysis of E18.5 brains using an antibody to Oligo2 (green) and cleaved caspase 3 (red). (A-C) DAPI staining (blue) was used to highlight nuclei. In these experiments, we found increased numbers of apoptotic Tuj1-positive immature neurons and Olig2-positive oligodendrocyte precursors, indicating that β1–/– neural precursors undergo apoptosis as they migrate and differentiate into neurons and oligodendrocytes (FIG. 13A, FIG. 13B). However, immunohistochemistry for astrocytes at P7 (FIG. 14A) for GFAP (green) and cleaved caspase 3 (red), revealed no cell death in the astrocyte population at P7, or at E18.5. These results are quantified in FIG. 14B. Moreover, we found increased numbers of apoptotic Tuj1-positive immature neurons and Olig2-positive oligodendrocyte precursors, indicating that β1–/– neural precursors undergo apoptosis as they migrate and differentiate into neurons and oligodendrocytes (FIG. 13A, B; FIG. 37B). In contrast, no cell death was observed in the astrocyte population at P7 (FIG. 14A) or at E18.5. These results are quantified in FIG. 14B.

Although the normal body size of β1–/– embryos indicates that there were minimal cell losses in other tissues, the ubiquitous expression of AMPK prompted us to examine whether defects in proliferation and apoptosis could be detected in other regions of the body. We performed pHistone H3 and cleaved caspase 3 immunohistochemistry on sections of E14.5 embryo body, liver, and interdigital junctions. Unlike β1–/– embryonic brain, the number of proliferating and apoptotic cells in these β1–/– tissues was similar to WT embryo tissues (FIG. 56B, FIG. 57, FIG. 58). Collectively, these results indicate that loss of the AMPKβ1 subunit leads to proliferative defects and unregulated apoptosis specifically in the progenitors of the developing brain.

Example 7

The AMPK β Subunits Play Functionally Distinct, Cell Autonomous Roles in NPCs

The deficits in cultured neurospheres derived from β1–/– embryonic telencephalon indicate that the CNS deficits observed in β1-deficient mice are caused by CNS-intrinsic mechanisms, rather than alterations in the global metabolic state of these mice. To further investigate the cell-autonomous nature of these deficits, and understand why the highly related AMPKβ2 subunit cannot complement the β1 mutation in NPCs, we examined their expression and subcellular localization. In an experiment illustrated in FIG. 18A, lysates of NPCs were analyzed by immunoblot using an antibody that recognizes the C-terminus of both β1 and β2. We found that the β1 subunit is expressed at a 8-fold higher level than β2 in wildtype NPCs. There was a compensatory increase in β2 expression in β1–/– NPCs (FIG. 43A); however, this was obviously insufficient to compensate for the loss of β1 function. Subcellular fractionation studies showed that the level of active AMPK was reduced in both the cytoplasmic and nuclear fractions of β1–/– NPCs (FIG. 43A). In some experiments as illustrated in FIG. 18B, cells were stained immunocytochemically using either β1- or β2 N-terminal-specific antibodies (red). Nuclei were counterstained with DAPI (blue). β1 is present in the nucleus and cytoplasm, whereas β2 is present mainly in cytoplasm. Interestingly, immunocytochemistry using β1 and β32 N-terminal-specific antibodies in wild type NPCs (FIG. 18B) and MEFs (FIG. 43B) as well as immunoblot assays using a β1/β2-C-terminal-specific antibody in wildtype NPCs (FIG. 43C, D) confirmed that the β1 subunit was present in both the cytoplasm and nucleus, whereas the β2 subunit was primarily located in the cytoplasm. In addition, we did immunoprecipitation assays of AMPK from wildtype NPCs with AMPKα antibody followed by immunoblot using a β1/β2 C-terminal-specific antibody to detect β subunits present in the AMPK heterotrimer (FIG. 19A). and used densitometry to quantify the amount of β1 vs. β2 complexed with α subunits in NPCs (FIG. 19B). These pull-down assays using AMPKα1/2 subunit antibody for the immunoprecipitation step showed that 50% of the β1 subunit was bound to α subunits in wildtype NPCs; in contrast, only 9% of the β2 subunit was bound to α subunits. Interestingly, the loss of the β1 subunit resulted in instability of the α subunits in the β1–/– NPCs (FIG. 43A).

Figure 20:
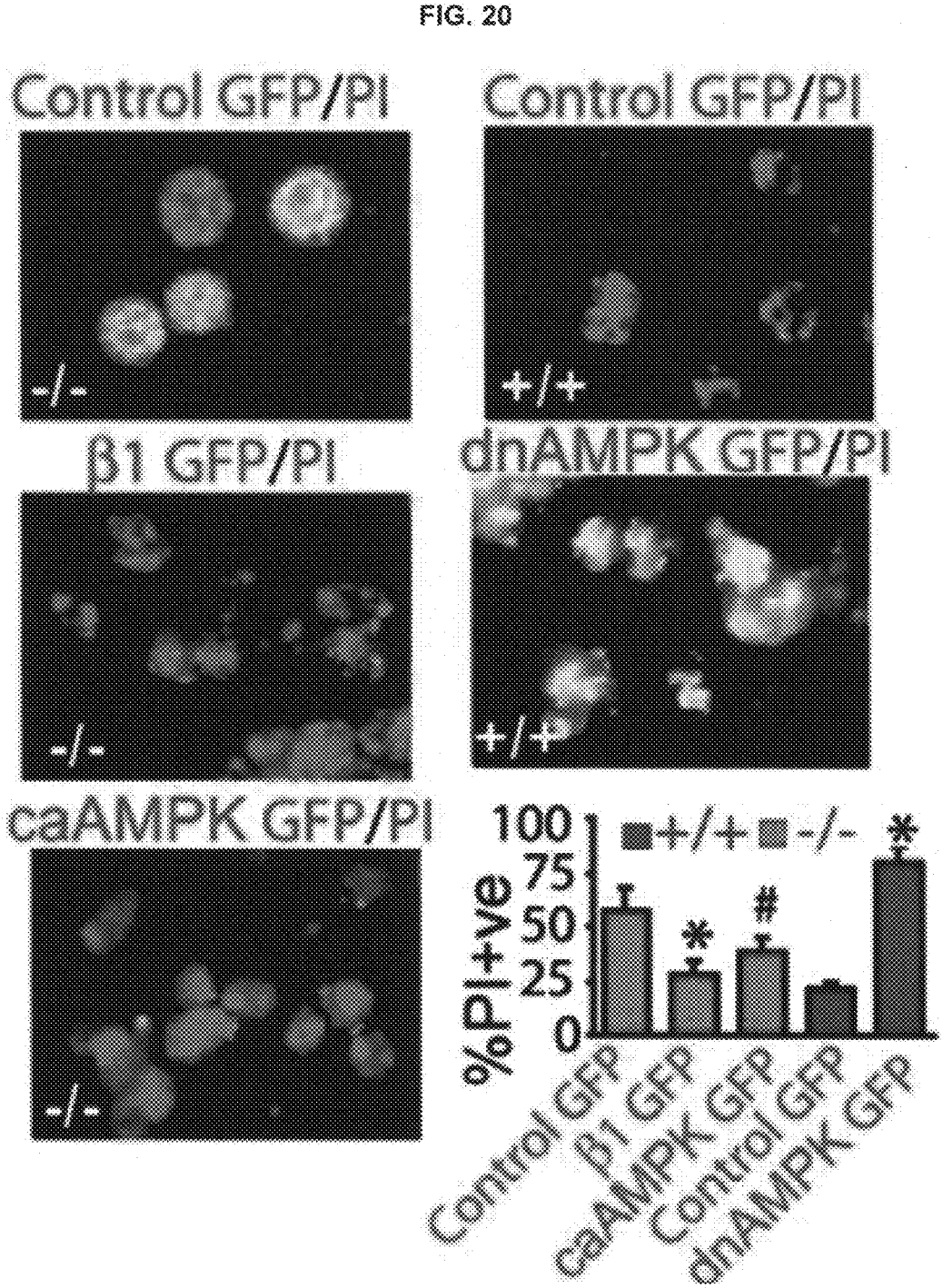
FIG. 20. This figure illustrates that expression of β1, but not β2, rescues β1−/− NPC phenotypes.
Figure 21:
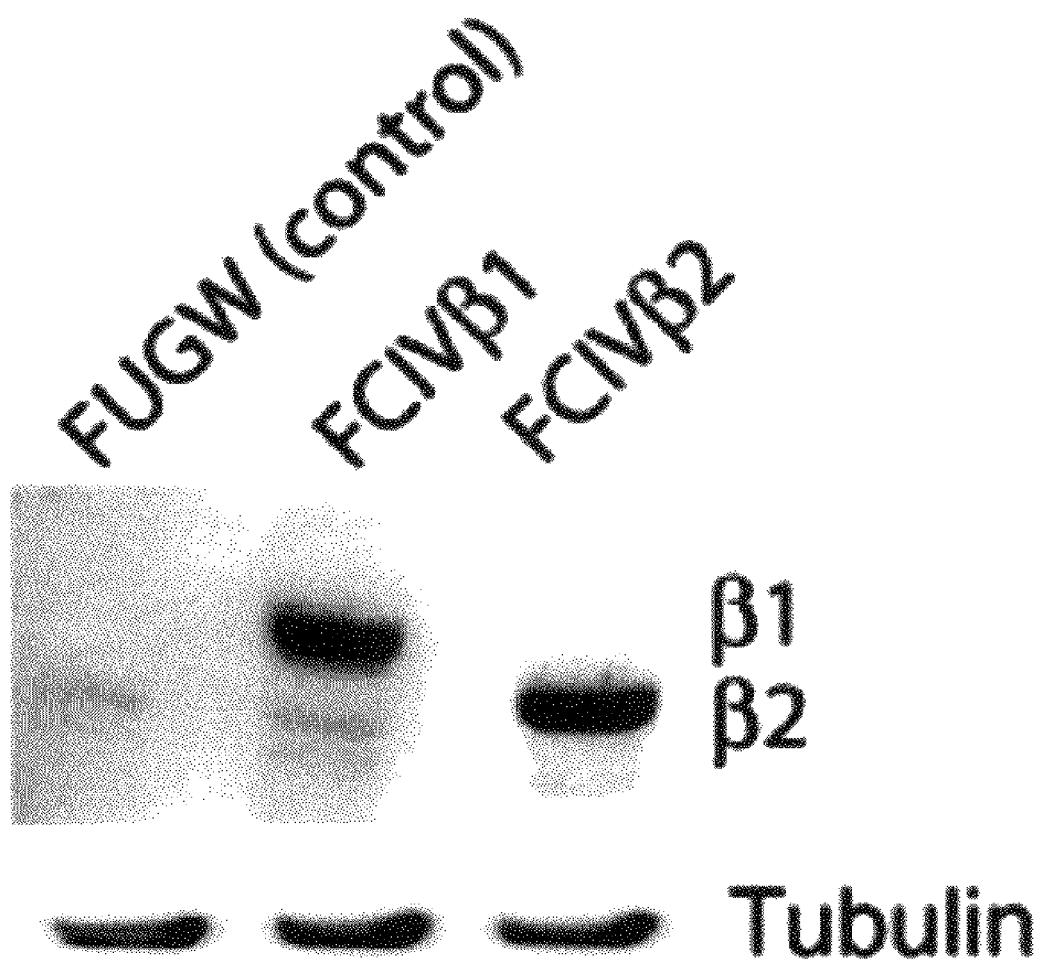
FIG. 21. This figure illustrates an immunoblot analysis of lentivirus infected AMPKβ1−/−NPC lysates with a β1/β2 C-terminal-specific antibody after immunoprecipitation with anti-His antibody.

The widespread cellular distribution of the β1 subunit, particularly in the nucleus, may imbue it with functions that are not shared by β2. To test whether the individual β subunits have unique attributes in NPCs, we tested whether their re-introduction into β1-deficient NPCs could complement the proliferation deficits of these cells. In these experiments, AMPKβ1–/– NPCs were infected with lentivirus expressing GFP (control), β1, β2 or constitutively active (ca) AMPKα2, while WT NPCs were infected with dominant negative (dn) AMPKα2. In some experiments, AMPKβ1–/– NPCs were infected with lentivirus expressing GFP (control), β1 or constitutively active (ca) AMPKα2 and wildtype NPCs were infected with lentivirus expressing GFP (control) or dominant negative (dn) AMPKα2, and propidium iodide (PI) uptake was monitored (FIG. 20). The growth rate (FIG. 19C) and self-renewal capacity were also monitored (FIG. 19D). Expression of lentiviral His-tagged human β1 or β2 subunit was measured in an immunoblot analysis of lentivirus infected AMPKβ1–/– NPC lysates with β1/C-terminal-specific antibody after immunoprecipitation with anti-His antibody (FIG. 21). Our data demonstrated that re-introduction of the β1 subunit rescues the growth (FIG. 19C), the self renewal (FIG. 19D) and the apoptosis (FIG. 20) defects of β1–/– NPCs, whereas the β2 subunit had no effect. These results indicate the cell autonomous nature of the NPC deficits in the β1-deficient mice and, that the β1 subunit subserves unique functions in NPCs that cannot be complemented by β2. In FIG. 19, #p<0.05, and data are representative of three independent experiments. Error bars indicate SD.

Neurons and oligodendrocytes are ultimately derived from self-renewing neural stem cells in the ventricular zone of the embryonic brain. To investigate whether the proliferation and apoptosis defects resulted from cell-autonomous defects in β1−/− NPCs, we cultured neurospheres from E12.5 telencephalon. As shown in FIG. 15, telencephalic neurospheres cultured for 48 hr (FIG. 15A). Neurospheres were assayed for growth (FIG. 15B) and self-renewal (FIG. 15C). 1' NS and 2' NS, primary and secondary neurospheres, respectively. Error bars indicate SD. The β1−/− neurospheres were significantly smaller in diameter (FIG. 15A, FIG. 16B) and produced fewer numbers of secondary and tertiary neurospheres (FIG. 15C). Direct cell counting revealed that β1−/− NPCs have severely impaired growth (FIG. 15B) and self renewal capacity (FIG. 15C). To examine whether the β1−/− NPCs have a slower proliferative rate, we performed a CFSE washout experiment. In these experiments, WT and β1−/− NPCs were incubated with CFSE dye and the fluorescence intensity of the cells was measured at 0 and 96 hr. (FIG. 16A) The numbers in parenthesis are mean fluorescence intensities. Unfixed WT and β1−/−neurospheres were stained (FIG. 16B) and analyzed quantitatively for apoptosis of β1+/+, β1+/− and β1−/− NPCs (FIG. 16C). *p<0.005. Error bars indicate SD. Flow cytometric analysis of mean fluorescence intensities of CFSE-labeled cells at 0 and 96 hr revealed that β1−/− NPCs proliferate ~50% more slowly than wildtype NPCs (FIG. 16A). Propidium iodide (PI) staining revealed the extent of cell death in these cultured neurospheres. We found that an increased number of β1−/−NPCs were PI-positive (dead or dying) when compared to wildtype or β1+/− neurospheres (FIG. 16B, FIG. 16C).

Finally, the severe cerebellar defects in β1−/− animals prompted us to examine cultured cerebellar granule cell precursors from P2 animals. We found that reaggregate formation, as well as neurite projection, was severely impaired in the β1−/− precursors (FIG. 42A). We also observed that 60%-70% of NeuN+ β1−/− reaggregates were apoptotic (FIG. 42B, C). In sum, these results indicate that cell-autonomous defects caused by β1 deficiency result in aberrant proliferation and/or cell fate determination of neural precursors.

Example 8

Defects in AMPK β1−/− NPCs are Cell Autonomous

The abnormalities in β1−/− NPCs are caused by cell-intrinsic mechanisms rather than by an altered global metabolic state in these mutant mice. To understand why β1 deficiency results in such devastating NPC defects, we performed Western blot analysis on β1−/− neurospheres, and found that pAMPK was almost absent, while pACC (a canonical target of AMPK) was reduced by about 50% (FIG. 17B).

To definitively prove that AMPK activity is necessary for regulated proliferation of NPCs, we expressed constitutively active (ca) and dominant negative (dn) AMPKα2 mutants in wildtype and β1−/− NPCs via lentivirus infection. We monitored NPC self renewal and apoptosis and found that the ca-AMPK partially rescued the self renewal (FIG. 19D) and apoptosis defects (FIG. 20) of β1−/− NPCs. Conversely, dnAMPK severely reduced self renewal (FIG. 19D) and caused catastrophic death of wild type NPCs (FIG. 20). These results indicate that AMPK activity is necessary for the proliferation and self renewal of NPCs.

Immunoblot analysis revealed that phosphorylated (active) AMPK was almost absent, while phosphoACC (a canonical mitochondrial target of AMPK) was reduced by ~50% in neurospheres derived from β1−/− embryos (FIG. 17). These results indicate that the β1−/− NPCs have cell intrinsic defects in proliferation and self renewal that lead to increased cell death.

AMPK is involved in central energy metabolism, and the developing brain is sensitive to metabolic imbalances. Thus, it was important to determine whether the brain anomalies in the β1−/− animals were due to global metabolic abnormalities, or whether they were cell autonomous to NPCs. While global metabolic problems would likely cause deficits in multiple tissues, to clearly address this issue, we isolated MEFs and cultured neurospheres from E12.5 telencephalon from β1−/− and WT embryos. In response to energy deprivation, AMPK increases mitochondrial respiration and glucose transporter expression. We examined both glucose transporter expression and basal as well as maximal oxygen consumption, and found that they were similar in β1−/− and WT NPCs and MEFs (FIG. 39A, B; 44B-D).

Example 9

AMPK Directly Phosphorylates Rb to Regulate NPC Cell Cycle

Decreased proliferation, enhanced apoptosis and aberrant differentiation of β1−/− NPCs are reminiscent of cells that inappropriately exit the cell cycle and undergo aborted/anomalous differentiation. To examine potential molecular mechanisms to account for these abnormalities in β1 NPCs, we performed immunoblot analysis of important cell cycle associated molecules. In NPCs, these include N-myc, which drives transcription of G1 cyclins in these cells (Galderisi, U., et al., Oncogene 22, 5208-5219, 2003), GSK3β, which phosphorylates and destabilizes N-Myc (Kenney, A. M., et al., Development. 131, 217-28, 2004), and other well-characterized cell cycle regulators. We found normal levels of both phosphorylated and total GSK3αβ, N-Myc, cyclin D1 and D2, and the cell cycle inhibitors p16, p18, p21 and p27 in β1−/− NPCs (FIG. 44A). However, we found that these pathways were normal in β1−/− NPCs (FIG. 39C, D), indicating that abnormalities in other effectors are responsible for the deficits in β1−/− NPCs. Other molecules central to NPC health, such as GSK3β, which phosphorylates and destabilizes N-Myc (transcription factor for D-type cyclins) (Galderisi et al., Oncogene 22, 5208-5219, 2003; Kenney et al., Development 131, 217-228, 2004), N-Myc, cyclin D1 and D2, and the cell cycle inhibitors p16, p18, p21, and p27, were all expressed at normal levels in β1−/− NPCs (FIG. 44A). Another critical regulator of cell growth is p53, which is phosphorylated at Ser15 by AMPK (Jones et al., Mol. Cell. 18, 283-293, 2005), was also unaltered in β1−/− NPCs (FIG. 44A). Together, these data indicate that the β1−/− NPC deficits were not caused by alterations in the well-characterized roles of AMPK in metabolic homeostasis, but rather by disruption of other pathways or by dysregulation of molecules downstream of N-Myc and cyclin D1/2.

In proliferating cells, the cyclin D1/2 associated kinases (CDK4/6) phosphorylate and inactivate their downstream substrate Rb, a necessary event for transit of the G1-S cell cycle checkpoint (Galderisi, U., et al., Oncogene 22, 5208-5219, 2003). The striking resemblance of the β1−/− brain abnormalities to those observed in animals lacking N-Myc (Knoepfler, P. S., et al., Genes Dev. 16, 2699-712, 2002), cyclin D1/D2 (Ciemeryc, M. A., et al., Genes Dev. 24, 3277-3289, 2002), Rb (Lee, E. Y., et al., Nature 359, 288-294, 1992). and Rb family proteins (McLear, J. A., et al, Mol. Cell.

Figure 22:
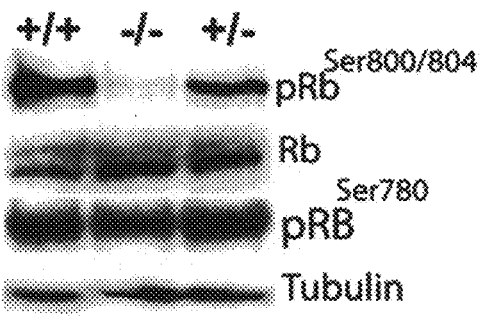
FIG. 22. This figure illustrates that AMPK phosphorylates Rb to regulate Rb-E2F interaction. (A) shows SEQ ID NO. 1 (ISPLKSPYKI) and SEQ ID NO. 7 (MRPSMSGLHL).
Figure 22:
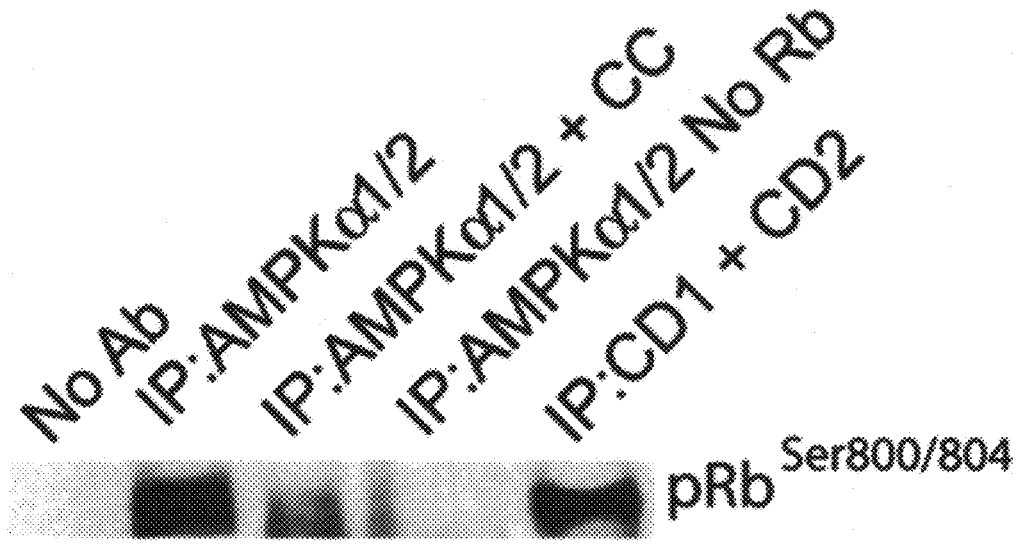

Neurosci. 33, 260-73, 2006) prompted us to scrutinize Rb for potential AMPK phosphorylation sites. Rb is exquisitely regulated by multiple phosphorylation events, and we noticed, in searching the Phosphosite database (www.phosphosite.org), that one of the multiple Rb phosphorylation sites, Ser804 (Ser811 in human), conformed to the consensus the AMPK consensus phosphorylation site. FIG. 22A illustrates the AMPK consensus sequence (top) and AMPK phosphorylation site in ACC, and potential site found in Rb (bottom). Immunoblot analysis of β1−/− NPC lysates using pRb$^{Ser800/804}$, pan Rb, pRb$^{Ser780}$, and tubulin antibodies revealed that phosphorylation of Ser804 is greatly decreased in β1−/− NPCs (FIG. 22B). Data are representative of three independent experiments. No change in total Rb or in phosphorylation at another site (Ser780) was observed, indicating that Ser804 is specifically hypophosphorylated in β1−/− NPCs. The antibody used in our study recognizes both Ser800 and Ser804. However, since only the Ser804, and not the Ser800, conforms to the AMPK consensus site, we believe that Ser804 is the likely residue phosphorylated by AMPK, and will be used in the text henceforth. Our mutagenesis studies (described hereinbelow) further reinforce this view.

The CDK-cyclin D complex is known to phosphorylate Rb at Ser804. Thus, the hypophosphorylation at this site in β1−/− NPCs could result from an indirect effect on CDK4/6 activity or a direct effect of AMPK on Rb. CDK4/6, which exist in complexes with cyclinD1/D2, were immunoprecipitated using cyclin D1/2 antibodies, and the activity was measured by nonradioactive in vitro kinase assays using bacterially produced Rb fusion protein (residues 701-928) as the substrate. We found that CDK4/6 activity from β1−/− and WT NPCs was equivalent (FIG. 24A), indicating that b1 deficiency did not affect CDK activity. To test whether AMPK directly phosphorylates Rb in NPCs, we immunoprecipitated either the AMPK holoenzyme (α/β/γ heterotrimers) using anti-AMPKα1/2 antibody or cyclin D1/2 (bound to CDK4/6) with cyclin D1/2 antibodies (control) from wildtype NPCs. In these experiments, phosphorylation was monitored by immunoblot using phosphor-Rb800/804 antibody. Data are representative of three independent experiments. Using this immunoprecipitated AMPK enzyme (or cyclin/CDK4/6 control), we performed non-radioactive in vitro kinase assays with bacterially produced Rb fusion protein (residues 701-928) as the substrate. As shown in FIG. 22C, AMPK holoenzyme was immunoprecipitated using AMPKα1/2 antibody from WT NPCs used to phosphorylate recombinant Rb protein (residues 701-928). We found that AMPK directly phosphorylated Rb at Ser804 and that this modification could be inhibited by the AMPK inhibitor, compound C (6-[4-(2-piperidin-1-ylethoxy)-phenyl]-3-pyridin-4-ylpyrazolo[1,5-α]pyrimidine).

Figure 23:
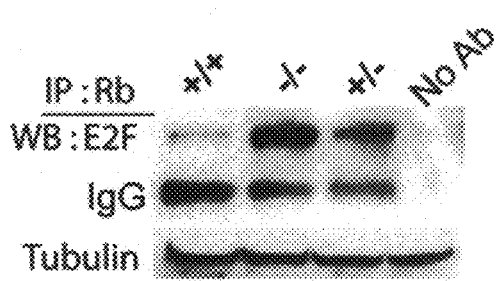
FIG. 23. This figure illustrates that AMPK phosphorylates Rb to regulate Rb-E2F interaction.
Figure 23:
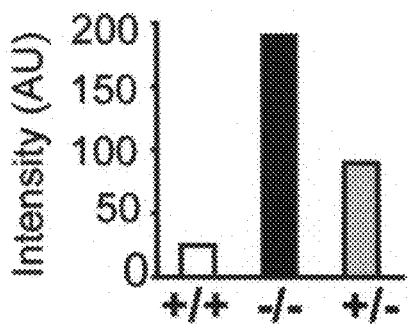
Figure 23:
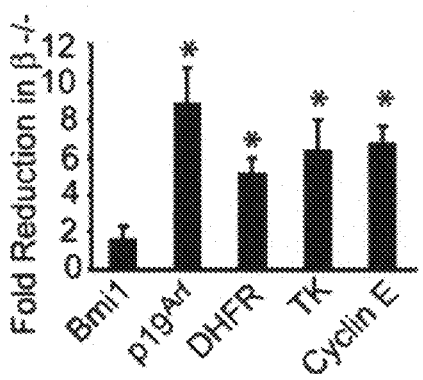
Figure 23:
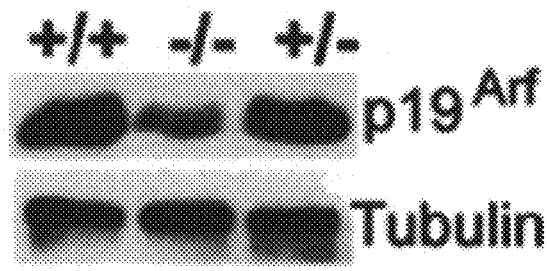
Figure 23:
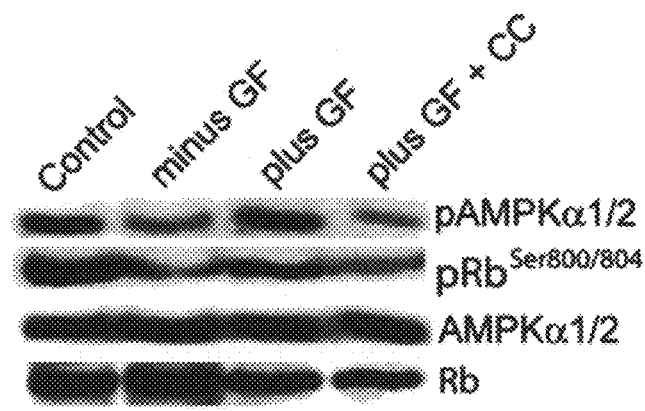

In proliferating cells, growth factor signaling promotes CDK-dependent phosphorylation of Rb to inhibit it from sequestering the G1 transcription factor E2F1 (Galderisi, U., et al., Oncogene. 22, 5208-19, 2003). To examine whether E2F1 is sequestered by hypophosphorylated Rb in β1−/− NPCs, we immunoprecipitated Rb from NPCs. In these experiments, NPC lysates were immunoprecipitated with pan Rb antibody, followed by Western blot with an E2F1 antibody and densitometry. Immunoblot analysis using anti-E2F1 antibody showed 7.6-fold more E2F1 was bound to Rb in β1−/− vs. wildtype NPCs (FIG. 23A, FIG. 23B). AU, arbitrary units. These data indicate that aberrant regulation of the Rb-E2F1 complex is at least partially responsible for the β1−/− NPC deficiencies.

To gain insight into how β1 deficiency causes the differential loss of specific CNS cell types, the multilineage differentiation potential of these neurospheres was examined. In these experiments, we found that AMPKβ1 loss results in cell-autonomous NPC defects. FIG. 17A illustrates quantification of immunohistochemical results obtained from in vitro differentiation of β1+/+, β1+/− and β1−/− neurospheres showing percentage of neurons (Tuj1), oligodendrocytes (O4) and astrocytes (GFAP). *p<0.001. Data are representative of at least three independent experiments. Error bars indicate SD. FIG. 17B illustrates that expression of β1, but not β2, rescues β1−/− NPC phenotypes. These experiments involved immunoblot analysis of NPC lysates using phospho-AMPK$^{Thr172}$, total ACC and phospho-ACC$^{Ser79}$. We found that β1−/− neurospheres produced fewer Tuj1-positive neurons (55.0±8.25%) and O4-positive oligodendrocytes (60.45±2.5%), but similar numbers of GFAP-positive astrocytes (FIG. 17A; FIG. 40C-E).

To investigate the consequences of increased Rb sequestration of E2F1 in β1−/− NPCs, we used qRT-PCR to measure the levels of E2F1 S-phase target genes. In these experiments, relative levels of E2F1-regulated mRNAs in wildtype vs. β1−/− NPCs were determined using qRT-PCR. As shown in FIG. 23C, Cyclin E, dihydrofolate reductase, thymidine kinase and p19$^{Arf}$ were downregulated 5.2±0.4 to 8.8±2.2 fold in β1−/− compared to wildtype NPCs (FIG. 23C). All results were normalized to (3-actin levels.

We also examined p19$^{Arf}$ protein expression, as increased p19$^{Arf}$ levels result in enhanced p53 activation and apoptosis (Eischen, C. M., et al., Genes Dev. 13, 2658-2669, 1999). In these experiments, lysates from NPCs were analyzed by immunoblot using a p19$^{Arf}$ antibody. Consistent with our qRT-PCR results, we observed a 5.6-fold reduction of p19" protein in (3'−/−NPCs (FIG. 23D).

The effects of AMPK β1 deletion on Rb-E2F1 activity led us to consider whether the highly conserved AMPK signaling pathway is fundamentally important for NPC responses to proliferative signals such as growth factors. To test our hypothesis, we cultured wildtype NPCs in the absence of growth factors for 2 h (withdrawal phase) and then added back EGF and FGF. In these experiments, growth factors (EGF and FGF) were withdrawn from wildtype NPCs for 2 h, then growth factors were re-administered for 1 h in the presence or absence of Compound C (6-[4-(2-piperidin-1-ylethoxy)-phenyl]-3-pyridin-4-ylpyrazolo[1,5-α]pyrimidine). Immunoblot analysis was performed using phospho-specific AMPKα$^{Thr172}$ and Rb$^{Ser800/804}$ and pan AMPKα and Rb. * p<0.005. AU=arbitrary units. As shown in FIG. 23E, cells treated with growth factors had increased levels of phosphorylated AMPK and increased phosphorylation of Rb at Ser804. However, when EGF and FGF were added to cells treated with the AMPK inhibitor Compound C, no increase in phosphoAMPK or phosphoRb was observed. Thus, it appears that the failure of AMPK-directed phosphorylation of Rb in β1−/− NPCs, perhaps in response to endogenous growth factors, results in the relative inability to enter S phase as well as aberrant differentiation that leads to apoptosis.

These results indicate that an in vitro cell culture such as an NPC culture can be used for screening candidate compounds for efficacy as inhibitors or activators of AMPK activity. In such screens, cells, lysates of cells, or cell-free mixtures comprising polypeptides of AMPK and a phosphorylation target can be contacted with a candidate compound, and effects on phosphorylation of the AMPK phosphorylation target can then be determined by immunological or other biochemical methods well know to skilled artisans, such as, without limitation, immunoprecipitations and/or Western blot analyses.

Differentiation of β1–/– astrocytes was tested using immunocytochemistry with antibodies to BLBP (immature astrocyte marker), GFAP, and Aquaporin4 (mature astrocyte markers) (Bachoo et al., Proc. Natl. Acad. Sci. USA 101, 8384-8389, 2004; Cahoy et al., J. Neurosci. 28, 264-278, 2008) showed that an increased number of β1–/– astrocytes lost BLBP expression and displayed robust GFAP and Aquaporin4 expression (FIG. 41A-D), indicating that they prematurely differentiate in vitro as they do in vivo.

We also examined cerebellar granule cell precursors from wildtype and β1–/– P2 animals. Reaggregate formation and neurite projection were severely impaired in the β1–/– precursors (FIG. 42A) and 60-70% of NeuN+ β1–/– reaggregates were apoptotic (FIG. 42B, C). These results indicate the regulation of proliferation and/or cell fate determination of neural precursors is aberrant in β1–/– animals.

Example 10

β1–/– NPCs Display Defects in the G2M Phase of the Cell Cycle

The Rb-E2F complex plays multiple cellular roles, including serving as a gate keeper of the G1-S restriction point, the G2-M phase, cell cycle exit, cellular differentiation, and regulation of apoptotic cell death (Burkhart and Sage, 2008; Rigberg et al., 1999; Naderi et al., 2002; Yen and Sturgill, 1998; Niculescu et al., 1998). Many of these defects are present in β1–/– NPCs, and our previous analysis demonstrated alterations in cell proliferation. The abnormal regulation of Rb in these cells prompted us to perform flow cytometric analysis to examine cell cycle progression in these cells. In comparing β1–/– and WT NPCs, we found comparable numbers of cells in S phase (WT: 16.47±4.7%; β1–/–: 18.06±3.95%), less β1–/– cells in G1 (WT: 71.5±6.5%; β1–/–: 58.25±3.25%; p=0.005), and almost twice as many β1–/– cells in G2M phase (WT: 12.12±1.7%; β1–/–: 22.56±1.95%; p=0.001) (FIG. 45A-C, Table 1; FIG. 46A-C, Table 2), indicating that β1–/– cells have defects that prevent them from properly exiting or reentering the cell cycle. To firmly establish a direct connection between these cell cycle defects and the AMPK-Rb signaling axis, we examined the levels of pAMPK and pRb in β1–/– NPCs expressing β1, β2, caAMPK, or dnAMPK. β1–/– NPCs expressing caAMPK or β1, but not β2, showed increased levels of pAMPK, pRb, and pACC levels (FIG. 59A-D), while WT NPCs expressing dnAMPK showed significantly decreased Rb and ACC phosphorylation (FIG. 59C, D). Together, these results indicate the importance of the AMPK-Rb signaling axis in NPC growth, a pathway that is largely regulated through the β1 subunit.

The highly orchestrated, cyclical phosphorylation of Rb throughout the cell cycle makes Rb overexpression studies difficult. Nevertheless, we generated lentiviruses expressing WT Rb, Rb(S804A), removing the critical phosphorylation site, and Rb(S804E) and Rb(S804D), potentially creating phosphomimetics. These lentiviruses were used to examine whether an Rb phosphomimetic mutant could rescue the β1–/– NPC growth defect, and whether a phosphorylation-resistant Rb would cause growth defects in WT NPCs. We infected WT NPCs with lentivirus expressing GFP (control), WT Rb, or Rb(S804A), and β1–/– NPCs with lentivirus expressing GFP (control), WT Rb, Rb(S804A), Rb(S804E), or Rb(S804D). The cells were counted 24 hr after infection. Both WT Rb and Rb(S804A) caused significant growth reduction in WT NPCs. β1–/– NPCs expressing GFP, WT Rb, or Rb(S804A) showed poor growth; however, those expressing the phosphomimetic mutants, showed improved growth (FIG. 24B). We continued to observe these cells and found that, by 48 hr, the neurospheres expressing Rb(S804E) or Rb(S804D) stopped growing and began to look unhealthy, indicating that constitutive phosphorylation of Rb at this site may prevent cells from reentering cell cycle.

Previous analysis showed that β1–/– NPC cell cycle progression was blocked at the G2M phase. We therefore investigated whether β1–/– NPCs expressing Rb(S804E) or Rb(S804D) could now transit the G2M stage. Flow cytometric analysis performed on cells 24 hr after lentiviral infection showed that β1–/– NPCs expressing WT Rb or Rb(S804A) had 27% cells in G2M, whereas β1–/– NPCs expressing Rb(S804E) or Rb(S804D) had 16% cells in G2M (FIG. 24C; FIG. 47-51; Tables 3-7). Interestingly, WT NPCs expressing Rb(S804A) had more cells (~22%) in G2M than those expressing GFP (~10%) (FIG. 24C; FIG. 52, 53; Tables 8, 9). These results indicate that the hypophosphorylation of Rb at Ser804 is responsible for the G2M defect in β1–/– NPCs, as a phosphomimetic Rb mutant can partially restore the ability of these cells to transit G2M. It is interesting that, although Rb is phosphorylated at 19 different Ser/Thr residues, many of which could serve overlapping as well as specific functions, the phosphorylation of Rb at Ser804 appears to play an important role in G2M phase and/or cell cycle exit in NPCs.

TABLE 1

Quantification of FACS data from FIG. 45

| Marker | Events | % Gated | % Total |
|--------|--------|---------|---------|
| All    | 8092   | 100.00  | 80.92   |
| M1     | 5785   | 71.49   | 57.85   |
| M2     | 1333   | 16.47   | 13.33   |
| M3     | 981    | 12.12   | 9.81    |

TABLE 2

Quantification of FACS data from FIG. 46

| Marker | Events | % Gated | % Total |
|--------|--------|---------|---------|
| All    | 5258   | 100.00  | 52.58   |
| M1     | 3095   | 58.86   | 30.95   |
| M2     | 950    | 18.07   | 9.50    |
| M3     | 1183   | 22.50   | 11.83   |

TABLE 3

Quantification of FACS data from FIG. 47

| Marker | Events | % Gated | % Total |
|--------|--------|---------|---------|
| All    | 1307   | 100.00  | 48.95   |
| M1     | 881    | 67.41   | 33.00   |
| M2     | 97     | 7.42    | 3.63    |
| M3     | 299    | 22.88   | 11.20   |

TABLE 4

Quantification of FACS data from FIG. 48

| Marker | Events | % Gated | % Total |
|--------|--------|---------|---------|
| All    | 4483   | 100.00  | 44.83   |
| M1     | 2537   | 56.59   | 25.37   |
| M2     | 471    | 10.51   | 4.71    |
| M3     | 1200   | 26.77   | 12.00   |

TABLE 5

Quantification of FACS data from FIG. 49

| Marker | Events | % Gated | % Total |
|---|---|---|---|
| All | 5229 | 100.00 | 52.29 |
| M1 | 2826 | 54.04 | 28.26 |
| M2 | 646 | 12.35 | 6.46 |
| M3 | 1424 | 27.23 | 14.24 |

TABLE 6

Quantification of FACS data from FIG. 50

| Marker | Events | % Gated | % Total |
|---|---|---|---|
| All | 5889 | 100.00 | 58.89 |
| M1 | 4104 | 69.69 | 41.04 |
| M2 | 734 | 12.46 | 7.34 |
| M3 | 954 | 16.20 | 9.54 |

TABLE 7

Quantification of FACS data from FIG. 51

| Marker | Events | % Gated | % Total |
|---|---|---|---|
| All | 4543 | 100.00 | 66.27 |
| M1 | 3138 | 69.07 | 45.78 |
| M2 | 500 | 11.01 | 7.29 |
| M3 | 112 | 16.99 | 11.26 |

TABLE 8

Quantification of FACS data from FIG. 52

| Marker | Events | % Gated | % Total |
|---|---|---|---|
| All | 1816 | 100.00 | 48.04 |
| M1 | 1137 | 62.61 | 30.08 |
| M2 | 197 | 10.85 | 5.21 |
| M3 | 404 | 22.25 | 10.69 |

TABLE 9

Quantification of FACS data from FIG. 53

| Marker | Events | % Gated | % Total |
|---|---|---|---|
| All | 6893 | 100.00 | 68.93 |
| M1 | 5050 | 73.26 | 50.50 |
| M2 | 1027 | 14.90 | 10.27 |
| M3 | 714 | 10.36 | 7.14 |

Example 11

Figure 25:
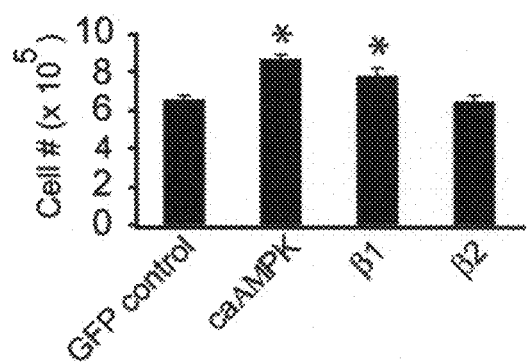
FIG. 25. This figure illustrates that AMPK phosphorylates Rb to regulate Rb-E2F interaction. (A) Proliferation assay of WT NPCs expressing GFP, constitutively active (ca) AMPK, β1, or β2 subunits. Data are representative of three independent experiments. Error bars indicate SD. (B) Immunoblot analysis of WT NPCs expressing caAMPK using pAMPKαThr172 and pRbSer800/804, and pan AMPKα and Rb antibodies. (C) Immunoprecipitation assay showing the level of E2F1 bound to Rb in NPCs expressing GFP (control), caAMPK, or dnAMPK; *p<0.005.
Figure 25:
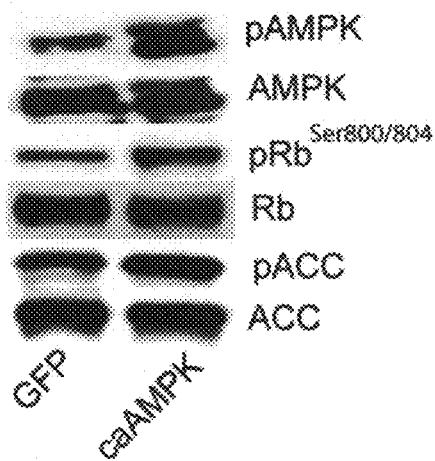
Figure 25:
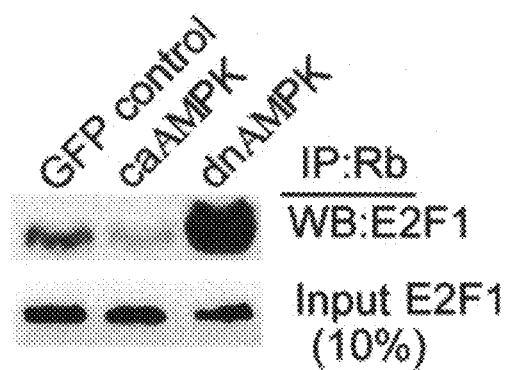

Stem Cell Growth Factors as Well as Metabolic Perturbations Activate AMPK to Promote NPC Proliferation We extended our studies to explore whether WT NPC growth was enhanced by activation of AMPK via genetic or physiological stimuli. Constitutively active AMPK not only enhanced proliferation of WT NPCs (FIG. 25A), but also caused a significant increase in Rb phosphorylation (FIG. 25B). Accordingly, the proportion of E2F1 sequestered by Rb was reduced in WT NPCs expressing caAMPK, whereas dnAMPK caused significantly more E2F1 sequestration (FIG. 25C). It is intriguing that overexpression of the β1 subunit, but not the β2 subunit, caused a distinct increase in WT NPC growth (FIGS. 19C and 25A), supporting its role in regulating AMPK-mediated NPC proliferation.

The effects of AMPKβ1 deletion on Rb phosphorylation led us to consider whether the highly conserved AMPK signaling pathway is fundamentally important for NPC responses to proliferative signals, such as growth factors. We cultured WT NPCs in the absence of growth factors for 2 hr (withdrawal phase) and then added back epidermal growth factor (EGF) and fibroblast growth factor (FGF) for 1 hr. Cells treated with growth factors had increased levels of pAMPK and increased phosphorylation of Rb at Ser804. However, when EGF and FGF were added to cells treated with the AMPK inhibitor compound C, no increase in pAMPK or pRb was observed (FIG. 23E, FIG. 54A). Furthermore, pharmacologic inhibition of AMPK drastically reduces proliferation of Neural Stem and Progenitor cells (NPCs) (FIG. 26A, FIG. 26B). Embryonic day 12.5 forebrain wildtype NPCs were cultured for 4 days and seeded as single cells in presence of DMSO (control), or the AMPK inhibitors Compound C (10 μM) and Adenine 9-β-D-arabinofuranoside (Ara A 1 mM). Following 48 hours of growth in medium supplemented with EGF (10 μM) and bFGF (10 μM), neurospheres were trypsinized, and trypan blue negative (live) cells were counted on a hemocytometer. * $p<0.001$ Thus, it appears that the failure of AMPK-directed phosphorylation of Rb in β1−/− NPCs, possibly in response to endogenous growth factors, results in defects in G2M phase as well as the aberrant differentiation that leads to apoptosis.

AMPK is integrally involved in regulating cellular energy homeostasis and is activated by low cellular ATP levels, such as occurs by limiting oxygen or glucose supplies or exercise, conditions that enhance proliferative capacity of stem cells (Burgers et al., Exp. Brain Res. 188, 33-43, 2008; Fu et al., Diabetologia 49, 1027-1038, 2006; Stolzing et al., Rejuvenation Res. 9, 31-35, 2006). To explore whether the proliferative effects of glucose restriction are manifested through activation of the AMPK-Rb axis, we monitored the growth of WT NPCs cultured in 2.5-25 mM (the amount present in neurobasal medium) glucose for 48 hr. NPC cell numbers were increased when grown in low-glucose medium, with 5 mM glucose giving the highest growth rate (FIG. 54B). The NPC growth stimulation by low glucose was not observed in cells treated with compound C, which severely inhibited neurosphere growth. Furthermore, no effect on growth by low glucose was observed in β1−/− NPCs, consistent with their lack of AMPK signaling (FIG. 54C). Interestingly, there was a small but consistent increase in the phosphorylation of AMPK, Rb, and ACC at lower glucose concentrations (FIG. 54D, FIG. 54E; FIG. 55A-E). Remarkably, glucose limitation also reduced the proportion of Rb-bound E2F1, whereas compound C treatment caused higher levels of Rb sequestration of E2F1 (FIG. 56A). Collectively, our results demonstrate that, perhaps, growth factor signaling, as well as other physiological/metabolic stimuli, utilize the AMPK-Rb signaling pathway to modulate the growth and differentiation of NPCs during mammalian brain development.

The loss of axonal and dendritic processes in β1−/− postnatal brain is consistent with the neurodegeneration phenotype observed in AMPK γ (Tschape et al., EMBO J. 21, 6367-6376, 2002) and β subunit-deficient (Spasic et al., J. Neurosci. 28, 6419-6429, 2008) Drosophila models. Interestingly, in Drosophila, loss of the entire β subunit gene was functionally equivalent to the loss of β subunit C-terminal exons, consistent with our findings in mice. Thus, it appears that, besides being required during embryonic differentiation, AMPK is also necessary for maintaining the structural and functional integrity of mammalian neurons. However, unlike the case in epithelial cells, where the AMPK-LKB1 axis influences polarity (Lee et al., Nature 447, 1017-1020, 2007; Mirouse et al., J. Cell Biol. 177, 387-392, 2007), we observed no morphological changes reflective of altered neuronal polarity, nor did we observe an altered distribution of the polarity proteins PAR3 or pPKCζ (FIG. 38). Why AMPKβ1 deficiency causes specific loss of neurons and oligodendrocytes, but not astrocytes, is unclear; however, it should be noted that astrocyte differentiation can proceed normally in the absence of Rb (Marino et al., 2000). β1−/− astrocytes do not differentiate normally, suggesting that additional AMPK-modulated pathways are important in these cells. On the other hand, it is tempting to speculate that hypophosphorylation of Rb at Ser804 in NPCs might contribute to the altered ratio of neural cells in vivo.

The present inventors have identified AMPK as a novel kinase for Rb and show that loss of AMPK activity in AMPKβ1-deficient animals causes Rb hypophosphorylation and multiple resultant NPC defects. Although CDK4/6 can phosphorylate Rb at Ser804 (Zarkowska, T., et al., J. Biol. Chem. 272, 12738-12746, 1997), the phosphorylation of this site is dramatically decreased in β1−/− NPCs. The hypophosphorylation of Rb at Ser804, despite normal levels of the two G1 cyclins (D1 and D2) raises two fundamental questions. Is AMPK the primary kinase that phosphorylates Rb at this residue in NPCs in vivo? And, are multiple residues in Rb targeted by AMPK or is the hypophosphorylation of Ser804 solely responsible for the NPC defects? The decreased number of mitotic cells in the ventricular zone of the β1−/− brains where neural stem cells undergo self-renewal, together with the large number of apoptotic cells outside the ventricular zone where progenitor cells proliferate, migrate and differentiate indicate that Rb phosphorylation at Ser804 by AMPK is necessary for multiple aspects of NPC biology.

The regulation of Rb by AMPK is particularly intriguing as the Rb-E2F pathway is involved in fate specification and differentiation of multiple cell types that include neurons (Lee, E. Y., et al., Nature. 359, 288-294, 1992; Callaghan, D. A., et al., Dev. Biol. 207, 257-70, 1999), cardiac stem cells (Papadimou, E., et al., EMBO J. 24, 1750-61, 2005), adipocytes (Dali-Youcef, N., et al., Proc. Natl. Sci. USA. 104, 10703-10708, 2007; Fajas, L., et al., Dev. Cell. 3, 903-910, 2002), erythrocytes (Sankaran, V. G., et al., Genes Dev. 22, 463-475, 2008), and epithelial cells (Wikenheiser-Brokamp, K. A., Development. 131, 4299-4310, 2004). Rb bound E2F1 actively represses transcription (Weintraub, S. J., et al., Nature. 375, 812-815, 1995) and, in addition, hypophosphorylated Rb inhibits the metabolic regulator PPARγ (Fajas, L., et al., Dev. Cell. 3, 903-910, 2002). Finally, excess E2F activity due to the absence of Rb causes impaired erythroid differentiation due to decreases in mitochondrial biogenesis (Sankaran, V. G., et al., Genes Dev. 22, 463-475, 2008). Thus, abnormalities in the Rb-E2F axis can play a role in the differentiation defects observed in β1−/− NPCs. AMPKβ1 deletion causes specific loss of neurons and oligodendrocytes and not astrocytes; astrocyte differentiation proceeds normally in the absence of Rb (Marino, S., et al., Genes Dev. 14, 994-1004, 2000). Finally, the identification of Rb as an AMPK substrate indicates that cell proliferation and fate choice could be influenced by intracellular energy levels through the actions of AMPK.

Without being limited by theory, the present findings suggest that the differential subcellular localization and/or other yet unidentified modifications of the two β subunits can directly regulate AMPK substrate choice in a context-dependent manner such that AMPK stimulates proliferation in energy-replete conditions, but mediates survival adaptations during periods of energy depletion.

The present inventors have found that administration of inhibitors of AMPK can decrease stem cell proliferation. Administration of AMPK inhibitors provides new methods for inhibiting the growth (and increase the death) of cancer cells and can be used in treating a variety of cancers, particularly in view of recent finding that many if most cancers are likely to be derived from cancer stem cells. In addition, AMPK activators can be used to promote stem cell growth by increasing proliferation, self-renewal and differentiation. An AMPK activator can thus be administered in a therapeutically effective amount for increasing numbers of stem cell-derived neuronal progenitor cells. The present methods can thus be used for stimulating replacement cells for repair of the injured spinal cord, or for stimulating increased neurogenesis in the hippocampus, a process thought to be important for maintaining high levels of learning and memory during aging, and responsible for the link between increased exercise and increased mental acuity. Furthermore, selective differentiation of stem cells to a desired cell type can be achieved by altering cellular AMPK activity using small molecules. Such approaches can be useful for cell based therapies.

The present teachings include the following aspects:

1. A method of treating a cancer, the method comprising administering to a subject in need of treatment, an inhibitor of AMPK activity in an amount effective to decrease proliferation of cancer stem cells comprised by the subject.
2. A method of treating a cancer in accordance with aspect 1, wherein the cancer stem cells are neural cancer stem cells.
3. A method of treating a cancer in accordance with aspect 1 or aspect 2, further comprising administering to the subject a cancer therapy selected from the group consisting of a cancer chemotherapy, a cancer radiation therapy and a combination thereof.
4. A method of treating a cancer, the method comprising administering to a subject in need of treatment, an inhibitor of AMPK activity in an amount effective to enhance apoptosis in cancer stem cells comprised by the subject.
5. A method of treating a cancer in accordance with aspect 4, wherein the cancer stem cells comprise neural cancer stem cells.
6. A method of treating a cancer in accordance with aspect 4 or aspect 5, further comprising administering to the subject a cancer therapy selected from the group consisting of a cancer chemotherapy, a cancer radiation therapy and a combination thereof.
7. A method of treating a cancer, the method comprising administering to a subject in need of treatment an activator of AMPK activity in an amount effective to induce a cancer stem cell to differentiate into a specialized cell type.
8. A method of treating a cancer in accordance with aspect 7, wherein the cancer stem cell is a neural cancer stem cell.
9. A method of treating a cancer in accordance with aspect 8, wherein the specialized cell type is an oligodendrocyte.
10. A method of inducing selective differentiation in a stem cell, the method comprising contacting the stem cell with an AMPK inhibitor.
11. A method of inducing selective differentiation in a stem cell in accordance with aspect 10, wherein the stem cell is a neural stem cell.
12. A method of inducing selective differentiation in a stem cell in accordance with aspect 10, wherein the stem cell is a cancer stem cell.

13. A method of any one of aspects 1-12, wherein the AMPK inhibitor is selected from the group consisting of and Compound C and Adenine 9-β-D-arabinofuranoside (Ara A).
14. A method of treating a neural deficiency, disease, or disorder of neural function in a subject in need thereof, the method comprising administering to the subject an activator of AMPK activity.
15. A method of treating a neural deficiency, disease, or disorder of neural function in accordance with aspect 14, wherein the neural deficiency, disease, or disorder is selected from the group consisting of a spinal cord injury, a brain trauma injury, a deficiency in cognitive ability, a neurodegenerative disease, a deficiency in memory, a demyelinating disease, a dysmyelinating disease, and a hereditary metabolic disorder affecting myelination.
16. A method of treating a neural deficiency, disease, or disorder of neural function in accordance with aspect 15, wherein the neurodegenerative diseases is selected from the group consisting of Alzheimer's disease, Parkinsons disease, ALS and multiple sclerosis.
17. A method of treating a neural deficiency, disease, or disorder of neural function in accordance with aspect 14, wherein the deficiency is a irradiation-induced deficiency, a chemotherapy-induced deficiency, an ischemia-induced deficiency, a brain trauma-induced deficiency, a premature birth-induced deficiency, a nutritional deprivation-induced deficiency, or a combination thereof.
18. A method of any one of aspects 14-17, wherein the AMPK activator is administered in an amount effective to stimulate formation and/or differentiation of oligodendrocytes.
19. A method of expanding a neural stem cell population in a subject, the method comprising administering to the subject an activator of AMPK activity.
20. A method of expanding a neural stem cell population in a subject in accordance with aspect 19, wherein the administering comprises administering a proliferation-enhancing amount of the AMPK activator.
21. A method of expanding a neural stem cell population in a subject in accordance with aspect 19, wherein the administering comprises administering a self-renewal-enhancing amount of the AMPK activator.
22. A method of expanding a neural stem cell population in a subject in accordance with aspect 19, wherein the administering comprises administering an apoptosis-suppressing amount of the AMPK activator.
23. A method of expanding a neural stem cell population in vitro, the method comprising: contacting a cell culture comprising at least one neural stem cell with an AMPK activator.
24. A method of expanding a neural stem cell population in vitro in accordance with aspect 23, wherein the contacting the cell culture with an AMPK activator comprises contacting the culture with the AMPK activator in an amount effective for increasing proliferation of the at least one neural stem cell.
25. A method of expanding a neural stem cell population in vitro in accordance with aspect 23, wherein the contacting the cell culture with an AMPK activator comprises contacting the culture with the AMPK activator in an amount effective for enhancing self-renewal of the at least one neural stem cell.
26. A method of expanding a neural stem cell population in vitro in accordance with aspect 23, wherein the contacting the cell culture with an AMPK activator comprises contacting the culture with the AMPK activator in an amount effective for decreasing apoptosis of the stem cells.
27. A cell-based therapeutic method for treating a neural deficiency, disease, or disorder of neural function, comprising:
expanding a neural stem cell population in vitro by the method of any one of aspects 23-26; and
administering neural stem cells of the expanded population to a subject in need of treatment.
28. A cell-based therapeutic method in accordance with aspect 27, wherein the neural stem cell population in vitro comprises neural stem cells autologous to the subject.
29. A method of expanding a cancer stem cell population in vitro, the method comprising: contacting a cell culture comprising at least one cancer stem cell with an AMPK activator.
30. A method of expanding a cancer stem cell population in vitro in accordance with aspect 29, wherein the contacting the cell culture with an AMPK activator comprises contacting the culture with the AMPK activator in an amount effective for increasing proliferation of the at least one cancer stem cell.
31. A method of expanding a cancer stem cell population in vitro in accordance with aspect 29, wherein the contacting the cell culture with an AMPK activator comprises contacting the culture with the AMPK activator in an amount effective for enhancing self-renewal of the at least one cancer stem cell.
32. A method of expanding a cancer stem cell population in vitro in accordance with aspect 29, wherein the contacting the cell culture with an AMPK activator comprises contacting the culture with the AMPK activator in an amount effective for decreasing apoptosis of the cancer stem cells.
33. A method of screening a chemotherapeutic compound, the method comprising:
expanding a cancer stem cell population in vitro by the method of any one of aspects 29-32;
contacting cells comprised by the expanded cell population with a candidate chemotherapeutic agent; and
determining the effectiveness of the candidate chemotherapeutic agent.
34. A method of screening a chemotherapeutic compound in accordance with aspect 33, wherein the cancer stem cell population in vitro comprises cancer stem cells autologous to a subject.
35. A method of inducing selective differentiation in a stem cell, the method comprising contacting the stem cell with an AMPK activator.
36. A method in accordance with any one of aspects 14-35, wherein the AMPK activator is selected from the group consisting of Metformin and 5-Aminoimidazole-4-carboxamide-1-beta-d-ribofuranoside (AICAR).
37. A method of screening a compound for activity as an AMPK activator, the method comprising:
providing a cell culture comprising cells expressing a) AMPK and b) a polypeptide comprising an Rb phosphorylation site;
contacting the cells with a candidate compound; and
detecting an increase in phosphorylation of the Rb phosphorylation site.
38. A method of screening a compound for activity as an AMPK activator in accordance with Aspect 37, wherein the cell culture comprises neural stem cells.
39. A method of screening a compound for activity as an AMPK activator in accordance with Aspect 37, wherein the polypeptide comprising an Rb phosphorylation site comprises amino acid sequence ISPLKSPYKI (SEQ ID NO.: 1).

40. A method of screening a compound for activity as an AMPK activator in accordance with Aspect 37, wherein the detecting an increase in phosphorylation of the Rb phosphorylation site comprises contacting the polypeptide with an antibody against the polypeptide comprising the Rb phosphorylation site.

41. A method of screening a compound for activity as an AMPK activator in accordance with Aspect 40, wherein the antibody against the polypeptide comprising the Rb phosphorylation site is a phospho-specific antibody.

42. A method of screening a compound for activity as an AMPK activator in accordance with Aspect 40, wherein the antibody is an antibody against pRbSer$^{800/804}$.

43. A method of screening a compound for activity as an AMPK activator in accordance with Aspect 42, wherein the antibody against pRbSer$^{800/804}$ is a polyclonal antibody against pRbSer$^{800/804}$.

44. A method of screening a compound for activity as an AMPK activator, the method comprising:
forming a mixture comprising a) AMPK and b) a polypeptide comprising an Rb phosphorylation site;
contacting the mixture with a candidate compound; and
detecting an increase in phosphorylation of the Rb phosphorylation site.

45. A method of screening a compound for activity as an AMPK activator in accordance with Aspect 44, wherein the polypeptide comprising an Rb phosphorylation site comprises amino acid sequence ISPLKSPYKI (SEQ ID NO.: 1).

46. A method of screening a compound for activity as an AMPK activator in accordance with Aspect 44, wherein the detecting a decrease in phosphorylation of the Rb phosphorylation site comprises contacting the polypeptide with an antibody against the polypeptide comprising the Rb phosphorylation site.

47. A method of screening a compound for activity as an AMPK activator in accordance with Aspect 46, wherein the antibody against the polypeptide comprising the Rb phosphorylation site is a phospho-specific antibody.

48. A method of screening a compound for activity as an AMPK activator in accordance with Aspect 46, wherein the antibody is an antibody against pRbSer$^{800/804}$.

49. A method of screening a compound for activity as an AMPK activator in accordance with Aspect 46, wherein the antibody is a pan antibody against the polypeptide comprising the Rb phosphorylation site.

50. A method of screening a compound for activity as an AMPK inhibitor, the method comprising:
providing a cell culture comprising cells expressing a) AMPK and b) a polypeptide comprising an Rb phosphorylation site;
contacting the cells with a candidate compound; and
detecting a decrease in phosphorylation of the Rb phosphorylation site.

51. A method of screening a compound for activity as an AMPK inhibitor in accordance with Aspect 50, wherein the cell culture comprises neural stem cells.

52. A method of screening a compound for activity as an AMPK inhibitor in accordance with Aspect 50, wherein the polypeptide comprising an Rb phosphorylation site comprises amino acid sequence ISPLKSPYKI (SEQ ID NO.: 1).

53. A method of screening a compound for activity as an AMPK inhibitor in accordance with Aspect 50, wherein the detecting an decrease in phosphorylation of the Rb phosphorylation site comprises contacting the polypeptide with an antibody against the polypeptide comprising the Rb phosphorylation site.

54. A method of screening a compound for activity as an AMPK inhibitor in accordance with Aspect 53, wherein the antibody against the polypeptide comprising the Rb phosphorylation site is a phospho-specific antibody.

55. A method of screening a compound for activity as an AMPK inhibitor in accordance with Aspect 53, wherein the antibody is an antibody against pRbSer$^{800/804}$.

56. A method of screening a compound for activity as an AMPK inhibitor in accordance with Aspect 53, wherein the antibody against the polypeptide comprising the Rb phosphorylation site is a pan antibody against the polypeptide comprising the Rb phosphorylation site.

57. A method of screening a compound for activity as an AMPK inhibitor, the method comprising:
forming a mixture comprising a) AMPK and b) a polypeptide comprising an Rb phosphorylation site;
contacting the mixture with a candidate compound; and
detecting a decrease in phosphorylation of the Rb phosphorylation site.

58. A method of screening a compound for activity as an AMPK activator in accordance with Aspect 57, wherein the polypeptide comprising an Rb phosphorylation site comprises amino acid sequence ISPLKSPYKI (SEQ ID NO.: 1).

59. A method of screening a compound for activity as an AMPK activator in accordance with Aspect 58, wherein the detecting a decrease in phosphorylation of the Rb phosphorylation site comprises contacting the polypeptide with an antibody against the polypeptide comprising the Rb phosphorylation site.

60. A method of screening a compound for activity as an AMPK inhibitor in accordance with Aspect 59, wherein the antibody against the polypeptide comprising the Rb phosphorylation site is a phospho-specific antibody.

61. A method of screening a compound for activity as an AMPK inhibitor in accordance with Aspect 59, wherein the antibody is an antibody against pRbSer$^{800/804}$.

62. A method of screening a compound for activity as an AMPK inhibitor in accordance with Aspect 59, wherein the antibody is a pan antibody against the polypeptide comprising the Rb phosphorylation site.

63. A method in accordance with aspect 44 or aspect 57, wherein the mixture comprises a bacterial lysate comprising the polypeptide.

64. A method in accordance with any one of aspects 37-63, wherein the polypeptide comprises a full-length Rb polypeptide.

65. A method in accordance with any one of aspects 37-40, 44-46, 50-53, and 57-59 wherein the detecting comprises detecting presence, absence or quantity of binding of an antibody directed against a phosphorylated Rb phosphorylation site.

66. A method in accordance with any one of aspects 37-40, 44-46, 50-53, and 57-59, further comprising adding to the mixture or cell culture a radiolabelled ATP, wherein the detecting comprises detecting presence, absence or quantity of radiolabel incorporated into the polypeptide.

All publications, patents, patent applications and other references cited in this application are herein incorporated by reference in their entirety as if each individual publication, patent, patent application or other reference were specifically and individually indicated to be incorporated by reference.

What is claimed is:

1. A method of screening a compound for activity as an AMPK activator, the method comprising:
providing a cell culture comprising neural stem cells expressing a) AMPK and b) a polypeptide comprising an Rb phosphorylation site;
contacting the cells with a candidate compound; and
detecting an increase in phosphorylation of the Rb phosphorylation site,
whereby an increase in Rb phosphorylation indicates that the compound may be an AMPK activator.

2. A method of screening a compound for activity as an AMPK activator in accordance with claim 1, wherein the polypeptide comprising an Rb phosphorylation site comprises amino acid sequence ISPLKSPYKI (SEQ ID NO.: 1).

3. A method of screening a compound for activity as an AMPK activator in accordance with claim 1, wherein the detecting an increase in phosphorylation of the Rb phosphorylation site comprises contacting the polypeptide with an antibody against the polypeptide comprising the Rb phosphorylation site.

4. A method of screening a compound for activity as an AMPK activator in accordance with claim 3, wherein the antibody against the polypeptide comprising the Rb phosphorylation site is a phospho-specific antibody.

5. A method of screening a compound for activity as an AMPK activator in accordance with claim 3, wherein the antibody is an antibody against $pRbSer^{800/804}$.

6. A method of screening a compound for activity as an AMPK activator in accordance with claim 3, wherein the antibody against the polypeptide comprising the Rb phosphorylation site is a pan antibody.

7. A method of screening a compound for activity as an AMPK inhibitor, the method comprising:
providing a cell culture comprising neural stem cells expressing a) AMPK and b) a polypeptide comprising an Rb phosphorylation site;
contacting the cells with a candidate compound; and
detecting a decrease in phosphorylation of the Rb phosphorylation site,
whereby a decrease in Rb phosphorylation indicates that the compound may be an AMPK inhibitor.

8. A method of screening a compound for activity as an AMPK inhibitor in accordance with claim 7, wherein the polypeptide comprising an Rb phosphorylation site comprises amino acid sequence ISPLKSPYKI (SEQ ID NO.: 1).

9. A method of screening a compound for activity as an AMPK inhibitor in accordance with claim 7, wherein the detecting an decrease in phosphorylation of the Rb phosphorylation site comprises contacting the polypeptide with an antibody against the polypeptide comprising the Rb phosphorylation site.

10. A method of screening a compound for activity as an AMPK inhibitor in accordance with claim 9, wherein the antibody against the polypeptide comprising the Rb phosphorylation site is a phospho-specific antibody.

11. A method of screening a compound for activity as an AMPK inhibitor in accordance with claim 9, wherein the antibody is an antibody against $pRbSer^{800/804}$.

12. A method of screening a compound for activity as an AMPK inhibitor in accordance with claim 9, wherein the antibody against the polypeptide comprising the Rb phosphorylation site is a pan antibody.

* * * * *